(12) United States Patent
Fine et al.

(10) Patent No.: US 11,612,328 B2
(45) Date of Patent: **\*Mar. 28, 2023**

(54) METHOD AND APPARATUS FOR HEMODYNAMICALLY CHARACTERIZING A NEUROLOGICAL OR FITNESS STATE BY DYNAMIC LIGHT SCATTERING (DLS)

(71) Applicant: ELFI-TECH LTD., Rehovot (IL)

(72) Inventors: Ilya Fine, Rehovot (IL); Alexander Kaminsky, IL (IL)

(73) Assignee: ELFI-TECH LTD., Rehovot (IL)

( \* ) Notice: Subject to any disclaimer, the term of this patent is extended or adjusted under 35 U.S.C. 154(b) by 173 days.

This patent is subject to a terminal disclaimer.

(21) Appl. No.: 16/992,157

(22) Filed: Aug. 13, 2020

(65) Prior Publication Data

US 2021/0093204 A1    Apr. 1, 2021

Related U.S. Application Data

(63) Continuation of application No. 15/770,590, filed as application No. PCT/IB2016/001240 on Aug. 15, 2016, now Pat. No. 10,952,622.
(Continued)

(51) Int. Cl.
*A61B 5/0205*     (2006.01)
*A61B 5/026*      (2006.01)
(Continued)

(52) U.S. Cl.
CPC .......... *A61B 5/0205* (2013.01); *A61B 5/0261* (2013.01); *A61B 5/0285* (2013.01); *A61B 5/165* (2013.01); *A61B 5/7253* (2013.01)

(58) Field of Classification Search
CPC ... A61B 5/0205; A61B 5/0261; A61B 5/0285; A61B 5/165; A61B 5/7253
See application file for complete search history.

(56) References Cited

U.S. PATENT DOCUMENTS 6,805,673 B2 \* 10/2004 Dekker ............. A61B 5/02405
                                                              600/324
2009/0209834 A1 \* 8/2009 Fine .................... A61B 5/0261
                                                              600/479

(Continued)

*Primary Examiner* — Christopher A Flory
(74) *Attorney, Agent, or Firm* — Momentum IP; Marc Van Dyke

(57) ABSTRACT

A method and apparatus for hemodynamically characterizing a neurological or fitness state by dynamic scattering light (DLS) is disclosed herein. In particular, a non-pulsatile blood-shear-rate-descriptive (BSRD) signal(s) is optically generated and analyzed. In some embodiments, the BSRD signal is generated dynamically so as to adaptively maximize (i.e. according to a bandpass or frequency-selection profile) a prominence of a predetermined non-pulsatile physiological signal within the BSRD. In some embodiments, the BSRD is subjected to a stochastic or stationary-status analysis. Alternatively or additionally, the neurological or fitness state may be computed from multiple BSRDs, including two or more of: (i) a [sub −200 Hz, ~300 Hz] BSRD signal; (ii) a [~300 Hz, ~1000 Hz] signal; (iii) a [~1000 Hz, ~4000 Hz] signal and (iv) a [~4000 Hz, z Hz] (z>=7,000) signal.

14 Claims, 66 Drawing Sheets

Related U.S. Application Data

(60) Provisional application No. 62/295,138, filed on Feb. 14, 2016, provisional application No. 62/249,303, filed on Nov. 1, 2015.

(51) Int. Cl.
  *A61B 5/0285* (2006.01)
  *A61B 5/16* (2006.01)
  *A61B 5/00* (2006.01)

(56) References Cited

U.S. PATENT DOCUMENTS

| | | | |
|---|---|---|---|
| 2011/0082355 A1* | 4/2011 | Eisen | A61B 5/7207 600/324 |
| 2013/0131475 A1* | 5/2013 | Eisen | A61B 5/7207 600/324 |
| 2014/0094666 A1* | 4/2014 | Fine | A61B 5/7278 600/324 |
| 2015/0105638 A1* | 4/2015 | Eisen | A61B 5/14546 600/324 |
| 2018/0153420 A1* | 6/2018 | Fine | A61B 5/02416 |
| 2018/0160913 A1* | 6/2018 | Fine | A61B 5/14552 |

* cited by examiner

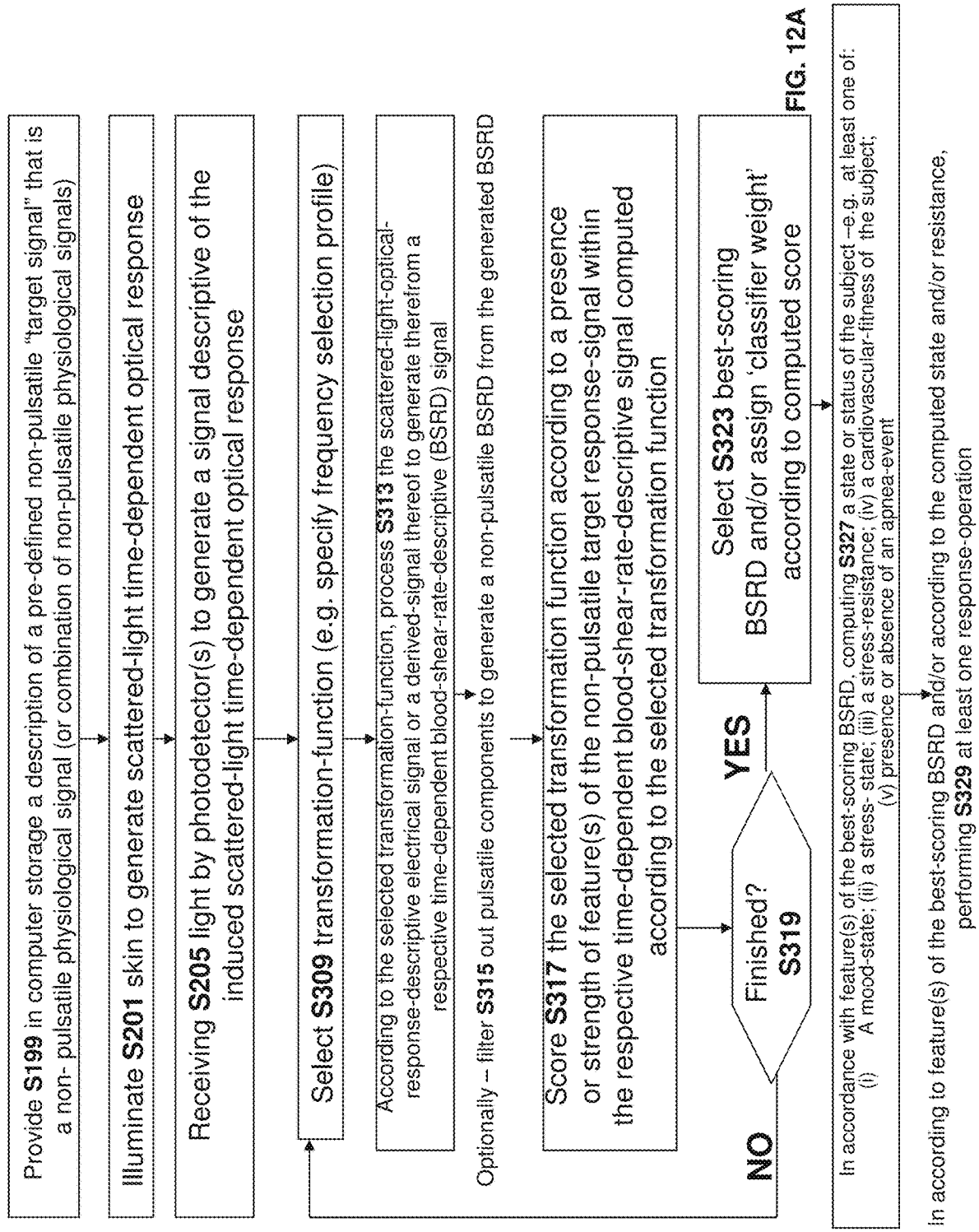

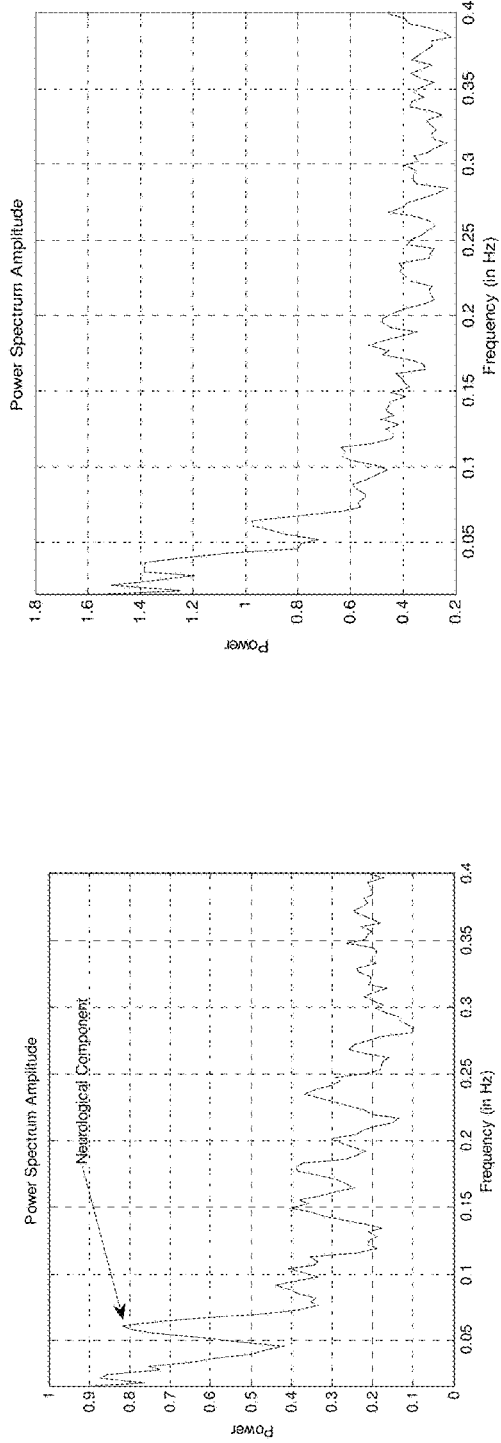
FIG. 27A
FIG. 27B
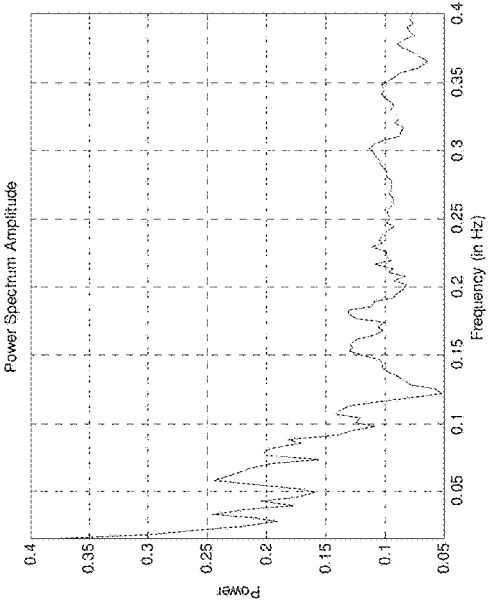
FIG. 27C
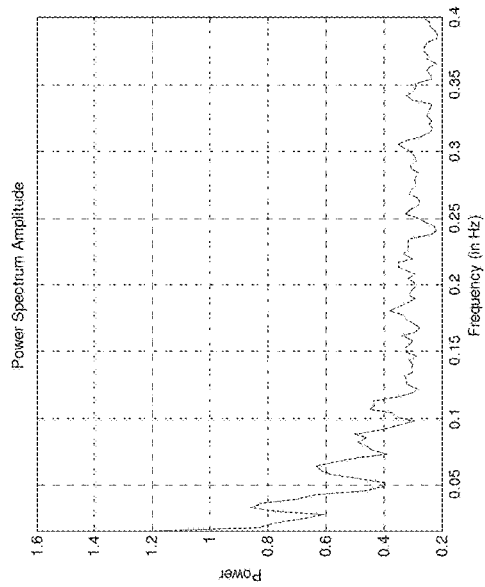
FIG. 27D

METHOD AND APPARATUS FOR HEMODYNAMICALLY CHARACTERIZING A NEUROLOGICAL OR FITNESS STATE BY DYNAMIC LIGHT SCATTERING (DLS)

BACKGROUND

Detecting Emotion-State/Stress-State/Mood-State

There is an ongoing need for detecting emotional state, stress-states, and mood-states of warm-blooded (e.g. mammals or birds) individuals. Prior art techniques for detecting an emotional state are based on analyzing facial expressions, voice intonations, text generated by the subject, eye movement, pulse and blood pressure variability.

Thus, it has been known for many years that as a subject gets nervous or excited or scared, his/her pulse-rate (HR) tends to temporarily increase (i.e. relative to a baseline pulse) until the stress-state or mood-state passes. Thus, it is possible to detect a person's stress-state or mood-state using any pulse-meter or ECG device. Examples of devices for non-invasive optical measuring pulse include pulse oximeters and dynamic light scattering (DLS) devices disclosed in WO 2008/053474 and WO2012064326, each of which is incorporated herein by reference in its entirety.

Based on the time variations pattern of HR, which is call Heart Rate Variability (HRV), some of the manifestations of the Central Nervous System (CNS) are subject to algorithmic representations. Specifically, the responses of sympathetic and parasympathetic nervous system are reflected in HRV. Naturally, any expressions of stress or emotions also affect the HRV pattern. Unfortunately, HRV by itself tends to be of limited reliability, specificity and accuracy. For example, due to natural variations, 'baseline' pulse rate and HRV may be difficult or impossible to accurately gauge. In addition, there may be many 'false positive' situations where a user's pulse increases for reasons (e.g. the user is climbing up the stairs) other than being in an excited emotional state, In addition, HR and HRV are of at most limited utility when attempting to differentiate between different types of 'excited' states—i.e. between fearful and angry. In addition in order to extract HRV parameters reliably, at least 5 minutes of the measurement are required. This fact may impose additional limitations for consumer applications of HRV.

Detecting Fitness Parameters

There is an ongoing need for non-invasive and continuous methods (and related apparatus) for detecting a 'fitness-parameter' of an individual. Thus, a 'low fitness' score may be indicative of an elevated risk of cardio-vascular disease or reduced capability to withstand a load. Unfortunately, preventative care is often neglected, for example, due to the high cost (or inconvenience) of physician visits.

HR and HRV are also can provide some indications for cardio-vascular status however, since the same parameters respond to stress and emotional stages, they lack of specificity.

Once again, HR and HRV are useful as rough indicators but, by themselves, are not robust enough for consistently obtaining accurate readings for many subjects.

Pulsatile and Non-Pulsatile Blood

FIG. 1A schematically illustrates blood flow within a blood vessel. As illustrated, at the vessel walls due to the 'no-slip' boundary condition, blood velocity (and hence shear rate) drops off to zero.

When any pressure gradient is applied to a vessel (i.e. in the case of blood vessels, this is a 'pulsatile pressure-wave'), fluid within the vessel flows according to the pressure gradient. However, at locations near the blood vessel wall, temporal fluctuations in velocity (and shear) are not strongly correlated to those of the pulse-wave (e.g. because the blood vessel wall is not perfectly rigid). Similarly, there may be at most very weak correlation between the blood flow and pulsatile components in the very small vessels (capillary vessels), where the size of the moving particles (i.e. red blood cells (RBSs)) are comparable to the blood diameter.

As shown in FIG. 1A, in arterial vessels, at locations closer to the center-line the blood may be regarded as 'pulsatile blood' (i.e. due to its flow properties) where temporal fluctuations in velocity (and shear rate) are strongly correlated with the pulsatile pulse-pressure wave. In contrast, there is little or no correlation between temporal fluctuations of shear rate and those of the pulse-pressure wave at locations near the blood vessel wall. Thus, in FIG. 1A, blood near the wall is labeled as 'non-pulsatile blood.' The terms 'pulsatile blood' and 'non-pulsatile blood' refer to flow properties of the blood—i.e. how the blood is flowing in vivo.

Referring to FIG. 1B, it is noted that blood flow in arteries is mostly pulsatile, while in many other blood vessels (e.g. capillaries), the opposite is true.

Modulation of Blood Flow (and Blood Shear) by Physiological Signals

Reference is now made to FIG. 2.

As noted in the article "Physics of the Human Cardiovascular System" by Stefanovska and Bracic[1], in addition to the HRV, the CNS affects the "blood flow variability". The CNS governs multiple physiological processes which can be expressed in terms of peripheral blood oscillations in different frequency bands.

Listed in FIG. 2 (adapted from FIG. 10 of Stefanovska and Bracic) are the following categories of physiological processes, each of which functions as an 'oscillator' of the blood flow signal in a respective frequency band: (i) metabolic process(es) which modulate blood flow signal in the frequency band [~0.01 Hz, ~0.02 Hz]; (ii) neurogenic process(es) which modulate blood flow signal in the frequency band [~0.02 Hz, ~0.06 Hz]; (iii) myogenic process(es) which modulate blood flow signal in the frequency band [~0.06 Hz, ~0.15 Hz]; (iv) respiratory process(es) which modulate blood flow signal in the frequency band [~0.15 Hz, ~0.5 Hz]; and (v) heart/pulsatile process(es) which modulate blood flow signal in the frequency band [~0.4 Hz, ~2 Hz].

The aforementioned frequency bands are for humans—for other mammals, the frequency values may differ.

Physiological processes of each category of processes modulate the blood-flow (and also the blood-shear) 'signal.' Because blood flow (and blood-shear) signal may be considered a combination of multiple signals, physiological processes may be said to generate a 'physiological response signal' present within the blood-flow (and also the blood-shear signal)—each physiological signal may be said to 'contribute' to the overall blood-flow oscillation pattern (and also the blood-shear signal). For the present disclosure, the term 'response signal' therefore relates to the response(s) to input and/or feedback from the central nervous system as manifested within blood flow.

One example of a physiological response signal is a Mayer wave.

[1] Physics of the human cardiovascular system by Aneta Stefanovska and Maja Bracic, *Contemporary Physics*, 1999, volume 40, number 1. Pages 31-55

It is noted that the heart/pulsatile signal is the well-known 'pulsatile signal'—the pumping of blood by the heart directly influences the blood flow (and blood-shear)

response signal in many locations within the circulatory system. In contrast, the 'respiratory signal' from the 'respiratory processes/oscillators' is not merely the 'breathing pattern'—instead, this refers to the indirect influence of respiration upon blood flow.

One example of a myogenic process is Mayer waves. According to Wikipedia:

Mayer waves are cyclic changes or waves in arterial blood pressure brought about by oscillations in baroreceptor and chemoreceptor reflex control systems. The waves are seen both in the ECG and in continuous blood pressure curves and have a frequency about 0.1 Hz (10-second waves). These waves were originally described by Siegmund Mayer, Ewald Hering and Ludwig Traube hence originally called "Traube-Hering-Mayer waves".

Mayer waves can be defined as arterial blood pressure (AP) oscillations at frequencies slower than respiratory frequency and which show the strongest, significant coherence (strength of linear coupling between fluctuations of two variables in the frequency domain) with efferent sympathetic nervous activity (SNA). In humans, AP oscillations which meet these properties have a characteristic frequency of approx. 0.1 Hz; 0.3 Hz in rabbits and 0.4 Hz in rats.

The hemodynamic basis of Mayer waves are oscillations of the sympathetic vasomotor tone of arterial blood vessels, because Mayer waves are abolished or at least strongly attenuated by pharmacological blockade of alpha-adrenoreceptors. Within a given biological species, their frequency is fairly stable; in humans it has been shown that this frequency does not depend on gender, age or posture. It has been suggested that Mayer waves trigger the liberation of endothelium-derived nitric oxide (NO) by cyclic changes of vascular shear stress which could be beneficial to end organ functioning.

Mayer waves are correlated with heart rate variability.

Takalo et al. (1999) state that "the frequency shift of Mayer waves to lower frequencies is associated with an increased risk of developing established hypertension."

In pulsatile blood, the heart/pulsatile shear signal is characterized by well-known features, illustrated in FIG. 2B. In arterial component of the flow, there may be signals other than the pulsatile signal—however, typically the energy of the pulsatile signal dominates that of the other physiological signals.

Dynamic Light Scattering (DLS) for Non-Invasive In-Vivo Measurement of Biological Parameters WO 2008/053474 and WO2012064326, each of which are incorporated herein by reference in its entirety, each disclose a system and method for in vivo measurement of biological parameters by dynamic light scattering techniques.

In particular, WO 2008/053474 discloses a novel optical technique suitable for the in vivo measurement in a subject utilizing dynamic light scattering (DLS) approach. The effect of DLS are utilized for the measurement of variety of blood related parameters, such as viscosity of the blood and blood plasma, blood flow, arterial blood pressure and other blood chemistry and rheology related parameters. DLS is a well-established technique to provide data on the size and shape of particles from temporal speckle analysis. When a coherent light beam (laser beam, for example) is incident on a scattering (rough) surface, a time-dependent fluctuation in the scattering property of the surface and thus in the scattering intensity (transmission and/or reflection) from the surface is observed. These fluctuations are due to the fact that the particles are undergoing Brownian or regular flow motion as a result of non-uniform blood flow (i.e. manifested in blood-shear) and so the distance between the particles is constantly changing with time. This scattered light then undergoes either constructive or destructive interference by the surrounding particles and within this intensity fluctuation information is contained about the time scale of movement of the particles. The scattered light is in the form of speckles pattern, being detected in the far diffraction zone. The detected signal is amplified and digitized for further analysis by using the autocorrelation function (ACF) technique. The technique is applicable either by heterodyne or by a homodyne DLS setup.

The kinetics of optical manifestations of two kinds of physiological signals is measured in vivo: the pulsatile signal associated with heart beats and the post-occlusion optical signal which is induced by an artificially generated blood flow cessation. The light transmission and/or reflection signals are used as a control of the physiological response. This kind of control measurement can be carried out simultaneously with the DLS reflection measurement. The mutual correspondence between DLS and standard optical signals is subject to a comparison analysis.

Reference is now made to FIGS. 3A-3B. FIG. 3A, taken from WO 2008/053474 (and slightly modified) illustrates an apparatus for performing a DLS measurement. A coherent light source (e.g. a vertical-cavity surface-emitting laser (VCSEL)) emits coherent light to illuminate the skin (step S201)—this coherent light scatters off of red blood cells (RBCs) within blood vessels of the skin (or beneath the skin) to induce a scattered-light optical response The optical response is detected (step S205) by photodetectors to generate an electrical signal descriptive of the scattered-light optical response (see FIG. 4 of WO 2008/053474). Scattered-light-optical-response-descriptive electrical signal (i.e. one example is in FIG. 4 of WO 2008/053474; another example is the signal A(t) passed from analog electronics assembly 270 to digitizer 204 of the FIG. 2 of WO2012064326)) is processed (e.g. using autocorrelation or power spectrum analysis) (step S213) to produce a time-dependent blood-shear-rate descriptive signal or BSRD. Examples of a BSRD are illustrated in FIGS. 9-13 of WO 2008/053474). One or more physiological parameter(s) (e.g. pulse rate or blood pressure) are computed from the BSRD signal.

It is noted that red blood cells (RBSs) suspended within blood plasma do not travel at the same velocity—instead, there is a velocity distribution. The BSRD signal describes differences in velocities of red-blood-cells suspended in the blood plasma. In certain frequency domains, blood-shear is primarily due to pulse. By illuminating skin, collecting scattered light and subjecting the scattered light to speckle analysis (e.g. to analyze temporal fluctuations of speckle patterns), it is possible to derive a signal descriptive of a blood-shear over a cross section of blood vessel(s) and/or over a ensemble of blood vessels.

FIG. 4, taken from WO 2008/053474, illustrates one example of a scattered-light time-dependent optical response signal generated in step S205.

FIG. 5A illustrates one example of a time-dependent blood-shear-rate descriptive signal. FIG. 5B illustrates another example of a time-dependent blood-shear-rate descriptive signal.

Although both the signals of FIG. 5A-5B are optically and electronically generated according to steps S201-213 of FIG. 3B, there is a fundamental difference—the example of FIG. 5A is generated by computing a power spectrum integral of the optical response signal (i.e. generated in step S205) over the frequency interval [2700 Hz, 10,000 Hz]

while the example of FIG. 5B is generated by computing a power spectrum integral of the optical response signal (i.e. generated in step S205) over the frequency interval [0 Hz, 548 Hz].

Inspection of FIGS. 5A and 5B shows that the blood-shear-rate descriptive signal follows that of a pulse-wave, while that of FIG. 5B does not. Thus, the BSRD (shear-rate-descriptive) signal of FIG. 5A is 'pulsatile' while that of FIG. 5B is not. The DLS spectral response will be a superposition of responses of different components across the blood vessels radius, according to the shear rate at each specific point.

When generating the signal of FIG. 5A the frequency-selection profile [2700 Hz, 10000 Hz] is employed in step S213 and the result is the pulsatile signal illustrated in FIG. 5A. In contrast, when generating the signal of FIG. 5B the frequency-selection profile [0 Hz, 548 Hz] is employed in step S213 and the result is the non-pulsatile signal illustrated in FIG. 5B.

FIG. 6A is a flow diagram for the device and method of WO 2008/053474. The illumination signal of FIG. 6A is generated in step S201 of FIG. 3B. Light of the illumination signal is reflected and/or transmitted and/or deflected by red blood cells within an 'ensemble' of blood vessels' (illustrated in FIG. 6A) to module the signal into a light response signal. The light response signal is received by photodetector(s) in step S205 of FIG. 3B to generate the response-descriptive electrical signal (illustrated in FIG. 6A).

FIG. 6B relates to the method and device of WO2012064326 where first and second photodetectors (e.g. at respective locations Loc_1, Loc_2) respectively receive the light response signal to generate respective response-descriptive electrical signals specific to the respective locations Loc_1, Loc_2). These signals are processed by analog electronic circuitry to generate yet another response-descriptive electrical signal.

As discussed in WO2012064326, there are number of differences between (i) the 'input' response-descriptive electrical signals (i.e. 'first' and 'second' signals) that are input to the subtraction analog circuitry and (ii) the output response-descriptive electrical signals—e.g. the AC component of the output signal has a much stronger contribution than in the input signals, the stochastic component of the output signal has a much stronger contribution than in the input signals.

FIG. 7A illustrates an example of a configuration for performing the method of FIG. 3B-FIG. 7B is one example of the subtraction analog circuitry of FIG. 6B.

The output of FIGS. 6A, 6B is responsive descriptive electrical signal. FIG. 8 relate to both WO 2008/053474 and WO2012064326 and is a data-flow diagram describing the processing of any response-descriptive electrical signal (e.g. that of FIG. 6A or the any response-descriptive electrical signal of FIG. 6B) is processed. Thus, BSRD signal is generated by a 'BSRD' generator 190 (e.g. implemented in any combination of analog and/or digital hardware and/or software) according to a pulsatile frequency-selection profile—e.g the profile [2700 Hz, 10000 Hz] of FIG. 5A. A pulsatile frequency-selection profile generates a 'pulsatile' BSRD from a response-descriptive electrical signal. This pulsatile signal is then analyzed by a second signal processor 194 (i.e. once again, implemented in any combination of analog and/or digital hardware and/or software) which analyzes features of the pulse-wave within the BSRD—e.g. to generate a pulse signal or a heart rate variability signal.

Measuring and/or Classifying Stress, Stress Resistance and Mood

Wikipedia defines stress as follows:

Physiological or biological stress is an organism's response to a stressor such as an environmental condition or a stimulus. Stress is a body's method of reacting to a challenge. According to the stressful event, the body's way to respond to stress is by sympathetic nervous system activation which results in the fight-or-flight response. Because the body cannot keep this state for long periods of time, the parasympathetic system returns the body's physiological conditions to normal (homeostasis). In humans, stress typically describes a negative condition or a positive condition that can have an impact on a person's mental and physical well-being.

Stress may be categorized as (i) physical stress or (ii) non-physical stress—e.g. mental stress or emotional stress. Physical stress may be brought about by the subject's exerting him/herself. Non-physical stress includes emotional stress and mental stress. For example, unpleasant noises, unhappy thoughts, unpleasant visual images may trigger emotional stress—unpleasant noises, thoughts and visual images are examples of 'stressors'. Mental exertion such as attempting to solve difficult arithmetic or to resolve cognitive interference (e.g. taking a 'Stroop test' named after John Ridley Stroop, author of the 1935 article entitled "Studies of interference in serial verbal reactions"). Thus, mental exertion is a stressor that induces mental stress.

Stress may also be distinguished from 'stress resistance' which is a function of temperament. Thus, there are some individuals where even a slight 'stressor' (e.g. an unpleasant noise at a very low volume) induces significant stress—they may be considered 'high-strung' or 'stress prone.' In contrast, other individuals may exhibit a stronger resistance to stress, and may require a more significant 'stressor' in order to exhibit a stress-state. Some individuals may exhibit a strong resistance to certain types of stress and much less resistance to other types of stress.

Pulsatile Measurement of Stress, Mood and Related Parameters

It is known in the art to employ heart-rate (or derived parameters such as heart rate variability—HRV) as a 'classifier' for detecting emotional episodes or stress episodes. For example, if a person is very excited or angry, his/her pulse rate will increase relative to a 'baseline.'

However, it is also known that heart rate by itself can be a 'poor classifier' (i.e. by itself) for (i) detecting emotional or stress episodes and/or (ii) for classifying emotional or stress episodes. In a first example, a person's heart rate and HRV may increase for any number of reasons, including but not limited natural variations, performance of physical exercise and weather conditions. Thus, in this example relying exclusively on heart-rate may lead to a large number of 'false positives' erroneously indicating an emotional or stress episode.

In another example, both anger and intense happiness/excitement may increase a subject's heart-rate. Simply relying on elevated heart rate is inadequate for differentiating between two different types of emotional/mood episodes (i.e. anger and intense happiness).

Although pulsatile-derived classifiers may certainly be useful, and have there place, there is a need for accurate non-pulsatile techniques for detecting stress or emotional episodes.

SUMMARY

Embodiments of the present invention relate to a method and apparatus for hemodynamically characterizing a neurological or fitness state by dynamic light scattering (DLS)—e.g. by measuring fluctuations (i.e. shear of) in skin blood flow.

In contrast with previously-disclosed DLS-based techniques that rely on analyzing a pulsatile signal (or that are limited to occluded blood), presently-disclosed techniques relate to computing a non-pulsatile blood-shear-rate-descriptive (BSRD) signal(s).

A method and apparatus for hemodynamically characterizing a neurological or fitness state by dynamic scattering light (DLS) is disclosed herein. In particular, a non-pulsatile blood-shear-rate-descriptive (BSRD) signal(s) is optically generated and analyzed. In some embodiments, the BSRD signal is generated dynamically so as to adaptively maximize (i.e. according to a bandpass or frequency-selection profile) a prominence of a predetermined non-pulsatile physiological signal within the BSRD. In some embodiments, the BSRD is subjected to a stochastic or stationary-status analysis. Alternatively or additionally, the neurological or fitness state may be computed from multiple BSRDs, including two or more of: (i) a [sub −200 Hz, ~300 Hz] BSRD signal; (ii) a [~300 Hz, ~1000 Hz] signal; (iii) a [~1000 Hz, ~4000 Hz] signal and (iv) a [~4000 Hz, z Hz] (z>=7,000) signal.

Some embodiments relate to a method for optically measuring state and/or status information or changes therein about a warm-blooded subject, the method including: a. illuminating a portion of the subject's skin or tissue by a vcsel (vertical cavity surface emitting laser) or a diode laser to scatter partially or entirely coherent light off of the subject's moving red blood cells (rbcs) to induce a scattered-light time-dependent optical response; b. receiving the scattered light by a photodetector(s) to generate an electrical signal descriptive of the induced scattered-light time-dependent optical response; c. processing the scattered-light-optical-response-descriptive electrical signal or a derived-signal thereof to compute therefrom one or more blood-shear-rate-descriptive (bsrd) signal(s), each bsrd signal characterized by a respective frequency-selection profile; d. electronically analyzing features of the bsrd signal(s) of the bsrd signal group; e. in accordance with the results of the electronically analyzing of the frequency-interval-specific shear-rate-descriptive signal(s), computing the state and/or status information or changes therein from the results of the analyzing; where. The method also includes a frequency-selection profile of the bsrd(s) signal is computed dynamically so as to adaptively maximize a prominence of a predetermined non-pulsatile physiological signal within the bsrd(s); and/or. The method also includes computation of the state and/or status information is performed dynamically so that a weight assigned to a bsrd signal is adaptively determined to increase a weight of bsrd signal(s) whose frequency-selection profile correspond to a greater prominence of the predetermined non-pulsatile physiological signal at the weight-expense of bsrd signal(s) whose frequency-selection profile correspond to a lesser prominence of the predetermined non-pulsatile physiological signal. Other embodiments of this aspect include corresponding computer systems, apparatus, and computer programs recorded on one or more computer storage devices, each configured to perform the actions of the methods.

Implementations may include one or more of the following features. The method where the measured state is a neurological state. The method any −4 where the predetermined non-pulsatile physiological signal is a mayer wave signal. The method of any −8 where a prominence of the predetermined non-pulsatile physiological signal is computed and the state and/or status information is determined from the results of the computing of a prominence of the predetermined non-pulsatile physiological signal. In some embodiments, where the non-pulsatile bsrd signal(s) is subjected to a stochastic analysis or to a stationary-status analysis that quantifies a stationary/non-stationary status of the bsrd signal(s) and the state and/or status information or changes therein is computed from the results of the stochastic and/or stationary-status analysis. In some embodiments, 20 where: i. a pulsatile bsrd signal(s) is also generated from the scattered-light-optical-response-descriptive electrical signal or derived signal thereof, ii. subject-status-classification operation(s) is performed according to both feature(s) of the pulsatile bsrd signal(s) and the results of the stochastic and/or stationary-status analysis of the non-pulsatile bsrd signal(s), iii. the pulsatile bsrd signal(s) is rated according to a prominence of blood-pressure-waveform feature(s) therein, and iv. the non-pulsatile bsrd signal(s) is dynamically computed such that the frequency-selection profile thereof is dynamically adjusted. The method any −4 where the predetermined non-pulsatile physiological signal is a neurogenic signal. The method of any −4 where the predetermined non-pulsatile physiological signal is a myogenic signal. The method any −4 where the predetermined non-pulsatile physiological signal is a respiratory signal. The method any −4 where the predetermined non-pulsatile physiological signal is a periodic/oscillator signal. The method where the measured state is a fitness state. The method where state and/or status information includes at least one of: a stress-state, a cardiovascular-fitness, a pain-state, a fatigue-state, a stress-resistance, a diurnal fluctuation of stress or stress-resistance, and an apnea event. The method of any −19 where the method is performed adaptively such that: i. one or more non-pulsatile candidate bsrd signal(s) are scored so that (a) a greater signal energy and a lower pulsatile signal-contribution increase a quality-score of a rated non-pulsatile candidate bsrd signal and (b) conversely, a lower signal energy and a greater pulsatile signal-contribution decrease a quality-score of a rated non-pulsatile candidate bsrd signal; and ii. the subject-status-classification operation is performed dynamically so as to assign greater weight to candidate bsrd signal(s) having a higher score and to assign a lower weight to candidate bsrd signal(s) having a lower score. The method where the measured state is a neurological state. The method where the measured state is a fitness state. The method where state and/or status information includes at least one of: a stress-state, a cardiovascular-fitness, a pain-state, a fatigue-state, a stress-resistance, a diurnal fluctuation of stress or stress-resistance, and an apnea event. The method where the stochastic and/or stationary-status analysis includes computing at least one of: a fractal dimension of the bsrd signal(s), an entropy of the bsrd signal(s) and a hurst component of the bsrd signal(s). The method where the stochastic and/or stationary-status analysis includes computing at least one of: a fractal dimension of the bsrd signal(s), an entropy of the bsrd signal(s) and a hurst component of the bsrd signal(s). The method where non-pulsatile bsrd signal(s) are dynamically computed such that the frequency-selection profile thereof is dynamically adjusted so as to maximize a signal energy while minimizing a residual-pulse component of the bsrd signal(s). The method where the measured state is a neurological state. The method where the measured state is a fitness state. The method where state and/or status information includes at least one of: a stress-state, a cardiovascular-fitness, a pain-state, a fatigue-state, a stress-resistance, a diurnal fluctuation of stress or stress-resistance, and an apnea event. Implementations of the described techniques may include hardware, a method or process, or computer software on a computer-accessible medium.

One aspect includes a method for optically measuring state and/or status information or changes therein about a warm-blooded subject, the method including: a. illuminating a portion of the subject's skin or tissue by a vcsel (vertical cavity surface emitting laser) or a diode laser to scatter partially or entirely coherent light off of the subject's moving red blood cells (rbcs) to induce a scattered-light time-dependent optical response; b. receiving the scattered light by a photodetector(s) to generate an electrical signal descriptive of the induced scattered-light time-dependent optical response; c. processing the scattered-light-optical-response-descriptive electrical signal or a derived-signal thereof to compute therefrom one or more blood-shear-rate-descriptive (bsrd) signal(s), each bsrd signal characterized by a respective frequency-selection profile; d. electronically analyzing features of the bsrd signal(s) of the bsrd signal group to quantify a prominence of a physiological signal within the bsrd, the bsrd being selected from the group including of a mayer wave, a neurogenic signal and a myogenic; and e. computing, from the results of the quantifying of the prominence, the state and/or status information or changes therein. Other embodiments of this aspect include corresponding computer systems, apparatus, and computer programs recorded on one or more computer storage devices, each configured to perform the actions of the methods.

Implementations may include one or more of the following features. The method where the measured state is a neurological state. The method where the measured state is a fitness state. The method where state and/or status information includes at least one of: a stress-state, a cardiovascular-fitness, a pain-state, a fatigue-state, a stress-resistance, a diurnal fluctuation of stress or stress-resistance, and an apnea event. The method where the stochastic and/or stationary-status analysis includes computing at least one of: a fractal dimension of the bsrd signal(s), an entropy of the bsrd signal(s) and a hurst component of the bsrd signal(s). The method where the stochastic and/or stationary-status analysis includes computing at least one of: a fractal dimension of the bsrd signal(s), an entropy of the bsrd signal(s) and a hurst component of the bsrd signal(s). The method where non-pulsatile bsrd signal(s) are dynamically computed such that the frequency-selection profile thereof is dynamically adjusted so as to maximize a signal energy while minimizing a residual-pulse component of the bsrd signal(s). The method where the measured state is a neurological state. The method where the measured state is a fitness state. The method where state and/or status information includes at least one of: a stress-state, a cardiovascular-fitness, a pain-state, a fatigue-state, a stress-resistance, a diurnal fluctuation of stress or stress-resistance, and an apnea event. Implementations of the described techniques may include hardware, a method or process, or computer software on a computer-accessible medium.

One aspect includes a method for optically measuring state and/or status information or changes therein about a warm-blooded subject, the method including: a. illuminating a portion of the subject's skin or tissue by a vcsel (vertical cavity surface emitting laser) or a diode laser to scatter partially or entirely coherent light off of the subject's moving red blood cells (rbcs) to induce a scattered-light time-dependent optical response; b. receiving the scattered light by a photodetector(s) to generate an electrical signal descriptive of the induced scattered-light time-dependent optical response c. processing the scattered-light-optical-response-descriptive electrical signal or a derived-signal thereof to compute therefrom a non-pulsatile blood-shear-rate-descriptive (bsrd) signal(s), each bsrd signal characterized by a respective frequency-selection profile; d. subjecting the non-pulsatile bsrd signal(s) to a stochastic analysis or to a stationary-status analysis that quantifies a stationary/non-stationary status of the bsrd signal(s); e. computing the state and/or status information or changes therein from the results of the stochastic and/or stationary-status analysis. Other embodiments of this aspect include corresponding computer systems, apparatus, and computer programs recorded on one or more computer storage devices, each configured to perform the actions of the methods.

Implementations may include one or more of the following features. The method where the stochastic and/or stationary-status analysis includes computing at least one of: a fractal dimension of the bsrd signal(s), an entropy of the bsrd signal(s) and a hurst component of the bsrd signal(s). The method where the stochastic and/or stationary-status analysis includes computing at least one of: a fractal dimension of the bsrd signal(s), an entropy of the bsrd signal(s) and a hurst component of the bsrd signal(s). The method where non-pulsatile bsrd signal(s) are dynamically computed such that the frequency-selection profile thereof is dynamically adjusted so as to maximize a signal energy while minimizing a residual-pulse component of the bsrd signal(s). The method where the measured state is a neurological state. The method where the measured state is a fitness state. The method where state and/or status information includes at least one of: a stress-state, a cardiovascular-fitness, a pain-state, a fatigue-state, a stress-resistance, a diurnal fluctuation of stress or stress-resistance, and an apnea event. Implementations of the described techniques may include hardware, a method or process, or computer software on a computer-accessible medium.

One aspect includes a method for optically measuring state and/or status information or changes therein about a warm-blooded subject, the method including: a. illuminating a portion of the subject's skin or tissue by a vcsel (vertical cavity surface emitting laser) or a diode laser to scatter partially or entirely coherent light off of the subject's moving red blood cells (rbcs) to induce a scattered-light time-dependent optical response; b. receiving the scattered light by a photodetector(s) to generate an electrical signal descriptive of the induced scattered-light time-dependent optical response or an ac component thereof; c. processing the scattered-light-optical-response-descriptive electrical signal or a derived-signal thereof to compute therefrom at least two or at least three or at least four blood-shear-rate-descriptive (bsrd) signals selected from the bsrd signal group, each blood-rate-descriptive bsrd signal characterized by a different respective frequency-selection profile, the bsrd signal group including of the following signals: (i) a [sub −200 hz, ~300 hz] bsrd signal; (ii) a [~300 hz, ~1000 hz] bsrd signal; (iii) a [~1000 hz, ~4000 hz] bsrd signal and (iv) a [~4000 hz, z hz] (z>=7,000) bsrd signal; d. electronically analyzing features of the at least two or at least 3 or at least 4 bsrd signals of the bsrd signal group; e. in accordance with the results of the electronically analyzing of the at least two or at least 3 or at least 4 bsrd signals, computing the state and/or status information or changes therein. Other embodiments of this aspect include corresponding computer systems, apparatus, and computer programs recorded on one or more computer storage devices, each configured to perform the actions of the methods.

Implementations may include one or more of the following features. The method where the measured state is a neurological state. The method where the measured state is a fitness state. The method where state and/or status information includes at least one of: a stress-state, a cardiovascular-fitness, a pain-state, a fatigue-state, a stress-resistance, a diurnal fluctuation of stress or stress-resistance, and an apnea event. Implementations of the described techniques may include hardware, a method or process, or computer software on a computer-accessible medium.

One aspect includes the method of any −25 where at least one of the non-pulsatile bsrd signal(s) is subjected to a stochastic analysis or to a stationary-status analysis that quantifies a stationary/non-stationary status of the bsrd signal(s) and the state and/or status information or changes therein is computed from the results of the stochastic and/or stationary-status analysis. Other embodiments of this aspect include corresponding computer systems, apparatus, and computer programs recorded on one or more computer storage devices, each configured to perform the actions of the methods.

In some embodiments, the method is performed adaptively such that: i. one or more non-pulsatile candidate bsrd signal(s) are scored so that (a) a greater signal energy and a lower pulsatile signal-contribution increase a quality-score of a rated non-pulsatile candidate bsrd signal and (b) conversely, a lower signal energy and a greater pulsatile signal-contribution decrease a quality-score of a rated non-pulsatile candidate bsrd signal; and ii. the subject-status-classification operation is performed dynamically so as to assign greater weight to candidate bsrd signal(s) having a higher score and to assign a lower weight to candidate bsrd signal(s) having a lower score. Other embodiments of this aspect include corresponding computer systems, apparatus, and computer programs recorded on one or more computer storage devices, each configured to perform the actions of the methods.

Implementations may include one or more of the following features. In some embodiments, where: i. a pulsatile bsrd signal(s) is also generated from the scattered-light-optical-response-descriptive electrical signal or derived signal thereof, ii. subject-status-classification operation(s) is performed according to both feature(s) of the pulsatile bsrd signal(s) and the results of the stochastic and/or stationary-status analysis of the non-pulsatile bsrd signal(s), iii. the pulsatile bsrd signal(s) is rated according to a prominence of blood-pressure-waveform feature(s) therein, and iv. the non-pulsatile bsrd signal(s) is dynamically computed such that the frequency-selection profile thereof is dynamically adjusted. In some embodiments, where the measuring includes classifying a stress-state so as to distinguish between any two of mental-stress, emotional-stress and/or determining if a dominant stress mode of the subject is physical, emotional or mental. In some embodiments, further including according to the subject-status-classification operation, (i) triggering at least one of an alert and therapy and/or (ii) serving advertisement to a user and/or (iii) updating the subject's user-profile and/or (iv) adjusting display-parameter(s) of a gui operated by the user, where at least one of step(s) c-e is/are performed using a processor. In some embodiments, where the processing of the scattered-light-optical-response-descriptive electrical signal or derived signal thereof to compute bsrd signal(s) is performed by an application-specific integrated circuit (asic) and/or by a circuit (e.g. integrated circuit) in which the frequency-selection-profile is hardwired into the circuit and/or performed by a digital signal processor (dsp) (e.g. executing firmware). The method where a plurality of bsrd-specific circuits are employed, each one associated with a different respective frequency-profile. In some embodiments, where state and/or status information includes at least one of: a stress-state, a cardiovascular-fitness, a pain-state, a fatigue-state, a stress-resistance, a diurnal fluctuation of stress or stress-resistance, and an apnea event. The method where the stress state is a dominant stress mode of the subject, for example mental vs. emotional. In some embodiments, where the fitness status described an orthostatic physical-stress. In some embodiments, performed on non-occluded free-flowing blood. The method where the stress state describes a magnitude of current-stress of the subject. The method where the dynamic weighing of multiple bsrds against each other is performed by execution (e.g. by a —purpose processor and/or microprocessor) of software such that dynamic-weighing code is present in software. The method of any claim 30 where the classifying of a stress-state includes. The method may also include distinguishing between any two of mental-stress, emotional-stress and/or determining if a dominant stress mode of the subject is physical, emotional or mental. The method where the classifying of a stress-state includes quantifying an extent of stress and/or the classifying of the stress-resistance includes classifying a stress-resistance-level of the subject. Implementations of the described techniques may include hardware, a method or process, or computer software on a computer-accessible medium.

One aspect includes a machine-learning-based method for optically obtaining state and/or status information or changes therein about a warm-blooded subject, the method including: a. monitoring behavior patterns of the subject by camera and/or receiving data via a graphical-user-interface and/or monitoring interactions of the user with advertisement(s) and/or according to audio output of the user; b. illuminating a portion of the subject's skin or tissue by a vcsel (vertical cavity surface emitting laser) or a diode laser to scatter partially or entirely coherent light off of the subject's moving red blood cells (rbcs) to induce a scattered-light time-dependent optical response; c. receiving the scattered light by a photodetector(s) to generate an electrical signal descriptive of the induced scattered-light time-dependent optical response d. processing the scattered-light-optical-response-descriptive electrical signal or a derived-signal thereof to compute therefrom one or more blood-shear-rate-descriptive (bsrd) signal(s), each bsrd signal characterized by a respective frequency-selection profile; e. in accordance with a correlation between (i) a result of the monitoring of the subject's behavior patterns of step (a) and (ii) feature(s) of the bsrd signal(s), training a subject-status-classifier capable of classifying a subject-status, in accordance with bsrd-signal-derived input, at least one a stress-state (e.g. type of stress or level of stress) a mood-state, a stress-resistance, and a cardiovascular fitness-status of the subject; and f. at a later time, employing the trained classifier to compute, from the bsrd signal(s), state and/or status information or changes therein. Other embodiments of this aspect include corresponding computer systems, apparatus, and computer programs recorded on one or more computer storage devices, each configured to perform the actions of the methods.

Implementations may include one or more of the following features. The method of any claim 30 where the classifying of a stress-state includes. The method may also include distinguishing between any two of mental-stress, emotional-stress and/or determining if a dominant stress mode of the subject is physical, emotional or mental. The method where the classifying of a stress-state includes quantifying an extent of stress and/or the classifying of the stress-resistance includes classifying a stress-resistance-level of the subject.

Implementations of the described techniques may include hardware, a method or process, or computer software on a computer-accessible medium.

One aspect includes apparatus for optically measuring state and/or status information or changes therein about a warm-blooded subject the apparatus including: a. a diode laser or vcsel configured to illuminate the subject's skin so as to scatter partially or entirely coherent light off of moving red blood cells (rbcs) of the subject to induce a scattered-light time-dependent optical response; b. photodetector(s) configured to generate an electrical signal descriptive of the induced scattered-light time-dependent optical response; and c. electronic circuitry configured to: i. process the scattered-light-optical-response-descriptive electrical signal or a derived-signal thereof to compute therefrom one or more blood-shear rate-descriptive (bsrd) signal(s), each bsrd signal characterized by a respective frequency-selection profile; ii. electronically analyze features of the bsrd signal(s) of the bsrd signal group; iii. in accordance with the results of the electronically analyzing of the at least two frequency-interval-specific shear-rate-descriptive signals, perform at least one of the following of subject-status-classification operation(s). The apparatus also includes classify a stress-state (e.g. type of stress or level of stress) of the subject. The apparatus also includes classify a mood-state of the subject. The apparatus also includes classify a stress-resistance of the subject. The apparatus also includes classify a cardiovascular fitness-status of the subject. The apparatus also includes where a frequency-selection profile of the bsrd(s) signal is computed. The apparatus also includes dynamically so to adaptively maximize a prominence of a predetermined. The apparatus also includes non-pulsatile physiological signal within the bsrd(s) and/or where the. The apparatus also includes classification operation is performed dynamically so that a weight. The apparatus also includes assigned to a bsrd signal is adaptively determined to increase a weight. The apparatus also includes of bsrd signal(s) whose frequency-selection profile correspond to a. The apparatus also includes greater prominence of the predetermined non-pulsatile physiological. The apparatus also includes signal at the weight-expense of bsrd signal(s) whose frequency-selection. The apparatus also includes profile correspond to a lesser prominence of the predetermined non. The apparatus also includes pulsatile physiological signal. Other embodiments of this aspect include corresponding computer systems, apparatus, and computer programs recorded on one or more computer storage devices, each configured to perform the actions of the methods.

One aspect includes apparatus for optically measuring state and/or status information or changes therein about a warm-blooded subject the apparatus including: a. a diode laser or vcsel configured to illuminate the subject's skin so as to scatter partially or entirely coherent light off of moving red blood cells (rbcs) of the subject to induce a scattered-light time-dependent optical response, b. photodetector(s) configured to generate an electrical signal descriptive of the induced scattered-light time-dependent optical response, and c. electronic circuitry configured to perform the following. The apparatus also includes i. processing the scattered-light-optical-response-descriptive electrical signal or a derived-signal thereof to compute therefrom one or more blood-shear-rate-descriptive (bsrd) signal(s), each bsrd signal characterized by a respective frequency-selection profile. The apparatus also includes ii. electronically analyzing features of the bsrd signal(s) of the bsrd signal group. The apparatus also includes iii. in accordance with the results of the electronically analyzing of the frequency-interval-specific shear-rate-descriptive signal(s), computing the state and/or status information or changes therein from the results of the analyzing; where. The apparatus also includes a frequency-selection profile of the bsrd(s) signal is computed dynamically so as to adaptively maximize a prominence of a predetermined non-pulsatile physiological signal within the bsrd(s); and/or. The apparatus also includes computation of the state and/or status information is performed dynamically so that a weight assigned to a bsrd signal is adaptively determined to increase a weight of bsrd signal(s) whose frequency-selection profile correspond to a greater prominence of the predetermined non-pulsatile physiological signal at the weight-expense of bsrd signal(s) whose frequency-selection profile correspond to a lesser prominence of the predetermined non-pulsatile physiological signal. Other embodiments of this aspect include corresponding computer systems, apparatus, and computer programs recorded on one or more computer storage devices, each configured to perform the actions of the methods.

One aspect includes apparatus for optically measuring state and/or status information or changes therein about a warm-blooded subject the apparatus including: a. a diode laser or vcsel configured to illuminate the subject's skin so as to scatter partially or entirely coherent light off of moving red blood cells (rbcs) of the subject to induce a scattered-light time-dependent optical response, b. photodetector(s) configured to generate an electrical signal descriptive of the induced scattered-light time-dependent optical response, and c. electronic circuitry configured to perform the following. The apparatus also includes i. processing the scattered-light-optical-response-descriptive electrical signal or a derived-signal thereof to compute therefrom one or more blood-shear-rate-descriptive (bsrd) signal(s), each bsrd signal characterized by a respective frequency-selection profile. The apparatus also includes ii. electronically analyzing features of the bsrd signal(s) of the bsrd signal group to quantify a prominence of a physiological signal within the bsrd, the bsrd being selected from the group including of a mayer wave, a neurogenic signal and a myogenic. The apparatus also includes iii. computing, from the results of the quantifying of the prominence, the state and/or status information or changes therein. Other embodiments of this aspect include corresponding computer systems, apparatus, and computer programs recorded on one or more computer storage devices, each configured to perform the actions of the methods.

One aspect includes apparatus for optically measuring state and/or status information or changes therein about a warm-blooded subject the apparatus including: a. a diode laser or vcsel configured to illuminate the subject's skin so as to scatter partially or entirely coherent light off of moving red blood cells (rbcs) of the subject to induce a scattered-light time-dependent optical response, b. photodetector(s) configured to generate an electrical signal descriptive of the induced scattered-light time-dependent optical response, and c. electronic circuitry configured to perform the following. The apparatus also includes i. processing the scattered-light-optical-response-descriptive electrical signal or a derived-signal thereof to compute therefrom a non-pulsatile blood-shear-rate-descriptive (bsrd) signal(s), each bsrd signal characterized by a respective frequency-selection profile. The apparatus also includes ii. subjecting the non-pulsatile bsrd signal(s) to a stochastic analysis or to a stationary-status analysis that quantifies a stationary/non-stationary status of the bsrd signal(s). The apparatus also includes iii. computing the state and/or status information or changes therein from the results of the stochastic and/or stationary-status analysis.

Other embodiments of this aspect include corresponding computer systems, apparatus, and computer programs recorded on one or more computer storage devices, each configured to perform the actions of the methods.

One aspect includes apparatus for optically measuring state and/or status information or changes therein about a warm-blooded subject the apparatus including: a. a diode laser or vcsel configured to illuminate the subject's skin so as to scatter partially or entirely coherent light off of moving red blood cells (rbcs) of the subject to induce a scattered-light time-dependent optical response; b. photodetector(s) configured to generate an electrical signal descriptive of the induced scattered-light time-dependent optical response; and c. electronic circuitry configured to perform the following: i. processing the scattered-light-optical-response-descriptive electrical signal or a derived-signal thereof to compute therefrom at least two or at least three or at least four blood-shear-rate-descriptive (bsrd) signals selected from the bsrd signal group, each blood-rate-descriptive bsrd signal characterized by a different respective frequency-selection profile, the bsrd signal group including of the following signals: (i) a [sub –200 hz, ~300 hz] bsrd signal; (ii) a [~300 hz, ~1000 hz] bsrd signal; (iii) a [~1000 hz, ~4000 hz] bsrd signal and (iv) a [~4000 hz, z hz] (z>=7,000) bsrd signal; ii. electronically analyzing features of the at least two or at least 3 or at least 4 bsrd signals of the bsrd signal group; iii. in accordance with the results of the electronically analyzing of the at least two or at least 3 or at least 4 bsrd signals, computing the state and/or status information or changes therein. Other embodiments of this aspect include corresponding computer systems, apparatus, and computer programs recorded on one or more computer storage devices, each configured to perform the actions of the methods.

One aspect includes where the measured state is a neurological state. Other embodiments of this aspect include corresponding computer systems, apparatus, and computer programs recorded on one or more computer storage devices, each configured to perform the actions of the methods.

One aspect includes where the measured state is a fitness state. Other embodiments of this aspect include corresponding computer systems, apparatus, and computer programs recorded on one or more computer storage devices, each configured to perform the actions of the methods.

One aspect includes where state and/or status information includes at least one of: a stress-state, a cardiovascular-fitness, a pain-state, a fatigue-state, a stress-resistance, a diurnal fluctuation of stress or stress-resistance, and an apnea event. Other embodiments of this aspect include corresponding computer systems, apparatus, and computer programs recorded on one or more computer storage devices, each configured to perform the actions of the methods.

One aspect includes where the predetermined non-pulsatile physiological signal is a mayer wave signal. Other embodiments of this aspect include corresponding computer systems, apparatus, and computer programs recorded on one or more computer storage devices, each configured to perform the actions of the methods.

One aspect includes where the predetermined non-pulsatile physiological signal is a neurogenic signal. Other embodiments of this aspect include corresponding computer systems, apparatus, and computer programs recorded on one or more computer storage devices, each configured to perform the actions of the methods.

One aspect includes where the predetermined non-pulsatile physiological signal is a myogenic signal. Other embodiments of this aspect include corresponding computer systems, apparatus, and computer programs recorded on one or more computer storage devices, each configured to perform the actions of the methods.

One aspect includes where the predetermined non-pulsatile physiological signal is a respiratory signal. Other embodiments of this aspect include corresponding computer systems, apparatus, and computer programs recorded on one or more computer storage devices, each configured to perform the actions of the methods.

One aspect includes where the predetermined non-pulsatile physiological signal is a periodic/oscillator signal. Other embodiments of this aspect include corresponding computer systems, apparatus, and computer programs recorded on one or more computer storage devices, each configured to perform the actions of the methods.

BRIEF DESCRIPTION OF THE DRAWINGS

FIGS. 10, 12A-12B, 16-17, 18A-18C, 22A, 23-24 are flow charts of presently disclosed methods according to some embodiments.

FIGS. 11A-11B, 13, 19, 20A-20B, 21A-21B, 26A-26H, 26I-26L, 27A-27D, 28A-28D, 29A-29D, 30A-30D show data and/or results according to some embodiments.

DETAILED DESCRIPTION OF EMBODIMENTS

Figure 1A:
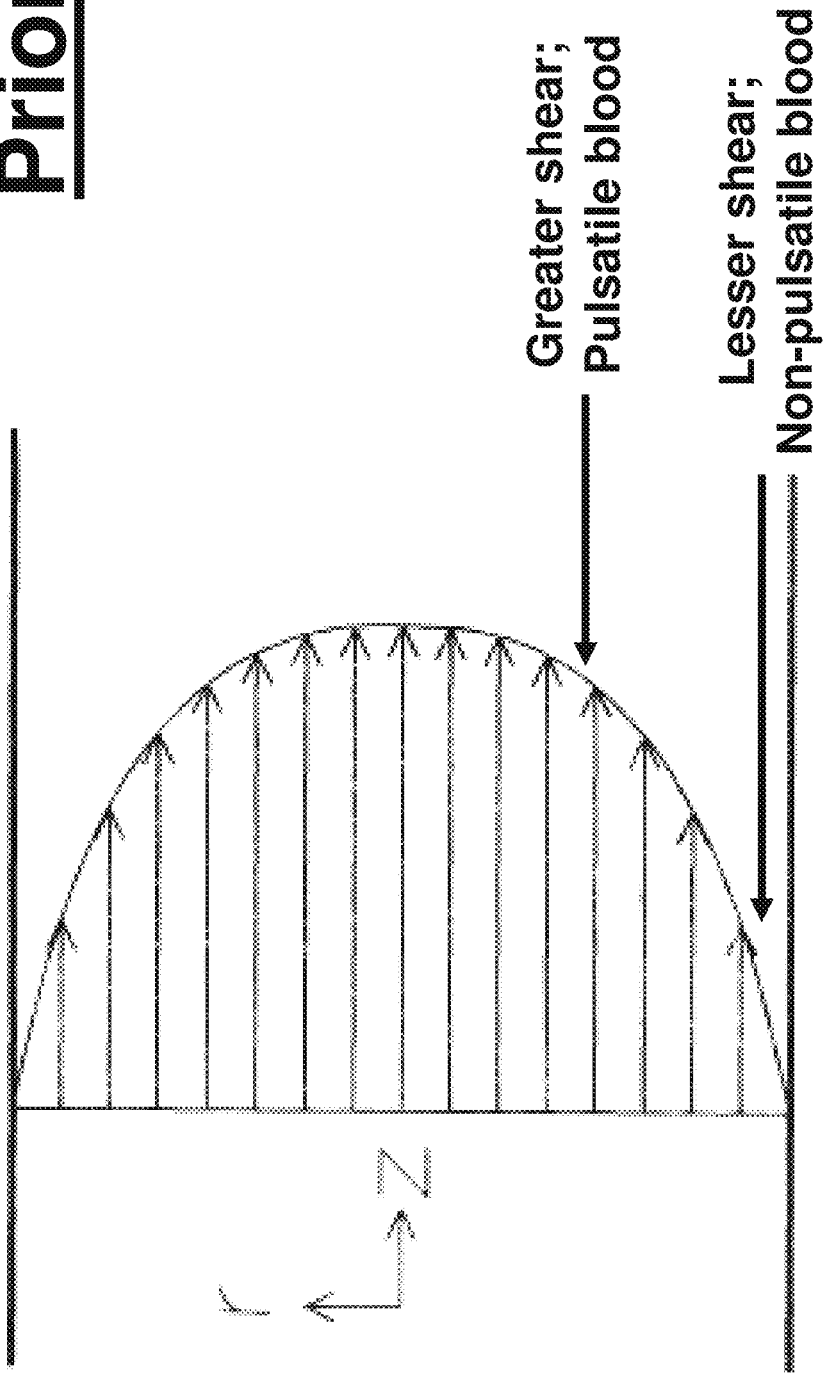
FIGS. 1A-1B schematically illustrate blood flow within a blood vessel.

The invention is herein described, by way of example only, with reference to the accompanying drawings. With specific reference now to the drawings in detail, it is stressed that the particulars shown are by way of example and for purposes of illustrative discussion of the preferred embodiments of the exemplary system only and are presented in the cause of providing what is believed to be a useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how several forms of the invention may be embodied in practice and how to make and use the embodiments.

For brevity, some explicit combinations of various features are not explicitly illustrated in the figures and/or described. It is now disclosed that any combination of the method or device features disclosed herein can be combined in any manner—including any combination of features—and any combination of features can be included in any embodiment and/or omitted from any embodiments.

Embodiments of the present invention relate to apparatus and method for optically detecting stress and/or mood and/or emotion and/or fitness and/or stress-resistance of a warm-blooded (e.g. mammalian or bird—in some preferred embodiments, the warm-blooded subject is a human subject) subject based on dynamic light scattering of red blood cells (RBSs) moving in the vessels.

In the prior art, dynamic light scattering has been used to generate a pulsatile Blood Shear Rate Descriptive signal (BSRD) and to compute therefrom pulse rate and blood pressure. The pulse signal is a known indicator of emotion, stress and fitness.

Yet, specifically by relating to filtering out the pulsatile signal as 'noise' (and/or by employing an appropriate non-pulsatile filter-selection profile for BSRD(s) generation to generate a non-pulsatile BSRD) is it possible to improve the accuracy and/or reduce the noise when detecting of emotion, stress and/or fitness/A non-pulsatile BSRD may be generated from the response-descriptive-electrical signal (or a derivative thereof) using the appropriate frequency-selection profile—e.g. for example, [a Hz, b Hz] where b>a e.g. b at most 1000 or at most 950 or at most 900 or at most 800 or at most 700 or at most 600 or at most 500 or at most 400 or at most 350 or at most 300). Alternatively or additionally, pulsatile component(s) of a pulsatile BSRD may be substantially removed (e.g. using a band-pass filter that filters out frequencies having significant pulsatile components) therefrom to generate the non-pulsatile BSRD which may be analyzed in the absence of the 'distracting' 'noise' pulsatile components. Thus, even though it is recognized that the pulse signal form (FIG. 2B) may include data about stress or other related indication (e.g. when someone is nervous his/her pulse increases), in some embodiments instead of relating to the pulsatile components of the BSRD as 'signal' it is more appropriate to strip them off as 'noise.'

In different embodiments, one or more (i.e. any combination) of the following feature(s) is provided:

A. Dynamic operation-mode—a BSRD (e.g. non-pulsatile BSRD) is dynamically generated using a 'dynamic frequency selection profile' updated in response to a prominence of feature(s) of certain physiological signals—for example, to dynamically-updated maximize a predicted or prominence of the physiological signal(s) within the BSRD—in some embodiments, see, for example, FIGS. 12-14, 17, 23-25);

B. Stochastic analysis of non-pulsatile BSRD(s)—non-pulsatile BSRD(s) (e.g. non-pulsatile BSRD) is generated and analyzed (e.g. subjected to stochastic analysis), and the detection of stress and/or mood and/or emotion and/or fitness is performed in accordance with the results of the analysis (see FIG. 18A-18C);

C. Weighing (e.g. dynamic weighing) of multiple types of BSRD(s) multiple types of BSRD(s) are generated (e.g. comprising at least one non-pulsatile BSRD) each one associated with a respective type of frequency selection profile. In some embodiments, when detecting stress and/or mood and/or emotion and/or fitness or a warm-blooded (e.g. mammalian) subject to 'classify' the subject's status, a dynamic weighing may be assigned to each type of BSRD—the relative weights may depend on (and be updated in response to changes in) the specifics of the mammalian subject or measurement conditions or on any other factor. Alternatively or additionally, one or more frequency selection profile(s) for generating a BSRD may be dynamically selected. (see FIGS. 22-25);

D. a machine-learning technique for better sensor accuracy—In some embodiments, it is possible to 'eavesdrop' on the subject's behavior by both (i) DLS dynamic light scattering techniques where a BSRD is generated upon scattering light from the subject's red blood cells at specific times and (ii) non-DLS data descriptive of the subject's instant stress-state or mood state at these specific times. A BSRD-feature-based mood-state-classifier or stress-state-classifier may be trained or updated according to the relation between the DLS data and the stress-state or mood-state descriptive non-DLS data. For example, BSRD-feature-based mood-state-classifier or stress-state-classifier may be trained so as to determine optimal frequency-selection profiles (i.e. for BSRD generation) and/or to determine optimal weights between multiple BSRD signals that optimize prediction stress-state or mood-state prediction accuracy One example of non-DLS data explicitly (or implicitly) descriptive of user mood or stress-state include is GUI-input data generated by human interaction with a graphical user interface (GUI)—for example, via a touch-screen or keyboard or mouse by an 'observing camera.' In a first use-case, a user is using a personalized music-listening application (e.g. local or cloud-based) where a user selects song from a 'bank' of songs to which to listen. In this use-case, it may be possible to 'eavesdrop' on the user's music-selections—if the user selects a 'sad' song this might be indicative that the user is feeling 'sad'—at this time, it may be possible to use this as calibration data for future DLS-based mood detection by generating BSRD signal(s) and computing features thereof.

In a second use-case, it is possible to eavesdrop on a user's voice (e.g. spoken speech) or typed output (i.e. text input to a digital computer—e.g. via a keyboard) and to derive therefrom mood-status or stress-status data about the subject. This may be derived according to the language content—for example, the user types 'I am happy.' In another example, a subject's instant stress or mood-status may be computed according to biometric data (e.g. voice-print data or biometric typing patterns).

Other non-DLS techniques for gathering data about the subject's instant mood-state or stress-state include but are not limited to: (i) capturing (e.g. by camera) or receiving digital images of the subject's facial expressions—it is possible using image-processing techniques to compute the subject's stress-state or mood-state from an image of his/her face; (ii) eavesdropping on user interaction with a GUI—for example, if songs or advertisements are sent to a user and the user 'skips' certain songs (or elects to listen to them) this indicates the user's instant mood-state or stress-state.

Non-DLS data about the user's mood-state or stress-state may be employed to train a DLS-based classifier so that a later time (e.g. when the non-DLS data is not available), the trained DLS classifier may be employed to accurately sense the subject's mood-state or stress-state.

During training of a DLS/BSRD-based mood-state or stress-state classifier, one or more of the following parameter(s) (the list below is not intended as comprehensive) of the stress/mood classifier may be optimized so as to maximize a prediction power of the DLS/BSRD-based mood-state or stress-state classifier: (i) a frequency profile for BSRD generation; (ii) a weighing function for relative weight BSRD(s) where each BSRD has its own respective frequency-selection parameter.

E. Response (e.g. treatment to reduce stress and/or improve mood)—in response to a detection of an elevated stress or to a 'poor mood' a number of measures may be taken including but not limited to: (i) subjecting the mammalian subject to 'relaxing' images or lighting or sound (e.g. music or sound)—e.g. on a display screen or via a speaker—for example, selecting from a 'pleasant' song from a database or 'bank' of 'candidate songs.' Alternatively or additionally, a 'flash of light' or 'light therapy' may be provided—e.g. by light box; (ii) controlling the temperature in a location (e.g. in the room) where a subject is located—e.g. in the winter (summer) if a subject is 'stressed' the stress might be treated by increasing (decreasing) the temperature in the room. Thus, in some embodiments, in response to a DLS/BSRD-based determining of the stress-state or mood-state of the subject, a signal is sent to a device for regulating an indoor temperature (e.g. heating device or an air-conditioning device and/or an HVAC (heating, ventilating, and air conditioning; also heating, ventilation, and air conditioning) system—for example, to increase or decrease a set-point temperature.

Another example relates to modifying operating parameter(s) of a user interface For example, in response to a DLS/BSRD-based determination that a subject is in a 'high-stress state' or in a 'bad mood' (e.g. sad or depressed), an operating parameter of a GUI may be modified—e.g. to increase a font-size (making text easier to read) or to modify background color to a more 'relaxing' color (e.g. more of a blue shade) or any other operating parameter.

In yet another example, advertising may be served to a user in response to a DLS/BSRD-based determination of mood and/or stress—e.g. in response to a determining that the user is in a 'good mood' or in a 'low stress state' an advertisement for a more expensive item (e.g. luxury item) may be served. Alternatively or additionally, in response to a determining that the user is in a 'bad mood' or "high stress state' an advertisement for 'comfort food' may be served to the user.

In yet another example, advertising may be served to a user in response to a DLS/BSRD-based determination of fitness parameter—e.g. if the user is deemed to be 'not fit' an advertisement for a product to remedy the situation (e.g. exercise equipment) may be served to the user.

In yet another example related to 'treating stress and/or mood' (i) an electrical signal may be sent (e.g. via an electrode) to stimulate the subject and/or (ii) an electric (or electromagnetic) protocol for treating depression may be updated.

In yet another example, a monitored subject is using an electronic communication network (e.g. a packet-switched network or the Internet or a cellular network) and in response to a DLS/BSRD-based determination of mood and/or stress, the amount of bandwidth allocated to the user may be modified—e.g. if the user is 'stressed' or 'in a bad mood' the amount of bandwidth may be increased.

In yet another example, an alert-signal or alarm-signal may be generated—e.g. in response to a determining of an apnea-incident or a 'bad' mood or stress-state.

Figure 9A:
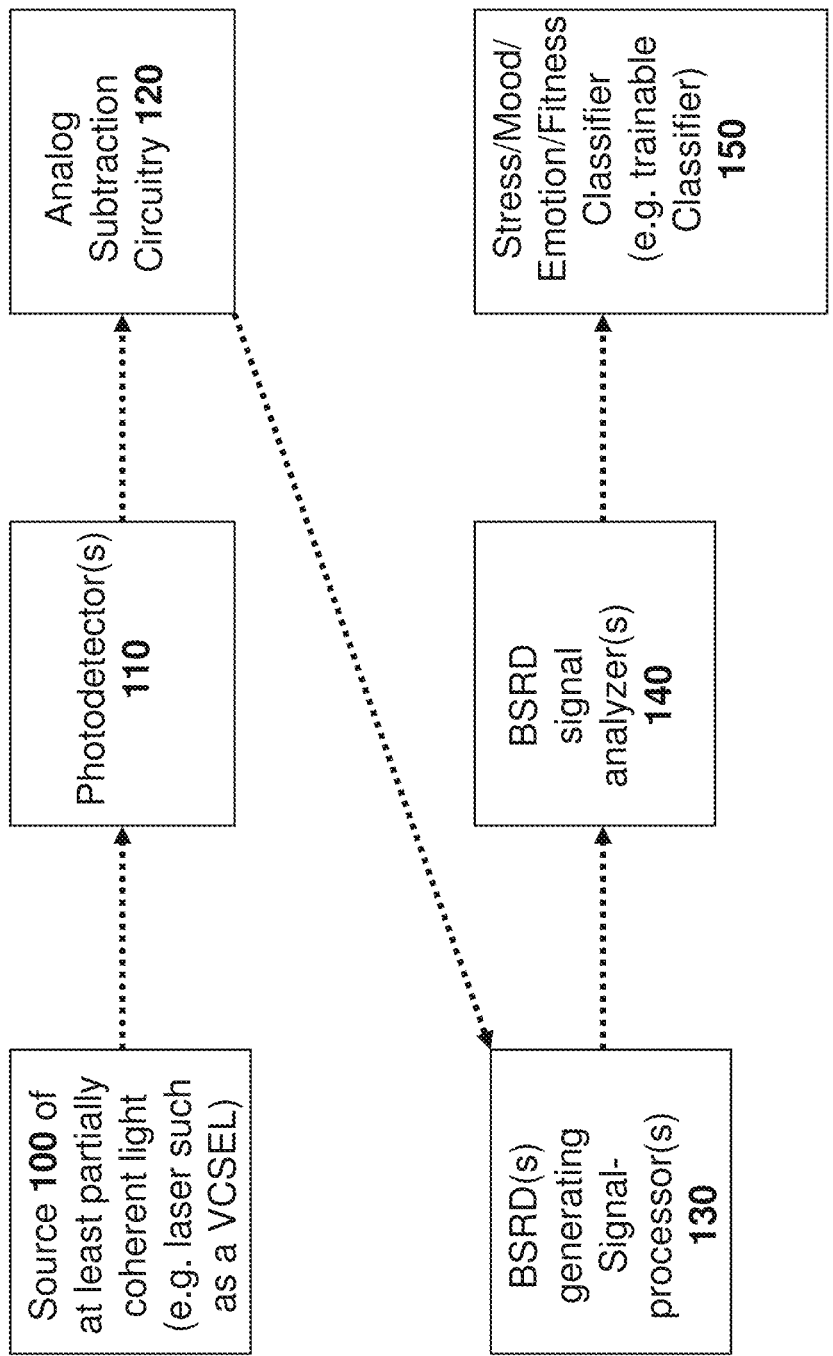
Figure 9B:
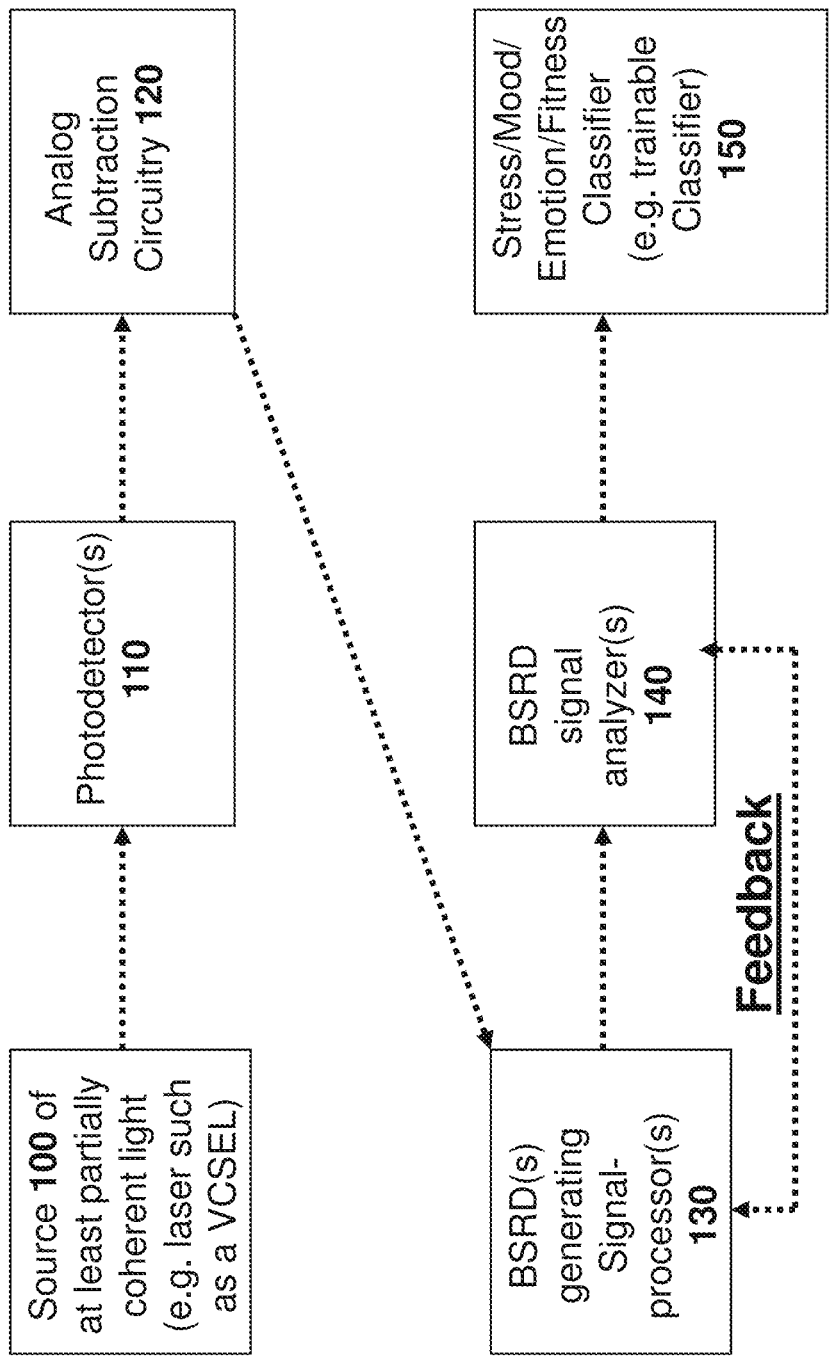

Discussion of FIGS. 9A-9B

FIG. 9A is a block diagram of a system for detecting stress and/or mood and/or emotion and/or fitness and/or stress-resistance of a mammalian subject. Not every element in FIG. 9 is required, and no attempt has been made to illustrate every element provided in all embodiments of the invention.

The system of FIG. 9A comprises: a source 100 of at least partially coherent light, photodetector 110, optional analog subtraction circuitry 120, BSRD(s) generating signal processor(s) 130, BSRD signal analyzer(s) 140 and stress/mood/emotion/fitness classifier 150. Any other these elements may be implemented in, or include 'electronic circuitry.'

FIG. 9B is like FIG. 9A—however, in FIG. 9B, element 130 generates BSRD signal(s) according to In the present disclosure 'electronic circuitry' is intended broadly to describe any combination of hardware, software and/or firmware.

In one particular example, power spectrum integral (or generating BSRD by any other method) may be performed by ASIC or customized hardware and/or DSP (e.g. configured by firmware). Thus, in some embodiments, this may be for generating the BSRD or for analyzing the BSRD (e.g. computing an integral (e.g. power spectrum integral) thereof.

Electronic circuitry may include any executable code module (i.e. stored on a computer-readable medium) and/or firmware and/or hardware element(s) including but not limited to field programmable logic array (FPLA) element(s), hard-wired logic element(s), field programmable gate array (FPGA) element(s), and application-specific integrated circuit (ASIC) element(s). Any instruction set architecture may be used including but not limited to reduced instruction set computer (RISC) architecture and/or complex instruction set computer (CISC) architecture. Electronic circuitry may be located in a single location or distributed among a plurality of locations where various circuitry elements may be in wired or wireless electronic communication with each other.

Figure 7A:
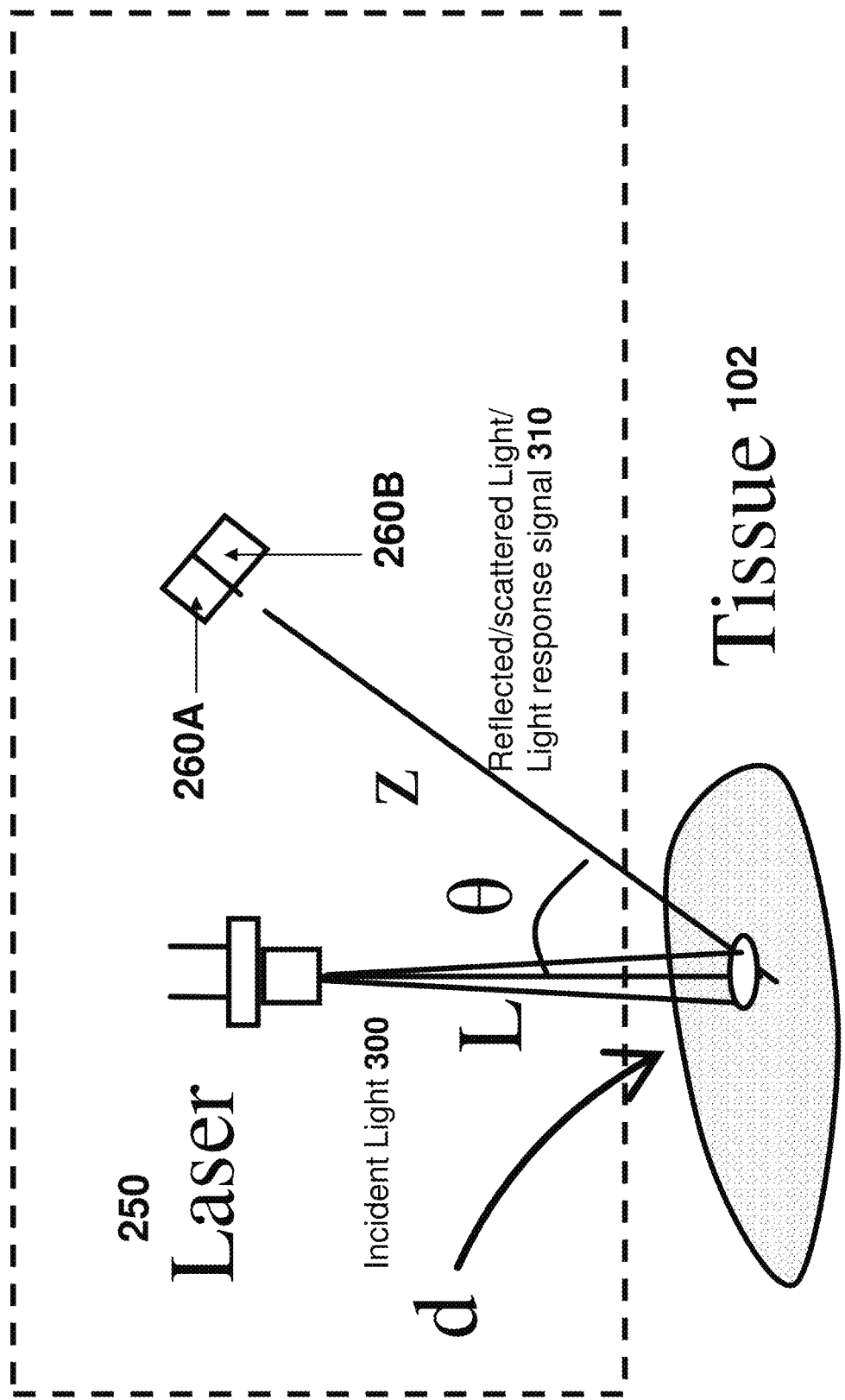
Figure 7B:
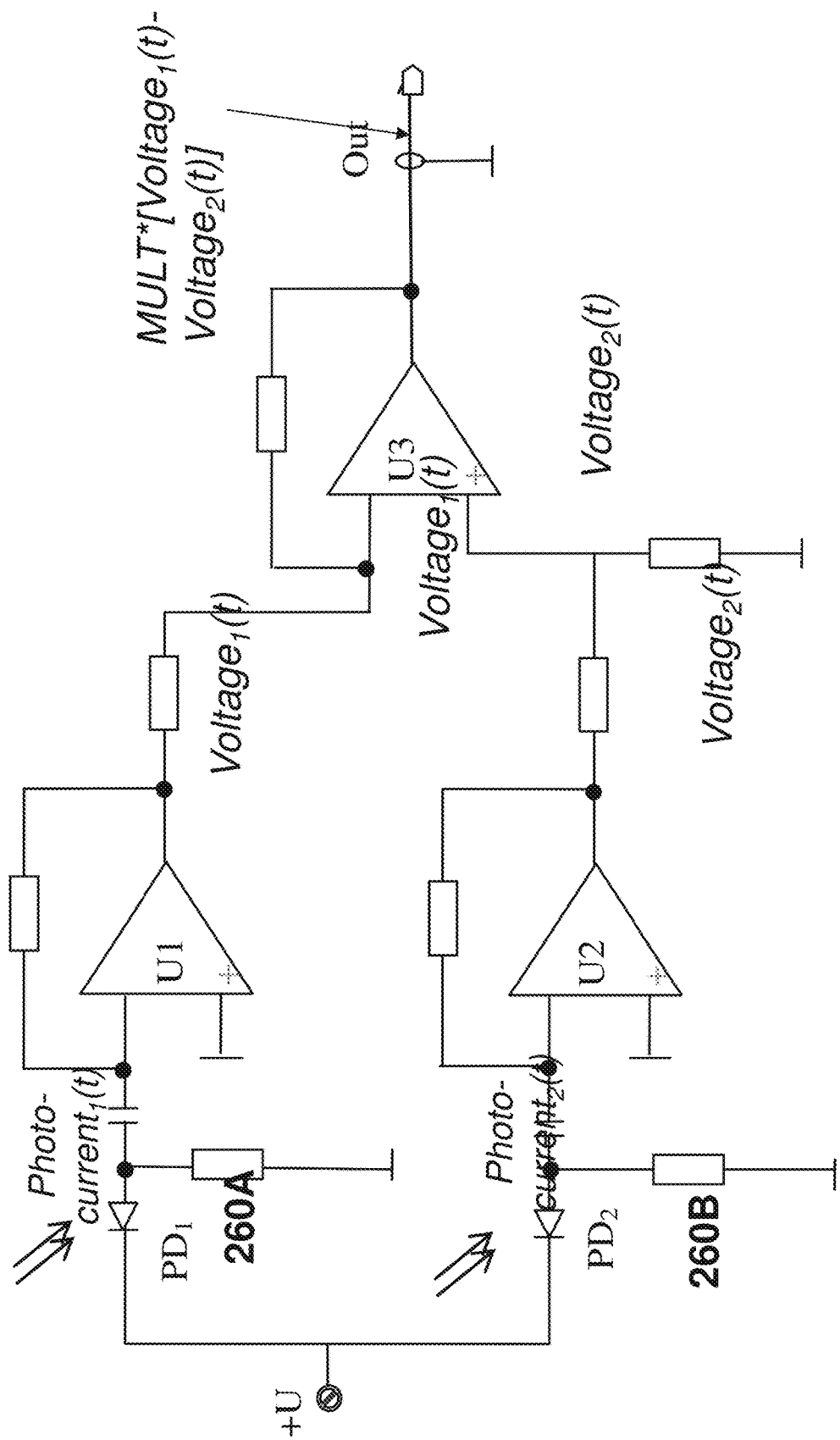
Figure 8:
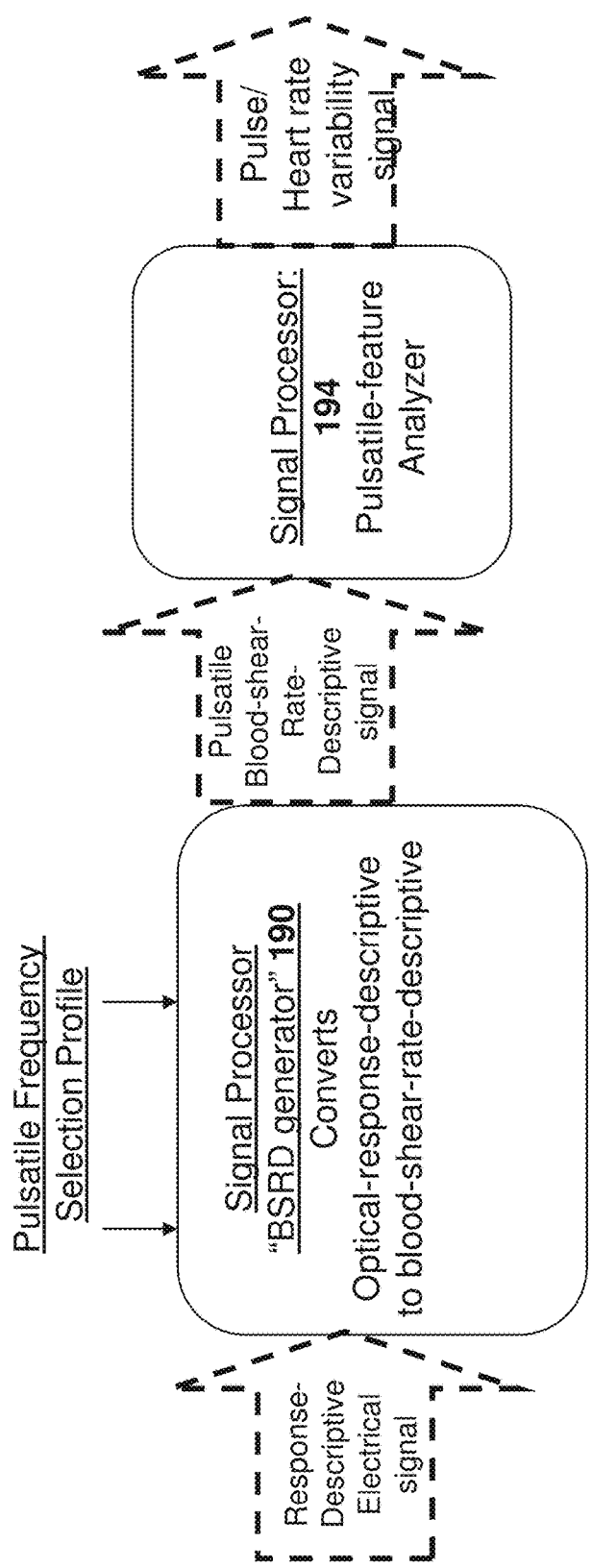
FIGS. 8, 9A-9B, 22B, 25, show data flow according to some embodiments.

In some embodiments, element 120 is implemented as shown in FIG. 7B.

Photodetector(s) 110 generate an electrical signal descriptive of the induced scattered-light time-dependent optical response. After initial processing of this "electrical signal descriptive of the induced scattered-light time-dependent optical response" the result may still be an electrical signal descriptive of the induced scattered-light time-dependent optical response—for example, initial processing may be performed by analog circuitry of FIG. 7B. Examples of 'generating' an electrical signal descriptive of the induced scattered-light time-dependent optical response are presented in flow charts below—see, for example, step S355 of FIG. 10, step S205 of FIG. 12, step S405 of FIGS. 18A-18B, In some embodiments, the BSRD signal processor 130 is configured to dynamically generate the BSRD (see, for example, step S359 of FIG. 10, step S309-323 of FIG. 12, steps S601, S619 and S623 of FIG. 16). Alternatively or additionally, BSRD signal processor 130 may be configured to generate non-pulsatile BSRD(s).

The BSRD(s) generated by BSRD-generating signal-processor 130 are analyzed by BSRD signal analyzer(s) 140 (see, for example, step S363 of FIG. 10, steps S609-S13 of FIG. 16, As will be discussed below, in some embodiments, BSRD-generating signal-processor 130 receives feedback derived from the results of BSRD signal analyzer(s).

Figure 10:
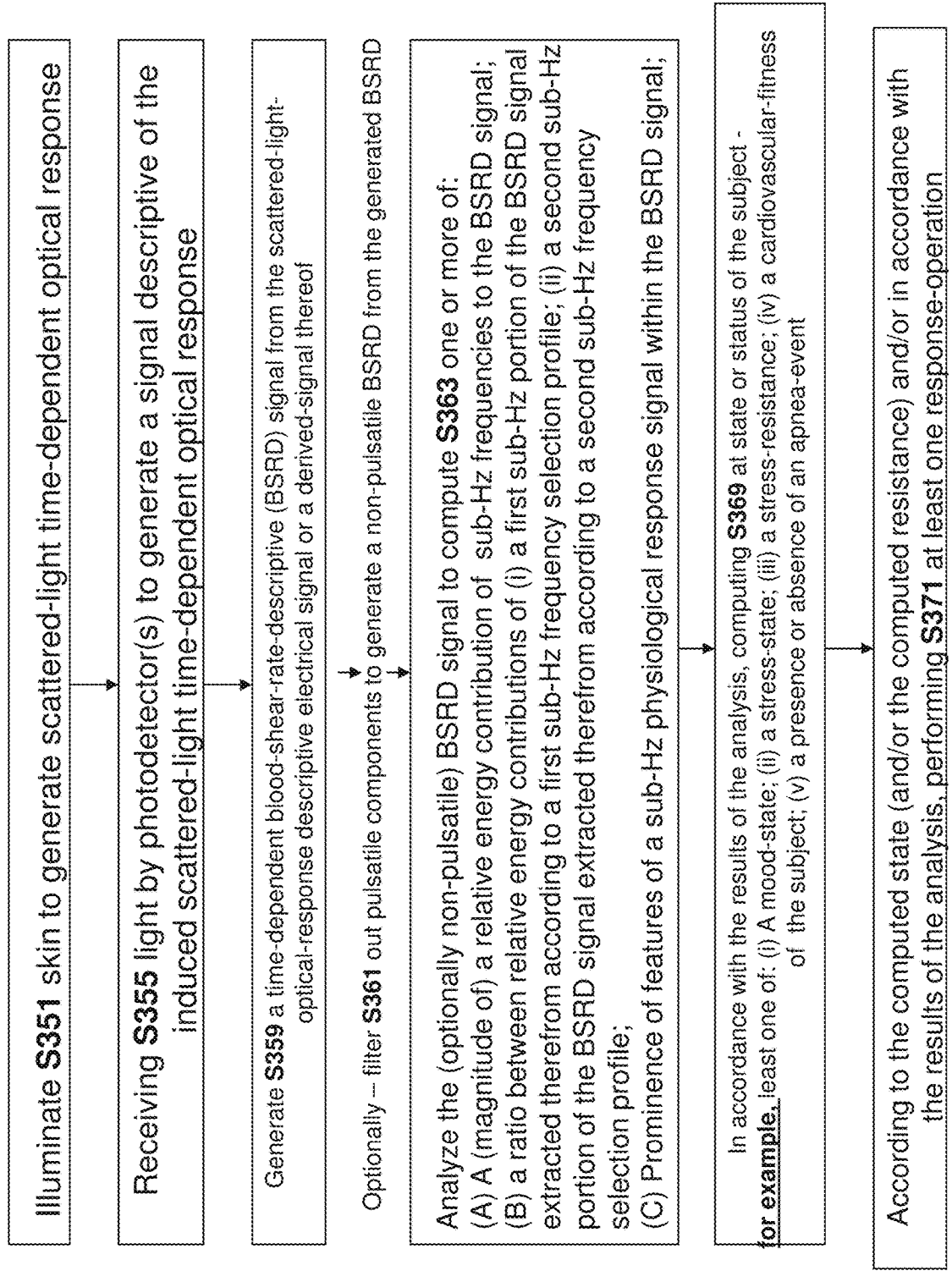

Element 150 is to compute and/or predict (and/or classify) a state of the warm-blooded subject (e.g. mammalian subject—for example, human) a stress state and/or dominant type of stress and/or emotion state and/or fitness parameter of the subject —see, for example, step S369 of FIG. 10, step S327 of FIG. 12.

A Comment about Response—in any embodiment, for any analysis or determining or computing of a state (or resistance or any other parameter) of a warm-blooded subject (e.g. stress-state, mood-state, emotion-state, apnea-state, stress-resistance, cardiovascular fitness state) disclosed herein, one or more (i. any combination) of responses may be optionally provided. These response may include: (i) presenting to a user (e.g. visually on a display-screen or by audio means—for example using a speaker) a description of the determined state; (ii) trigger an alarm or alert signal (iii triggering therapy (e.g. massage, food, image/drug, resistance for an exercise machine, temperature, serve audio (e.g. music) or video (e.g. video), or smell, light frequency modulation (e.g. hypnosis), biofeedback) to reduce a stress state or improve a mood or fitness; (iii) serving advertisement to a user—e.g. we time the advertisements for when the user is in a good mood he will be more likely to respond positively—the proper moment. E.g. If the user is in a bad mood, an advertisement certain 'mood-improving items' (e.g. sweet foods or relaxing beverages) may be served; (iv) updating the subject's user-profile (v) adjusting display-parameter(s) of a GUI operated by the user (vi) upgrading or downgrading use-privileges—for example, if a user is stressed his/her available bandwidth might be reduced to reduce his/her stress level (thereby increasing use privileges)—in another example, when a user of a motorized vehicle is stressed the maximum speed that s/he is permitted to drive may be reduced for safety reasons, thereby downgrading use privileges; (vii) subjecting the user to additional test of stress level or mood (e.g. by voice-print or processing an image of face or in any other manner) (vii) matching (e.g. dating, business matching, etc)—social networking (ix) social networking—to suggest additional friends; (x) presenting a list of search results that is biased by the user's mood or stress-state or stress-resistance; (xii) serving a user food or beverage adapted to the user's mood or stress-state or stress-resistance—for example, a food/beverage dispenser may increase caffeine or alcohol or sugar content to a 'unhappy user'

In some embodiments, any technique disclosed herein may be used to measure and/or respond to fatigue or substance-addiction or pain.

Overview of FIGS. 10, 12, 16, 18A-18C, 22A, 23

FIGS. 10, 12, 16, 18A-18C, 22A, 23 are steps of methods for detecting a emotional state, a stress-state, mood-state, and/or cardiovascular fitness parameter of warm-blooded (e.g. mammals or birds) individuals.

Figure 11A:
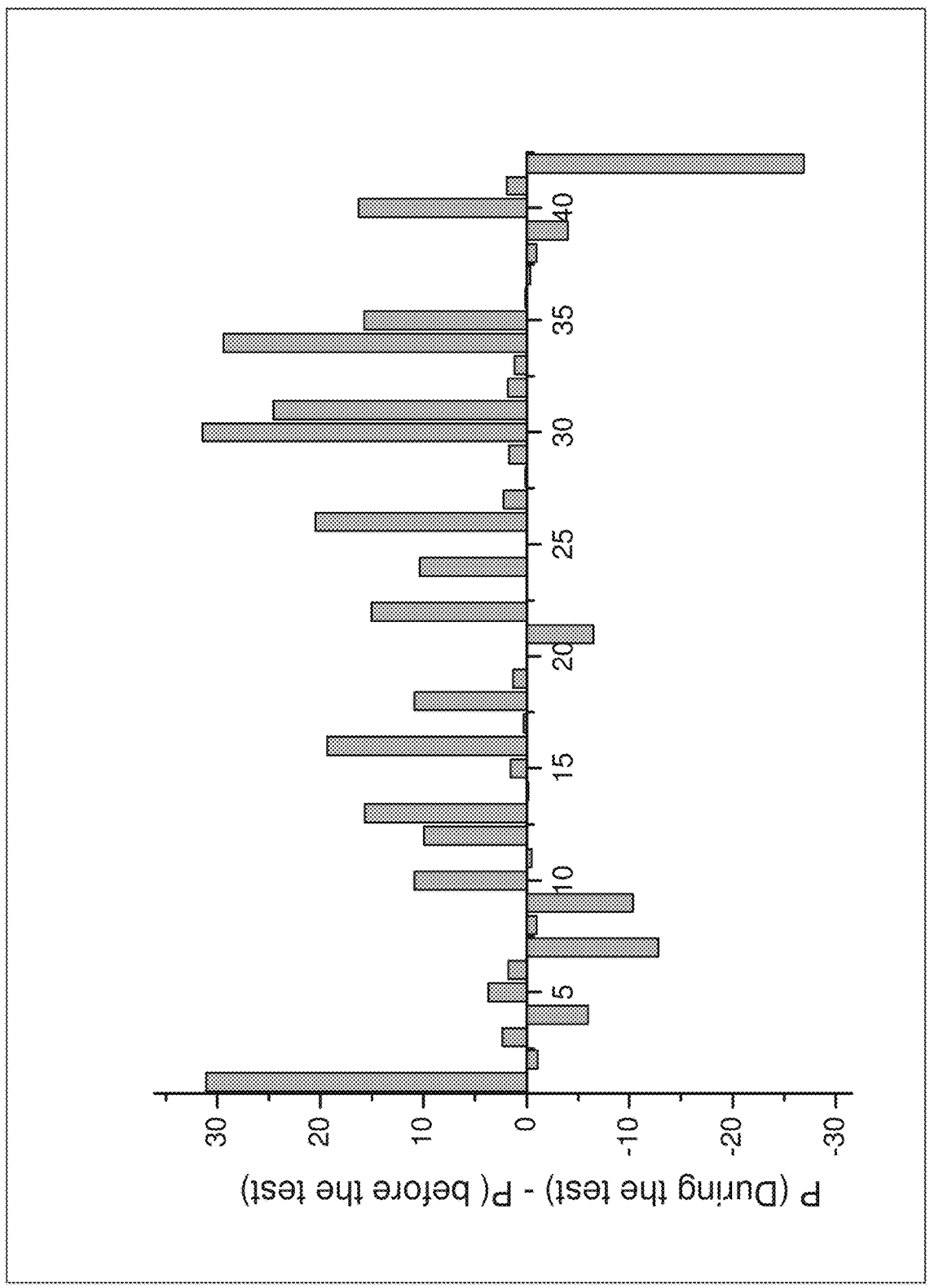

Brief Description of FIGS. 10-11 (computing mood and/or stress and/or fitness and/or emotion according to strength of a contribution of a sub-Hz frequency-band(s) and/or signal to a BSRD)—one salient feature of the method of FIG. 10 is that sub-Hz frequency(ies) of a BSRD are analyzed (e.g. frequencies of neurogenic and/or myogenic and/or respiratory oscillators of the blood-shear signal—e.g. non-pulsatile component(s) of the shear signal)—for example, specific features thereof. These specific feature may include relative energy contributions at specific bandpass frequencies to an overall BSRD signal and/or a ratio between energy contributions in different sub-Hz 'bands' (below the pulsatile) and/or prominence of a sub-Hz physiological signal (e.g. neurogenic and/or myogenic and/or respiratory signal present within the blood-shear signal—Mayer wave) within a BSRD. Thus, in one non-limiting example related to a specific sub-Hz physiological signal (Mayer wave), it is possible to compute a strength of a 'Mayer wave' contribution to a BSRD signal (e.g. generated by scattering coherent light from RBCs. In response to detecting a relatively 'strong' Mayer wave contribution within a BSRD, an indication is provided that the warm-blooded subject's stress-state is 'high mental stress." This may be measured and corroborated by a Stroop test (see FIG. 11A and the discussion below).

Thus, FIG. 10 is a flow chart of a method for sensing emotion and/or mood and/or a stress-state and/or a cardiovascular fitness parameter of a subject. Steps S351 and S355 respectively correspond to steps S201 and S205 and FIG. 3B. In step S359 a time-dependent BSRD signal is generated from the scattered optical response descriptive electrical signal or a derive signal thereof—e.g. using any algorithm or combination of algorithms disclosed in WO 2008/053474 or WO2012064326 and/or US 20150141766, each of which is incorporated herein by reference in its entirety. Thus, in some embodiments, BSRD(s) generating Signal-processor(s) 130 implements any algorithm or any algorithm or combination of algorithms disclosed in WO 2008/053474 or WO2012064326 and/or US 20150141766.

These algorithms for generating a BSRD are really a family of algorithms that are parameterized by a frequency selection profile. Thus, in different embodiments, frequency selection profiles other than those disclosed in WO 2008/053474 or WO2012064326 and/or US 20150141766 are employed.

Examples of frequency selection profiles disclosed in WO 2008/053474 are the frequency 'windows' PwS of the power spectrum—for example, [0 Hz, 550 Hz,] and [2700 Hz, 10000 Hz]. These windows are essentially step-functions or band-pass filters.

Definitions

For convenience, in the context of the description herein, various terms are presented here. To the extent that definitions are provided, explicitly or implicitly, here or elsewhere in this application, such definitions are understood to be consistent with the usage of the defined terms by those of skill in the pertinent art(s). Furthermore, such definitions are to be construed in the broadest possible sense consistent with such usage.

The term 'stress' may refer to detecting a stress-state or detecting a relaxation state—i.e. the relative presence or absence of stress. For the present disclosure, stress refers to non-physical stress—in particular, to emotional stress or mental stress. Non-physical stress may be (i) emotional stress (e.g. in response to an (un)pleasant sound or temperature or smell or 'good news' or 'bad news' or in response to any other negative or positive stimulus; in another example, an attempt to lie may trigger emotional stress; in another example, good news may relieve tension and lead to an absence of stress —especially, right after hearing the good news) or (ii) mental stress (e.g. attempting to solve a puzzle or to perform mathematics; in another example, when a student is completing his/her homework this may be mental stress; when attempting to draft a patent application, this is also mental stress). The term 'emotion' and 'mood' are used interchangeably.

Computing a 'state' of a subject may include: (i) quantifying a magnitude of a state of the subject—to distinguish between a slightly-happy and extremely happy subjects or to determine if a subject is slightly stressed or extremely stressed; (ii) computing a stress-load (e.g. mental-load in the case of mental stress)—i.e. a magnitude of stress—i.e. to quantify a presence or absence of stress; (iii) differentiating between two or more candidate states (e.g. to determine if a subject is more 'happy' than 'anxious,' or more 'happy than angry'); (iv) determining a dominant state among two or more candidate-states (e.g. to determine if a dominant stress state is mental-stress or emotional-stress).

The term "physiological response signal" refers to a physiological response (i.e. as manifested in blood flow) to input and/or feedback from the central nervous system. Examples of physiological responsible signals include (with reference to FIG. 2A) metabolic response signals, neurogenic response signals, myogenic response signals, respiratory response signals and heart/pulse signals response. The signal can be described in the time domain or the frequency domain (e.g. as a power spectrum).

Figure 31A:
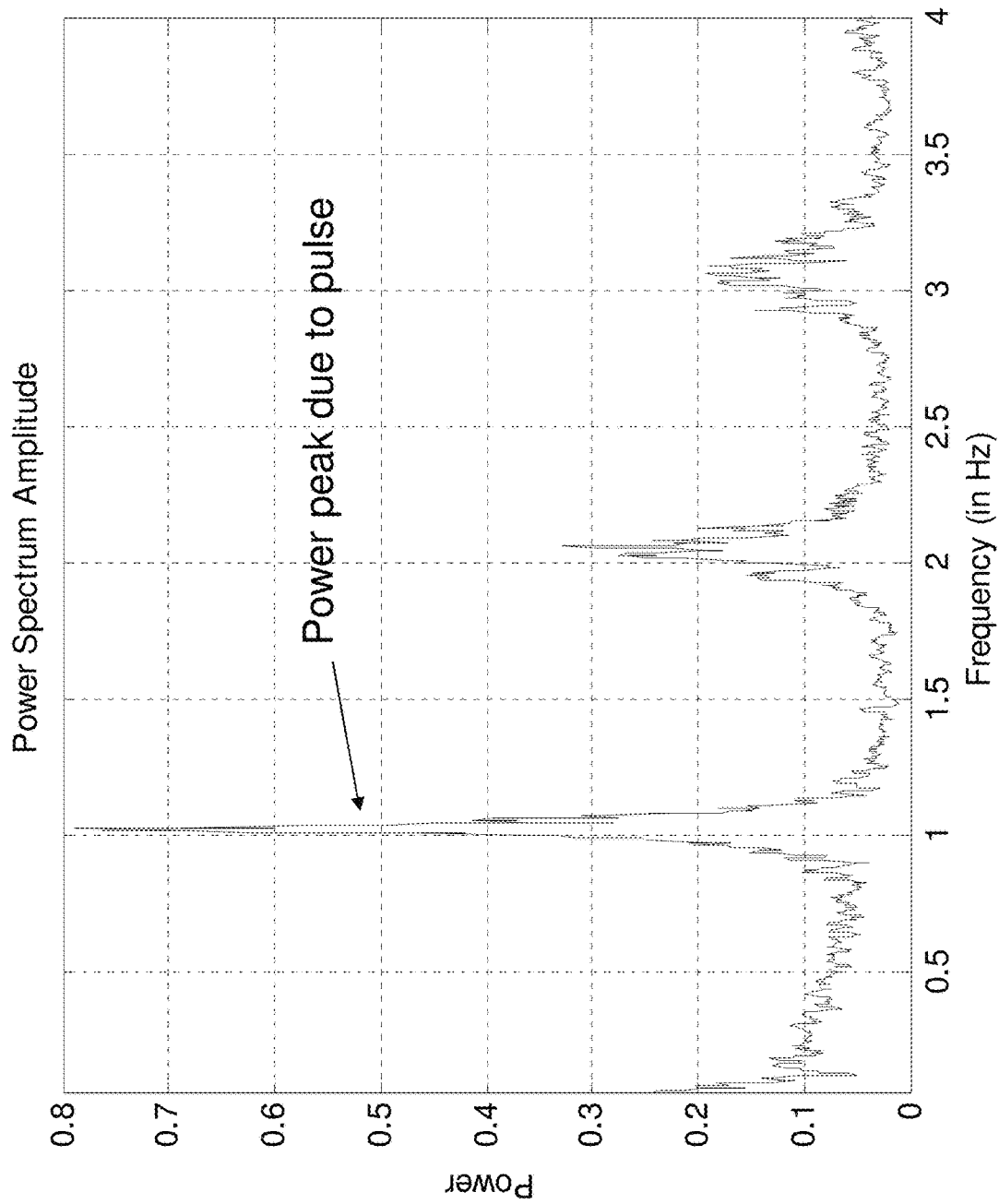
FIGS. 31A-31C describe power spectrum amplitudes.
Figure 31B:
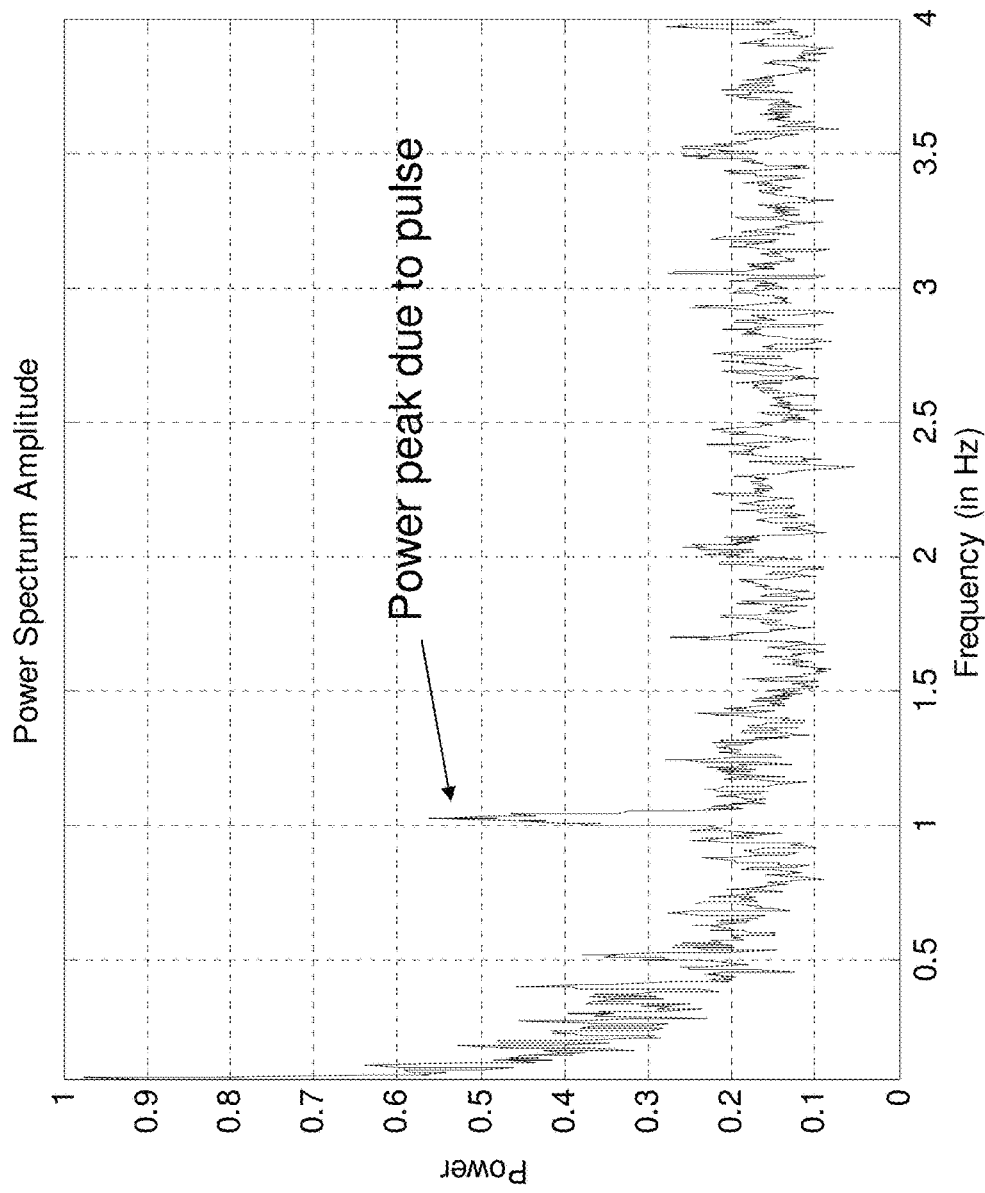
Figure 31C:
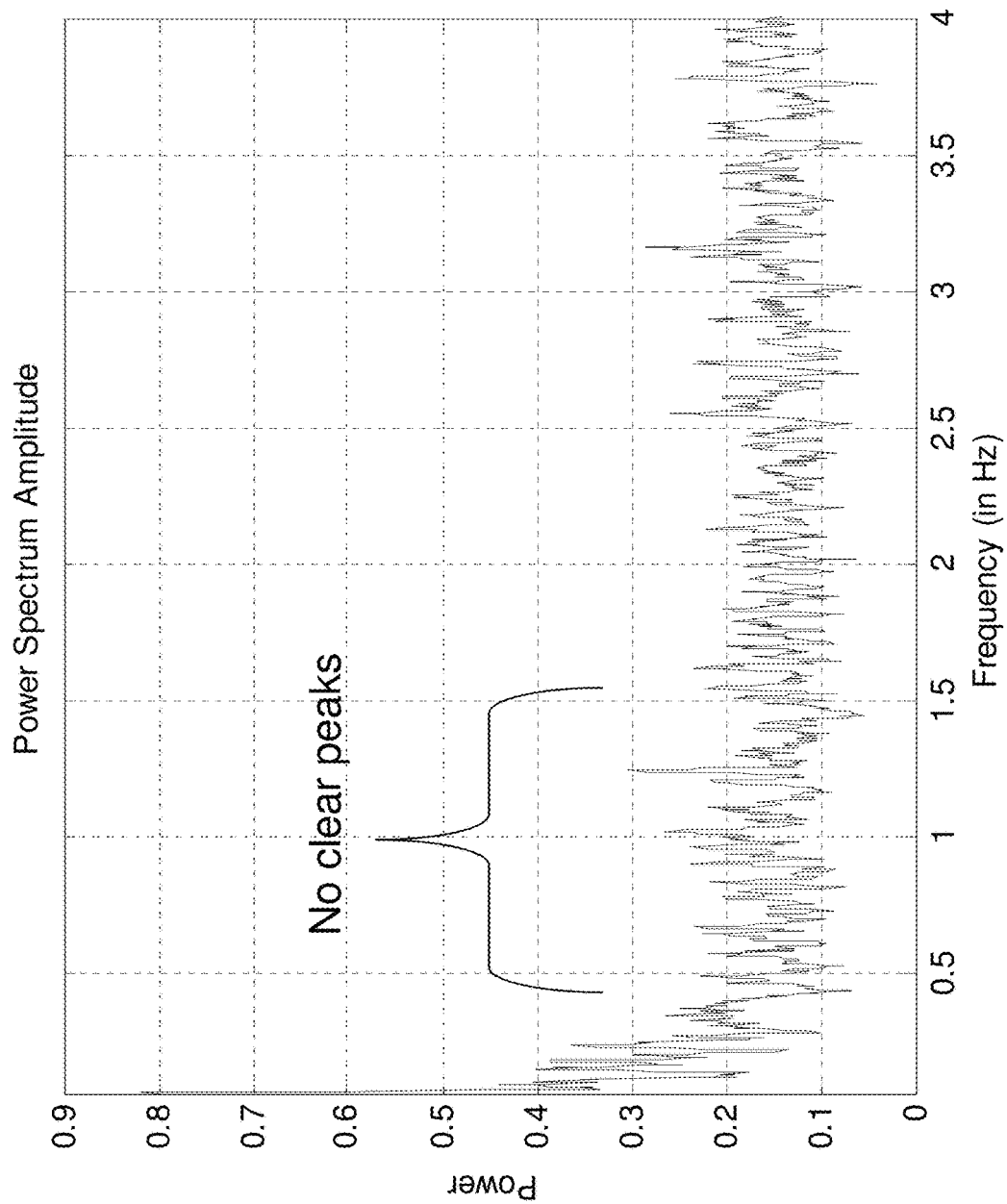
Figure 32A:
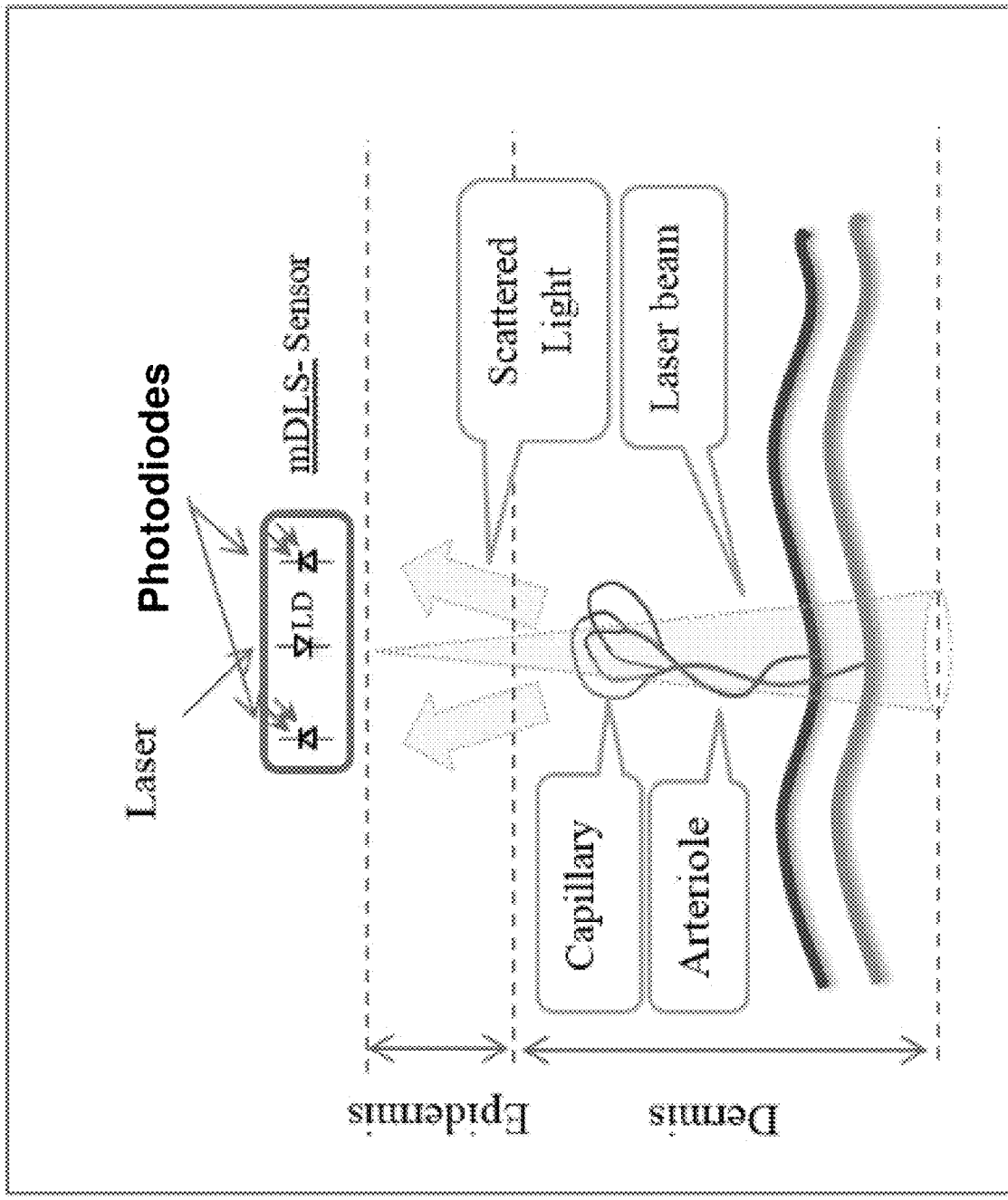
FIGS. 32A-32B, 33, 34A-34B, 35A-35B, and 36A-36B illustrate additional embodiments.
Figure 32B:
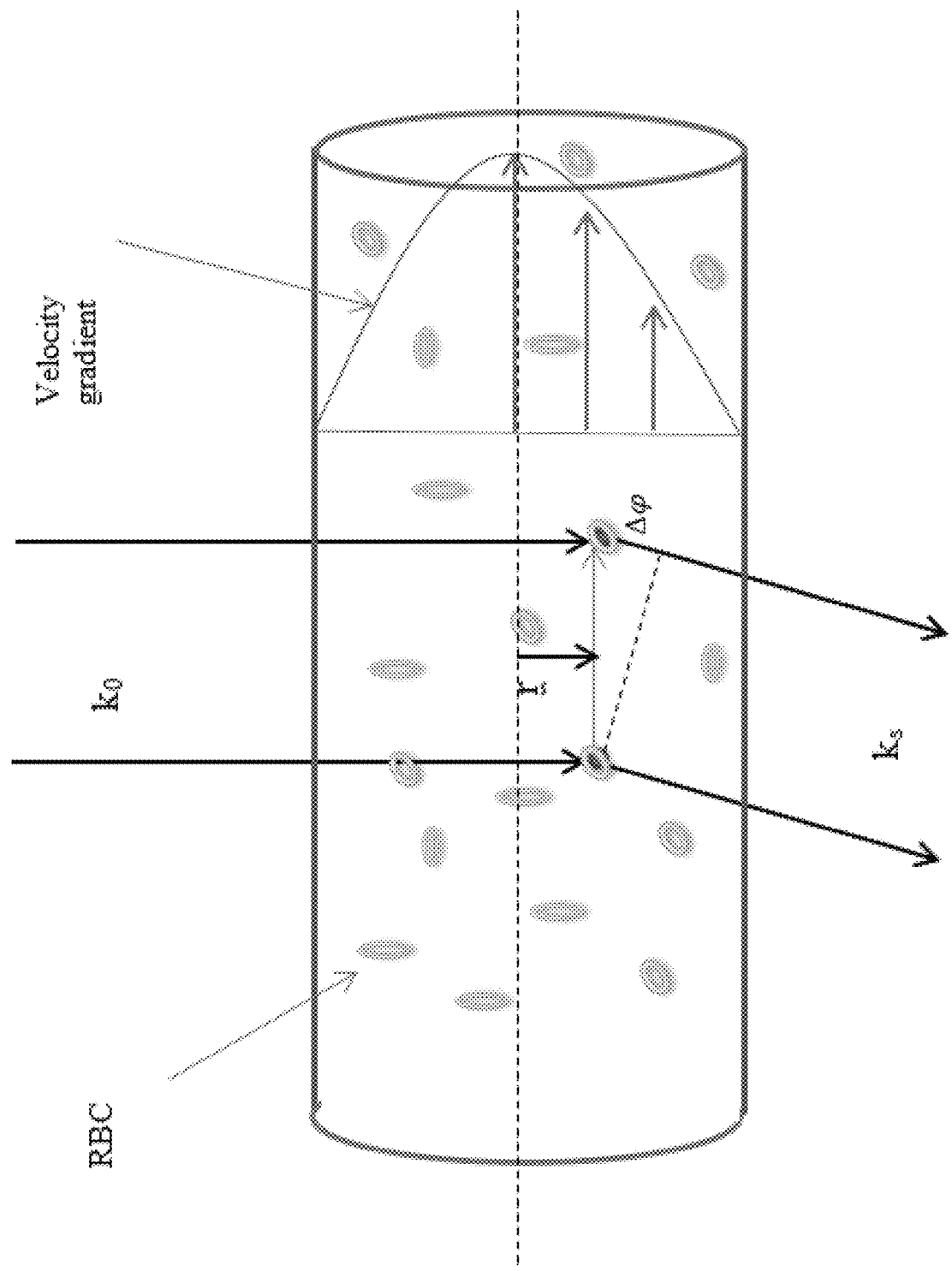

Some embodiments relate to a 'non-pulsatile' signal (BSRD) —strongly pulsatile vs. weakly pulsatile vs non-pulsatile signals may be determined and defined according to the power spectrum of the signal (e.g. BSRD). A signal (e.g. BSRD) may be pulsatile (see FIG. 31A) if there are clear power peaks in the range between 0.4 Hz and 3.5 Hz —thus in FIG. 31A the 'strong peak' is the pulse and this is clearly a pulsatile BSRD. In FIG. 31B, the peak is still present but not as strong—this is for a 'weakly puslatile' (but still pulsatile BSRD). In FIG. 31C, there are no clear peaks for the power spectrum of the BSRD in the range between 0.4 Hz and 2 Hz. The intention of this definition of 'non-pulsatile' signals is not intended the definition known in the art by the skilled artisan, but merely to harmonize with/clarify the definition known in the art by the skilled artisan.

A 'stress-resistance' relates to stress-states as follows: (i) a subject may be subjected to a stressful stimulus (where the stress stimulus may be quantified to distinguish between a 'small stimulus' and a 'large stimulus'); (ii) the subject's stress-state before the stimulus and after the stimulus may be quantified. In the event that a 'small' or 'minor' stress stimulus induces a relatively large 'increase in stress-state' this may be indicative of a low stress-resistance. Conversely, in the event that a 'large or 'major' stress stimulus only induces a relatively small 'increase in stress-state' this may be indicative of a high stress-resistance.

Electronic circuitry may include may include any executable code module (i.e. stored on a computer-readable medium) and/or firmware and/or hardware element(s) including but not limited to field programmable logic array (FPLA) element(s), hard-wired logic element(s), field programmable gate array (FPGA) element(s), and application-specific integrated circuit (ASIC) element(s). Any instruction set architecture may be used including but not limited to reduced instruction set computer (RISC) architecture and/or complex instruction set computer (CISC) architecture. Electronic circuitry may be located in a single location or distributed among a plurality of locations where various circuitry elements may be in wired or wireless electronic communication with each other.

"Computer storage' (or just 'storage') is volatile (e.g. RAM) and/or non-volatile (e.g. magnetic medium or flash) memory readable by an electronic device (e.g. digital computer).

Analog electrical signals or light fields may comprises more than one sub-signal added together in a single electrical (or optical) signal. For example, an analog electrical signal derived from a light field detected by a photodetector that (i.e. where scattered light that is scattered from particles within a fluid contributed to the light field) may be the sum of: (i) a first component (i.e. analog electrical sub-signal) attributable to ambient light (e.g. sunlight); (ii) a second component attributable to skin light-modulating effects; (iii) a third component attributable to regular fluctuations in light intensity due to the presence of a fluorescent bulb and (iv) a fourth component attributable to scattered light that is scattered from particles within a fluid contributed to the light field. Each component or sub-signal of the analog electrical signal is associated with a different respective amount of power.

In some examples, for an analog signal generated by a photodetector, the relative power contribution to overall analog signal power attributable to ambient light is relatively high (i.e. the first component), while the relative power contribution to overall analog signal power attributable to scattered light that is scattered from particles within a fluid is relatively low (i.e. second component).

In general, both a signal and a sub-signal have power levels—the fraction of the power level of the overall signal attributable to a particular portion of the signal or sub-signal is the 'power fraction' of the sub-signal or signal component. In the example of the previous paragraph, the power fraction of the overall analog electrical signal due to the ambient light component may be significant (e.g at least 0.1 or at least 0.3 or at least 0.5) while the power fraction of the overall analog electrical signal due to the 'light scattering' component (i.e. fourth component) may be relatively low—for example, at most 0.1 or at most 0.05 or at most 0.01).

Embodiments of the present invention relate to generating a 'hybrid' signal. A 'hybrid signal' derived from a plurality of input analog signals is any non-zero or non-trivial mathematical combination of the input analog signals—i.e. including multiplication, addition, subtraction, etc. The term 'hybrid' refers to the fact that the output (or hybrid) signal relates to more than one input signal, and is not restricted to a single input.

Embodiments of the present invention relate to photodetectors (any technology may be used including those listed herein or any other technology). In some embodiments, each photodetector is not infinitesimally small but rather has a size. The 'distance' between photodetectors relates to a centroid-centroid distance.

In some embodiments, a light field is comprised of more than on component. Whenever light is generated and reflected or scattered (or modulated in any other manner) to introduce photons into (or to pass through) a certain location (and/or to illuminate the location), this light 'contributes to' or 'influences' the local light field at that certain location.

Embodiments of the present invention relate to optically measuring a parameter relating to a subject. In different embodiments, this subject is human, or a mammal other than human, or to a warm-blooded animal other than mammals (e.g. birds).

Whenever a power level of a second signal is 'significantly less' than a power level of a first signal, a ratio between a power level of the second signal and a power level of the first signal is at most 0.5 or at most 0.3 or at most 0.2 or at most 0.1 or at most 0.05 or at most 0.01.

Some embodiments of the present invention are described for the specific case of only two photodetectors and/or measuring a light field in two locations. The skilled artisan will appreciate that this is not a limitation, any teaching disclosed herein may relate to the case of more than two photodetectors or detecting light fields in more than two locations. Thus, two photodetectors refers to 'at least two,' 'two locations' refers to at least two, and so on.

A product of a 'first signal' is a second signal that is derived from the first signal—this does not require 'multiplication.'

A 'derivative' of a 'signal' is a signal that is derived therefrom—this does not require computing a 'mathematical derivative' as is known in calculus.

'Quantifying a correlation' between two functions or data-sets refers to computing a slope between the data sets of some of the parameter of curvefitting (linear or non-linear) or a goodness of a fit.

For any apparatus disclosed herein, a "source of partially or entirely coherent light" may be, but is not required to be, a vertical-cavity surface-emitting laser VSCEL.

The [a Hz, b Hz] notation (both a and b are non-negative real numbers, b>a) used in WO 2008/053474 to describe 'frequency windows' is used to describe a 'frequency selection profile. The same [a Hz, b Hz] notation is used to describe a 'frequency selection profile' and a BSRD. A [a Hz, b Hz]

For the present invention, when an input signal (e.g. a BSRD signal or scattered-light time-dependent optical response signal) is subjected to a frequency selection profile, some frequencies of the input signal are retained and other frequencies selectively are rejected. One example of a 'frequency selection profile' is a 'frequency window'/step function/band-pass filter—however, this is not a limitation—other filters include but are not limited to Butterworth filters, Chebyshev filters, and Elliptic filters. In the case of a 'band-pass filter,' 100% of energy of the input signal is rejected at frequencies outside of the 'window'—however, this is not a limitation and in other examples, most but not all energy of the input signal may be rejected outside of 'frequency range' defining the frequency selection profile.

As noted above, the same [a Hz, b Hz] notation is used in WO 2008/053474 is used to describe a 'frequency selection profile'—however, they do not mean the same exact thing. A [a Hz, b Hz] frequency selection profile retains at least 65% of (in some embodiments, at least 75% or at least 90% or at least 95%) of energy of the input signal for frequencies of at least a Hz and at most b Hz, and rejects at least 65% of (in some embodiments, at least 75% or at least 90% or at least 95%) of energy for frequencies of less than a Hz and for frequencies greater than b Hz.

The [a Hz, b Hz] notation (both a and b are non-negative real numbers, b>a) used in WO 2008/053474 in the context of defining a frequency window is not to be confused with the notation [a Hz, b Hz] BSRD. For the present disclosure, a [a Hz, b Hz] BSRD signal (both a and b are non-negative real numbers, b>a) is a BSRD signal where at least 50% or at least 75% or at least 90% or at least 95% or at least 99% of the energy of the BSRD signal has a frequency of at least a Hz and at most b Hz. A x % [a Hz, b Hz] BSRD signal is a specific type of [a Hz, b Hz] BSRD signal such that at least x % of the energy of the signal has a frequency of at least a Hz and at most b Hz. By definition, every [a Hz, b Hz] BSRD signal is at 50% [a Hz, b Hz] BSRD signal. For the present disclosure, any [a Hz, b Hz] BSRD signal disclosed herein may be a 50% [a Hz, b Hz] BSRD signal or a 75% [a Hz, b Hz] BSRD signal or a 90% [a Hz, b Hz] BSRD signal or a 95% [a Hz, b Hz] BSRD signal or a 99% [a Hz, b Hz] BSRD signal.

Some embodiments relate to a $[(a_1, a_2)$ Hz, $(b_1, b_2)$ Hz] BSRD signal where (i) $(a_1, a_2)$ refers to the range of numbers between $a_1$ and $a_2$ (ii) $b_1, b_2$ refers to the range of numbers between $b_1$ and $b_2$ and (ii) $a_2 > a_1$ and $b_2 > b_1$. For the present disclosure, a $[(a_1, a_2)$ Hz, $(b_1, b_2)$ Hz] BSRD signal is a $[a_1$ Hz, $b_2$ Hz] BSRD signal. A $[(a, Hz, (b_1, b_2)$ Hz] BSRD signal (where a1<b1<b2) is a [a Hz, $b_2$ Hz] BSRD signal. A $[(a_1, a_2)$ Hz, b Hz] BSRD signal (where a1<a2<b) is a $[a_1$ Hz, b Hz] BSRD signal For the present disclosure, sub-Hz frequencies are frequencies of at most 1 Hz. Sub 0.5-Hz frequencies are frequencies of at most 0.5 Hz. Sub 0.25-Hz frequencies are frequencies of at most 0.25 Hz. In any embodiment, 'sub-Hz' frequencies may refer to sub 0.5-Hz frequencies or sub-0.25 Hz frequencies.

A sub-Hz frequency selection profile, when applied to an input signal (e.g. a BSRD signal or scattered-light time-dependent optical response signal) rejects at least a majority (in some embodiments, at least 75% or at least 90% or at least 95% or at least 99%) of energy the input signal for most frequencies less than 1 Hz, and retains at least a majority (in some embodiments, at least 75% or at least 90% or at least 95% or at least 99%) of energy for most frequencies greater than 1 Hz. The same definition applies for sub-0.25 Hz frequency selection profile where '0.25 Hz' is substituted for 1 Hz. (in some embodiments, at least 75% or at least 90% or at least 95% or at least 99%).

A ~300 Hz frequency has a value of (i) at most 500 Hz or at most 450 Hz or at most 400 Hz or at most 350 Hz and (ii) at least 200 Hz or least 250 Hz.

A ~1000 Hz frequency has a value of (i) at most 1500 Hz or at most 1250 Hz or at most 1200 Hz or at most 1100 Hz and (ii) at least 750 Hz or at least 850 Hz or at least 900 Hz.

A ~4000 Hz frequency has a value of (i) at most 2500 Hz or at least 3000 Hz or at least 3500 Hz and (ii) at most 7500 Hz or at most 6000 Hz or at most 5000 Hz.

'Sub Hz' frequencies are frequencies less than 1 Hz. 'Sub 0.5 Hz' frequencies are frequencies less than 0.5 Hz. 'Sub 0.25 Hz' frequencies are frequencies less than 0.25 Hz.

Reference is made once again to FIG. 10. In step S363, the BSRD signal (for example, a 'non-pulsatile BSRD signal') is analyzed to compute one or more of: (i) (A) A (magnitude of) a relative energy contribution of sub-Hz frequencies (e.g. sub 0.5-Hz frequencies or sub 0.25 Hz frequencies) to the BSRD signal; (B) a ratio between relative energy contributions of (i) a first sub-Hz portion of the BSRD signal extracted therefrom according to a first sub-Hz frequency selection profile (e.g. according to a first sub-0.5 Hz frequency selection profile, or according to a first sub-0.25 Hz frequency selection profile); and (ii) a second sub-Hz portion of the BSRD signal extracted therefrom according to a second sub-Hz frequency selection profile (e.g. according to a second sub –0.5 Hz frequency selection profile, or according to a second sub-0.25 Hz frequency selection profile); (C) Prominence of features of a sub-Hz physiological signal (e.g. a sub 0.5-Hz physiological signal or a sub-0.25 Hz physiological signal) within the BSRD signal—for, example non-pulsatile physiological signal.

In step S369, the mood-state and/or emotion-state and/or stress-state (e.g. instant or immediate state) of the subject is computed. Alternatively or additionally, a cardiovascular fitness parameter is computed.

Figure 2A:
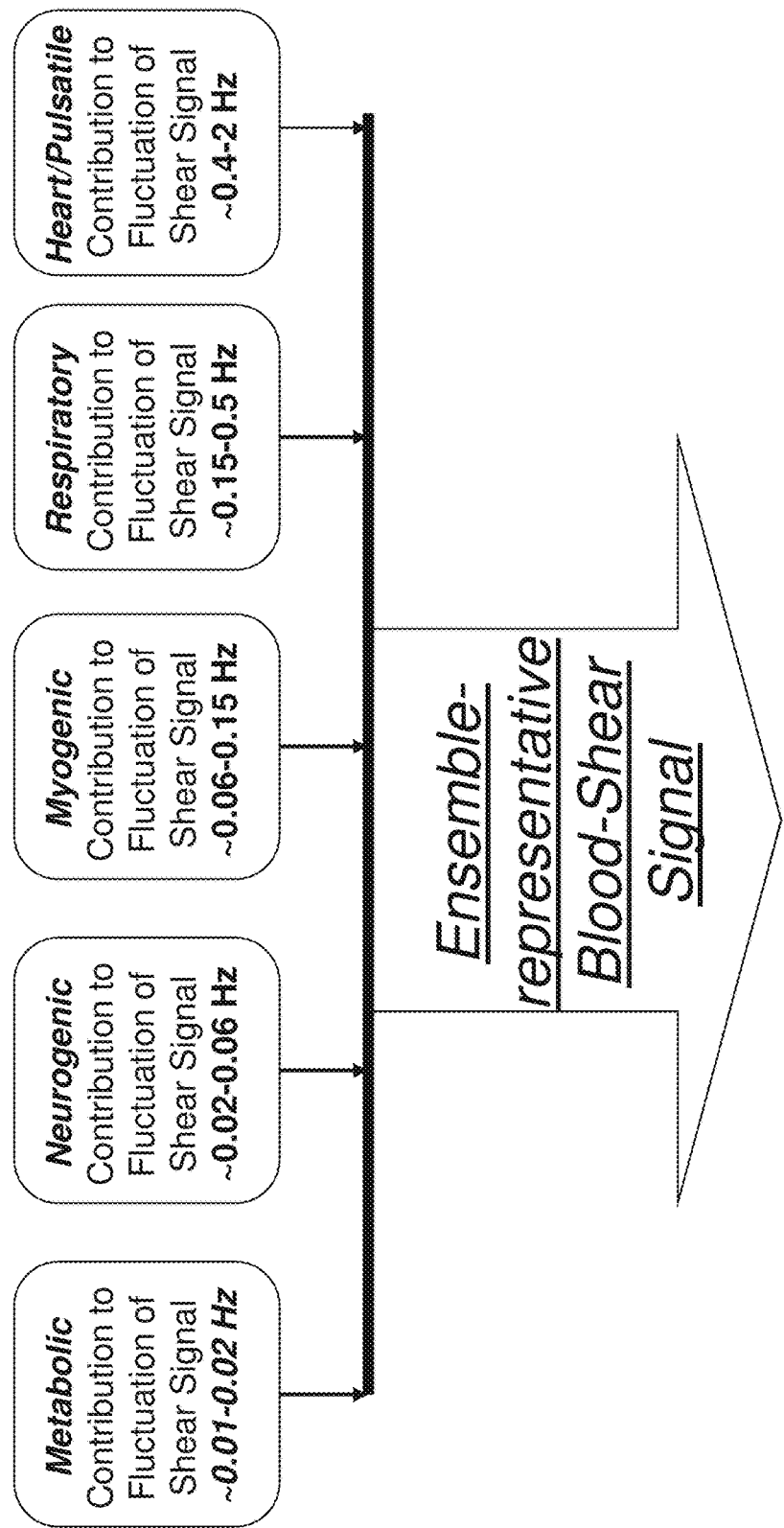
FIG. 2A shows information about physiological oscillators.
Figure 2B:
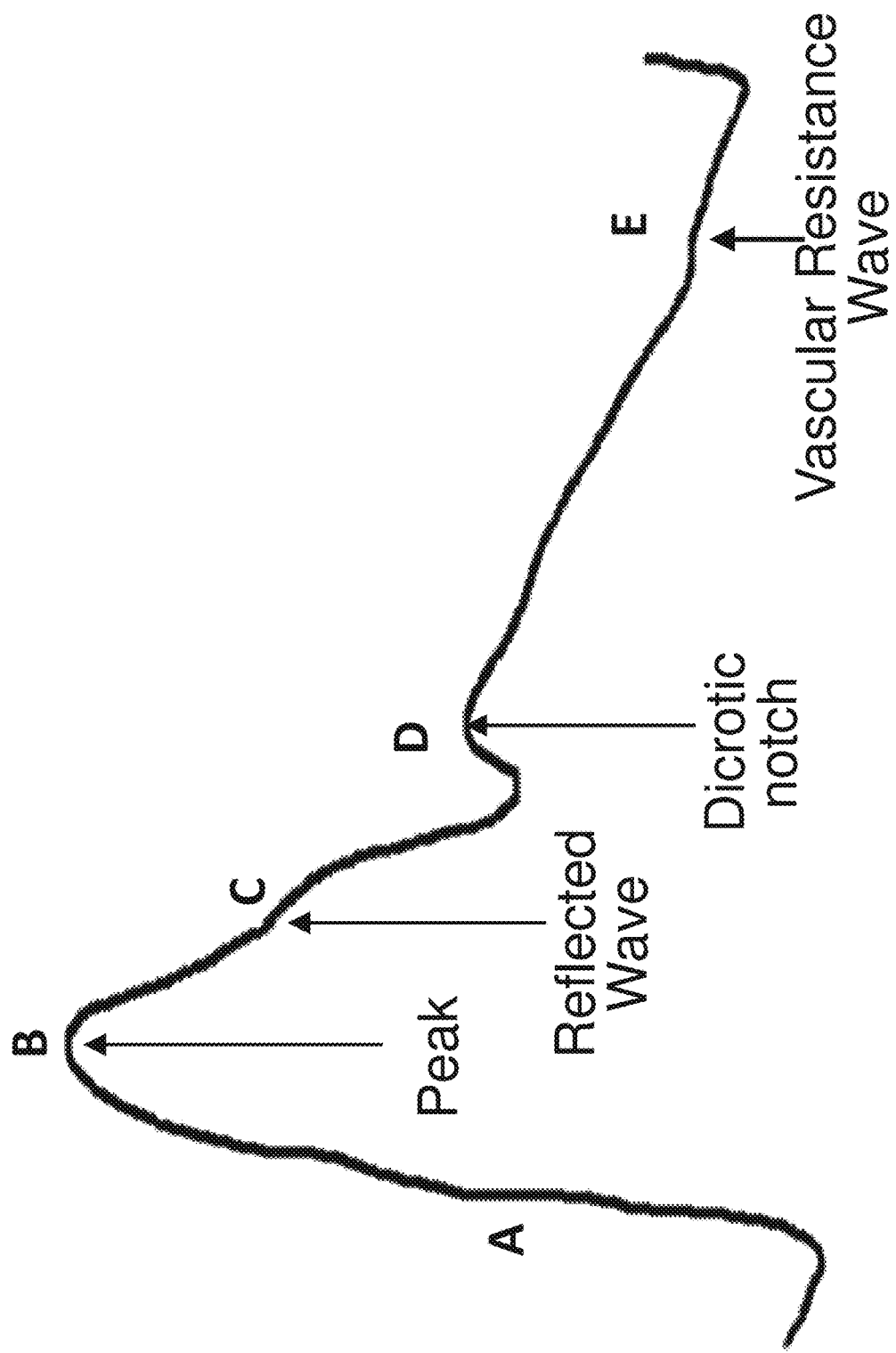
FIG. 2B shows a pulsatile wave-form.

With reference to FIG. 2A, it is noted that respiratory oscillations of the blood shear signal is an example of a sub-0.5 Hz physiological signal. Examples of sub-0.25 physiological signals are (i) myogenic oscillations of the blood shear signal; (ii) neurogenic oscillations of the blood shear signal.

Figure 1B:
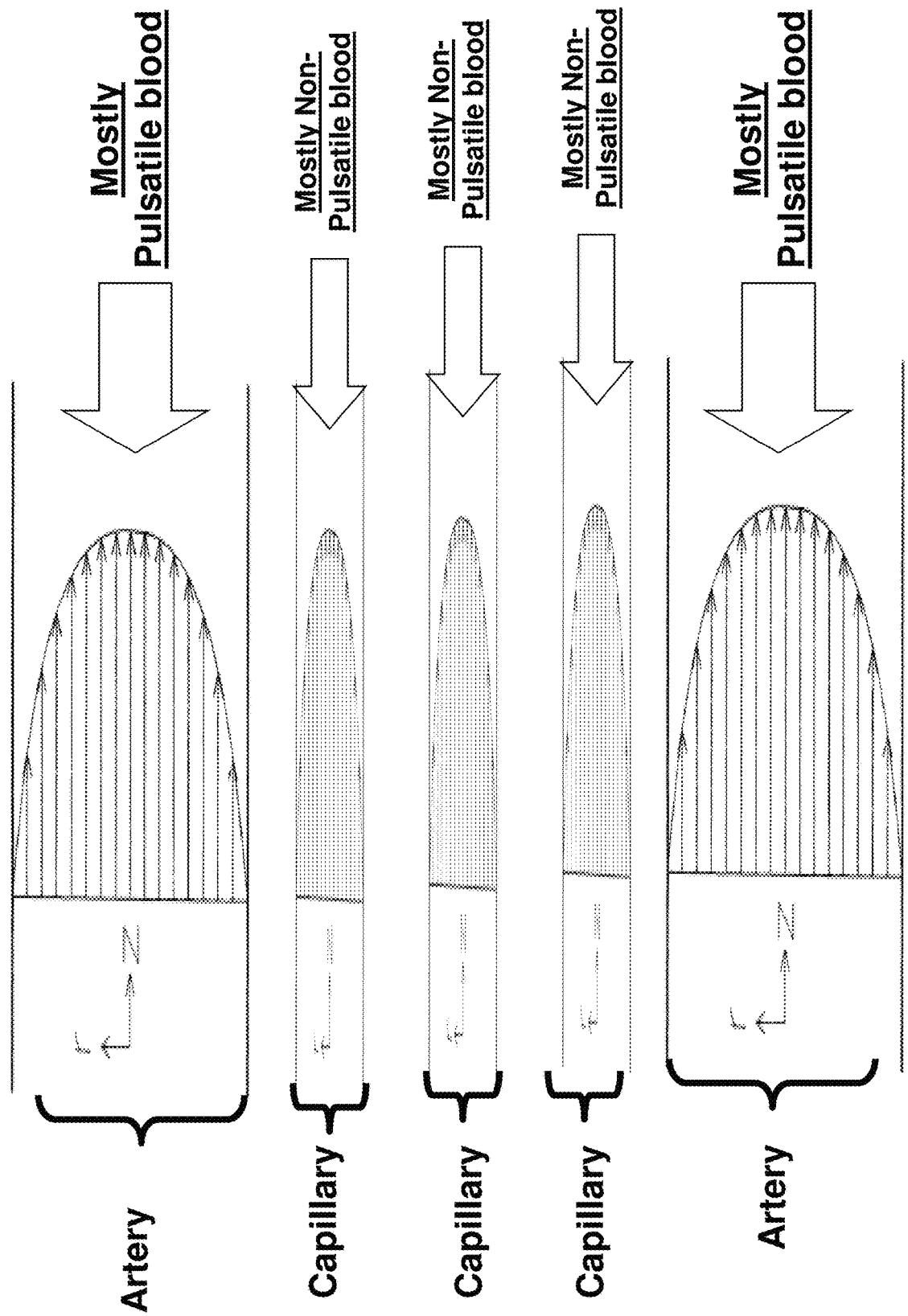

FIG. 11A illustrates one example of the results of performing the method of FIG. 10 in the context of a Stroop test. In this example, in step S359 a [4 Khz, 8 Khz] BSRD is generated in step S359, and subsequently this BSRD (which is, in fact, a pulsatile BSRD) is converted into a non-pulsatile BSRD by filtering out pulsatile frequencies thereof using a bandpass filter (step not shown in FIG. 10) to yield a non-pulsatile BSRD. This non-pulsatile BSRD corresponds to non-pulsatile physiological oscillations of blood shear in 'pulsatile blood' (see, for example, FIG. 1B). At that point, in step S363, the following 'target parameter P' is computed –P=normalized energy of the portion of the non-pulsatile BSRD signal in the [0.05 Hz, 0.15 Hz] range i.e. normalized relative to the magnitude of the non-pulsatile BSRD) of [0.05 Hz, 0.15 Hz] frequencies.

This was performed twice—once before the 'Stroop test' when the subject was in a relative 'low-stress state' and once 'during the troop test' (i.e when the subject is in a higher stress state due to the mental effort of the Stropp test)—this was performed on 42 subjects times and graphed in FIG. 11A is P(during test)–P(before test). As shown in FIG. 11A, most of the time for the post-Stroop-test (or 'stressed' person) the value of P increased as a result of the Stroop test (thus P(during test)–P(before test) is usually positive), indicating that a greater amount of normalized energy of the non-pulsatile BSRD in the [0.05 Hz, 0.15 Hz] frequency band is indicative of an 'elevated' mental stress state.

Figure 11B:
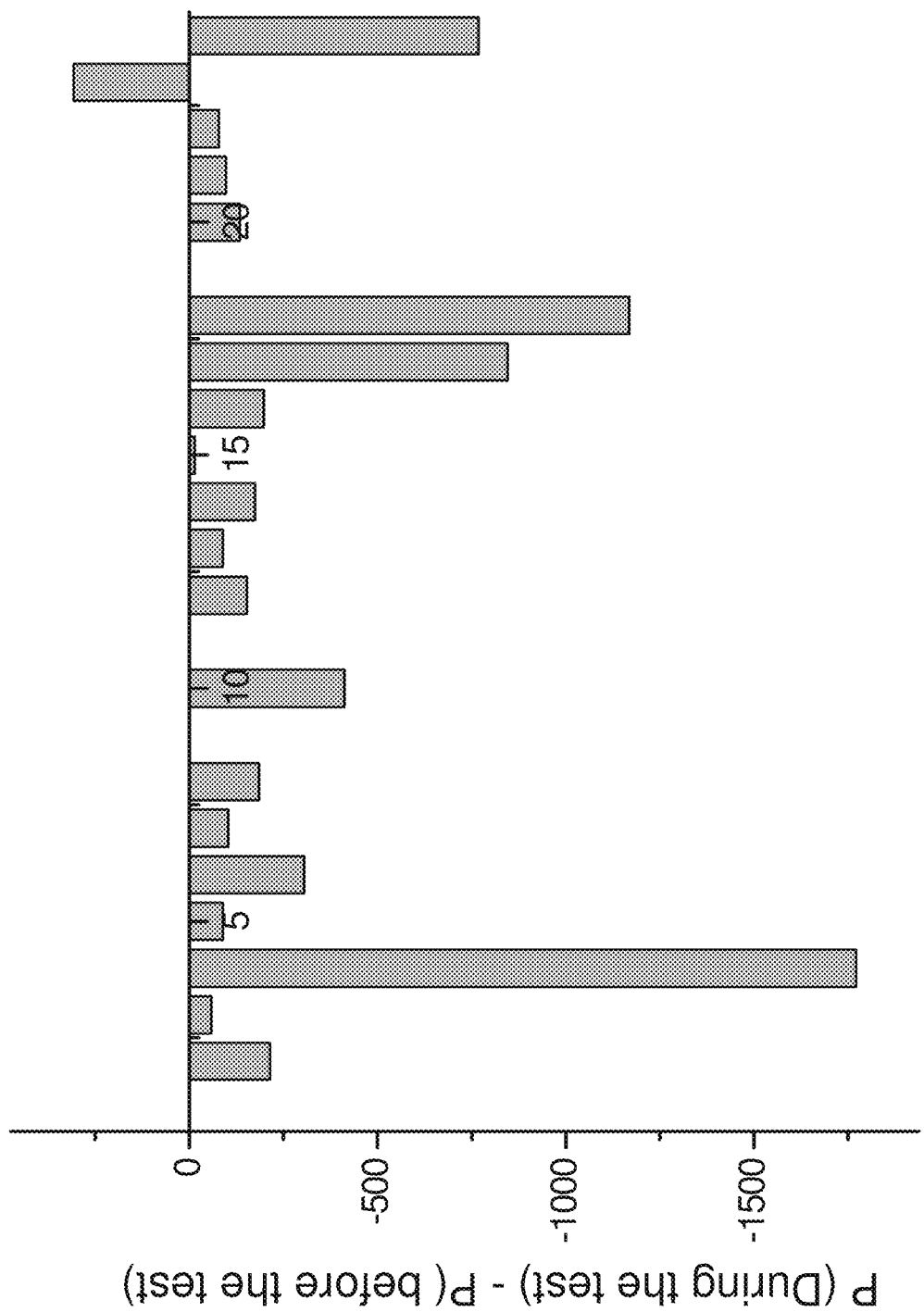

FIG. 11B illustrates one example of the results of performing the method of FIG. 10 in the context of detecting apnea events. In this example, in step S359 a [10 Khz, 24 Khz] BSRD is generated in step S359, and subsequently this BSRD (which is, in fact, a pulsatile BSRD) is converted into a non-pulsatile BSRD by filtering out pulsatile frequencies thereof using a band-pass filter (step not shown in FIG. 10) to yield a non-pulsatile BSRD. This non-pulsatile BSRD corresponds to non-pulsatile physiological oscillations of blood shear in 'pulsatile blood' (see, for example, FIG. 1B).

At that point, in step S363, the following target parameter P is computed—(ratio between (i) energy of the Mayer-frequency (i.e. in the frequency-band [0.05 Hz, 0.15 Hz] components of the BSRD to (ii) energy of the non-pulsatile BSRD in the [0.15, 0.7 Hz] frequency band.

This was performed twice—once before the 'Stroop test' when the subject was in a relative 'low-stress state' and once 'after the troop test'—this was performed on 42 subjects times and graphed in FIG. 10A is the delta P where P=normalized energy of the portion of the non-pulsatile BSRD signal in the [0.05 Hz, 0.15 Hz] range. As shown in FIG. 11A, most of the time for the post-Stroop-test (or 'stressed' person) the value of P increased as a result of the Stroop test, indicating that a greater amount of normalized energy of the non-pulsatile BSRD in the [0.05 Hz, 0.15 Hz] range is indicative of an 'elevated' mental stress state.

Figure 12B:
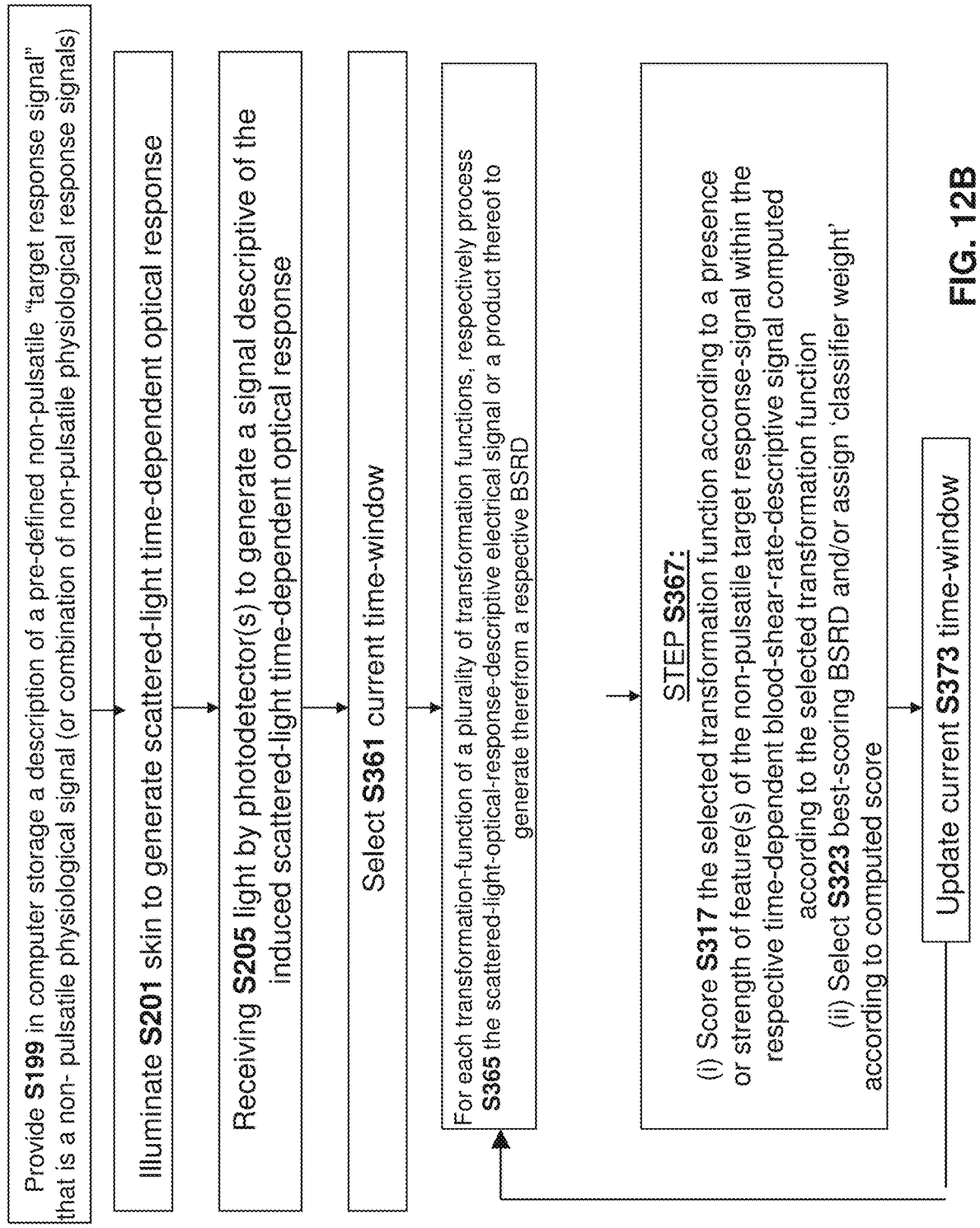
Figure 13:
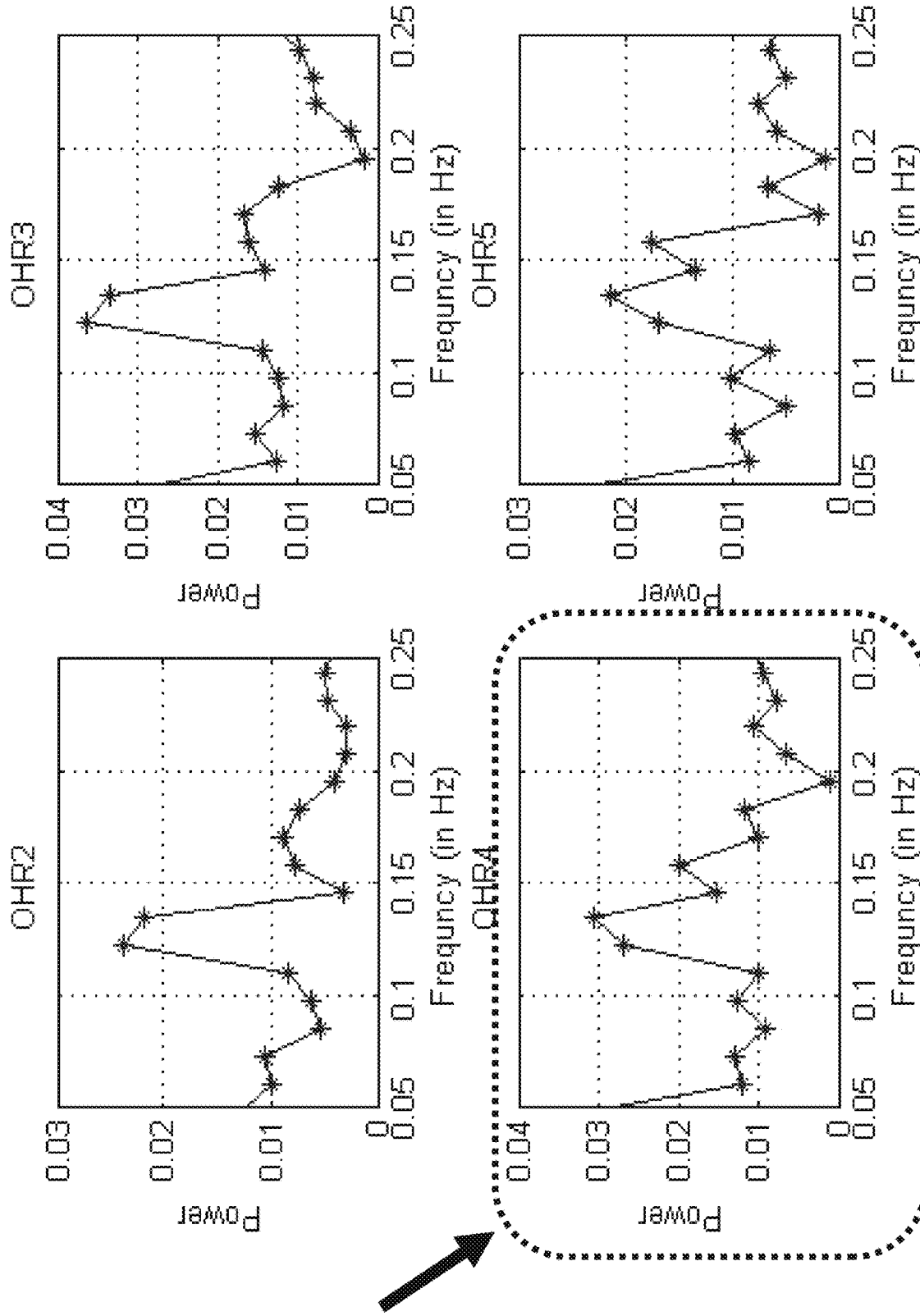

Description of FIGS. 12-14 (Computing Mood and/or Stress and/or Fitness and/or Emotion by Dynamically Computing a BSRD)

It is noted that there are many ways to transform a scattered-light time-dependent optical response signal and a BSRD signal, depending on the frequency selection profile. The biological meaning of a 'frequency selection profile' may relate to a type of blood (e.g. within arteries or capillaries, near the wall or near the centerline, etc) for which the BSRD signal is relevant. Thus, the optical response signal represents an 'ensemble' of blood vessels (and an 'ensemble' of locations therein)—the frequency selection profile for BSRD generation may relate to selection of vessels of the ensemble or locations within these vessels.

When trying to sense stress and/or mood, the optimal BSRD and/or frequency selection may vary between individuals or may vary for a single individual over time. Use of a sub-optimal BSRD (or sub-optimal weighting) may yield fail to capture the prevailing biological status of the subject and thus result in an inaccurate detection.

For any scattered-light-optical-response descriptive electrical signal, there are many ways to transform the scattered-light-optical-response descriptive electrical signal into a BSRD—each transformation may be associated with a different frequency-selection profile and would thus generate a different BSRD. In view of this relatively 'large number' of possible transformations, it is not always clear a priori which transformation will provide the most accurate prediction of a subject's stress-state and/or mood-state and/or emotion-state cardiovascular fitness parameter. The best mood and/or stress and/or emotion and/or fitness-predictor for one mammalian subject may not necessarily be the best for another subject—furthermore, the 'best predictor' may change over time.

In the example of FIG. 12, BSRDs are scored relative to a 'target physiological response signal' (e.g. Mayer wave) provided in step S199 in computer storage. As noted above, for the present disclosure, the term 'response signal' therefore relates to the response(s) to input and/or feedback from the central nervous system as manifested within blood flow As noted above with reference to FIG. 2B, a pulsatile signal has a known pre-determined signal form. Similarly, physiological response signals have known signal forms. This signal form may be in the time domain or in the frequency domain —thus, in some embodiments, a power frequency spectrum may be stored in step S199.

More than one BSRD may be generated (steps S309-S131) and the BSRD's (e.g. non-pulsatile BSRDs) may be scored (step S317) according to prominence of a sub-Hz physiological signal therein. Candidate BSRD signals are generated in step S309-S313, each candidate BSRD signal may be 'scored' (see step S317) and the scores may be compared to each other (step S323).

FIG. 13 (discussed below) relates to an example technique for scoring a 'candidate BSRD' according to prominence of a Mayer wave therein—this technique is one example of the scoring of step S317 of FIG. 12A and of step S367 of FIG. 12B.

In one example, the 'target non-pulsatile physiological signal (i.e. selected in step S199) may be a one example is a Mayer wave). Thus, FIG. 13 illustrates one example for how to 'score' a BSRD (e.g. non-pulsatile BSRD) in step S317 of FIG. 12.

In particular, FIG. 13 relates to the case where the 'physiological response signal' is a Mayer wave and a form of this signal in the frequency form is analyzed. Four candidates are illustrated in FIG. 13—each candidate represents a power spectrum of the BSRD and the arrow points to the 'highest scoring' candidate of the four candidate—i.e. having a power spectrum functional form that closest matches that of a Mayer wave. As noted above, a Mayer wave is just one example of a response signal.

As illustrated in FIG. 12, in step S323 the better scoring BSRD may be preferred (e.g. afforded a greater weight) to the lower scoring BSRDs.

FIG. 12 is one example of a 'dynamic' generation of BSRD. In one example, the 'dynamic generation' may relate to comparing multiple candidates.

As noted above, it is not often clear a priori which transformation function yields the best results. Furthermore, even for the same subject, the best-scoring transformation function may fluctuate in time—i.e. for an earlier time-period a first transformation function yields the 'highest score' while for a later time-period a second transformation function yields the 'highest score.'

Figure 14A:
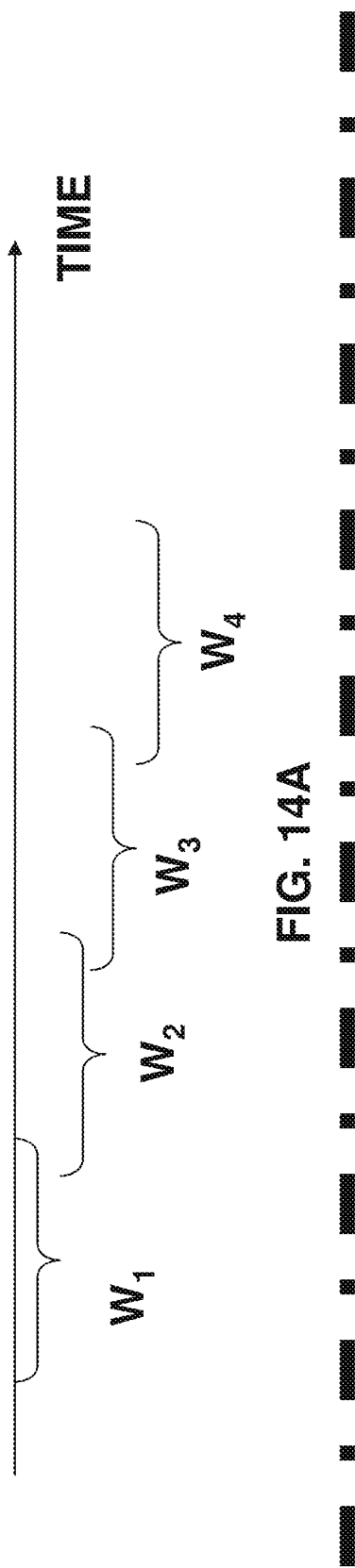
FIGS. 14A-14B show time windows.
Figure 14B:
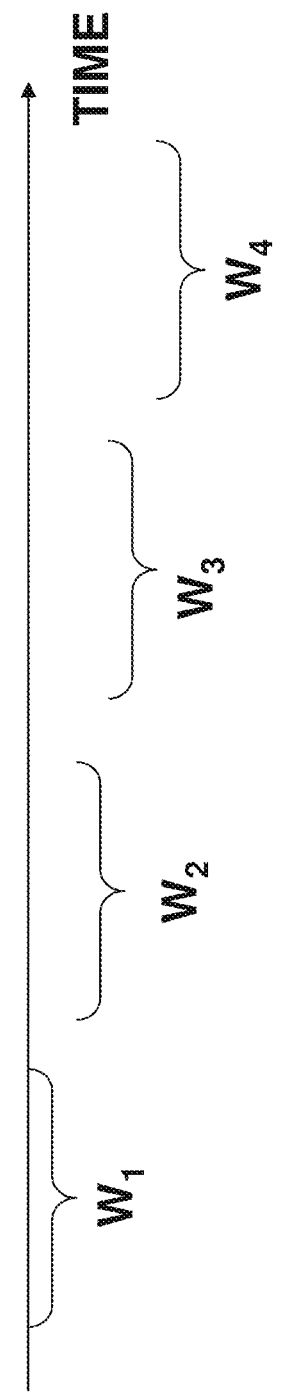

Time periods may be defined according to time windows—see FIG. 14A which illustrates overlapping time-windows and FIG. 14B which illustrates non-overlapping time-windows.

FIG. 12B is an example of a method for processing a scattered-light time-dependent optical response signal into a BSRD (e.g. non-pulsatile BSRD) according to a dynamic and responsive technique which periodically updates the transformation function (i.e. selected from a 'family' of functions) in order to optimize a 'score' of the time-dependent blood-shear-rate descriptive signal where the 'score' describes prominence.

Thus, in step S361 after a time window is selected, instead of applying only a single transformation function for processing (i.e. for the particular time window) the scattered-light time-dependent optical response signal into a BSRD, it is possible to perform the transformation a number of times—each time, the transformation is performed using a different transformation function (i.e. associated with a different respective 'frequency-selection profile). The results are scored in step S367—i.e. as discussed above with reference to step S317 of FIG. 12A, candidate BSRDs where a prominence of the non-pulsatile target signal (e.g. Mayer wave) within the candidate BSRD may be assigned a greater score than candidate (e.g. the 'best-scoring' time-dependent blood-shear-rate descriptive signal is employed when computing therefrom the mood and/or emotion and/or stress and/or cardiovascular fitness parameter.

The time window is updated in step S373. For each time window, the 'best' transformation function may be different—therefore, the transformation between scattered-light time-dependent optical response signal into a time-dependent blood-shear-rate descriptive signal is said to be performed dynamically in response to scoring for presence and/or strength of features of the non-pulsatile physiological signal of step S199

FIG. 13 (discussed below) relates to an example technique for scoring a 'candidate BSRD' according to prominence of a Mayer wave therein—this technique is one example of the scoring of step S317 of FIG. 12A and of step S367 of FIG. 12B.

The 'Mayer wave' is just one example of the non-pulsatile physiological signal of step S199. Other examples may include a signal describing a neurogenic contribution to oscillations/fluctuations of blood shear in blood vessel(s) (or locations therein) and a respiratory contribution to oscillations/fluctuations of blood shear in blood vessel(s) (or locations therein).

A Discussion of FIGS. 15A-15B, 16 and 17

As noted above, (i) BSRDs different from each other according to frequency selection profile used to generate each BSRD from the signal descriptive of the induced scattered-light time-dependent optical response; and (ii) because of the many different possible frequency selection profiles, there are fundamental differences between the different BSRDs.

Figure 15A:
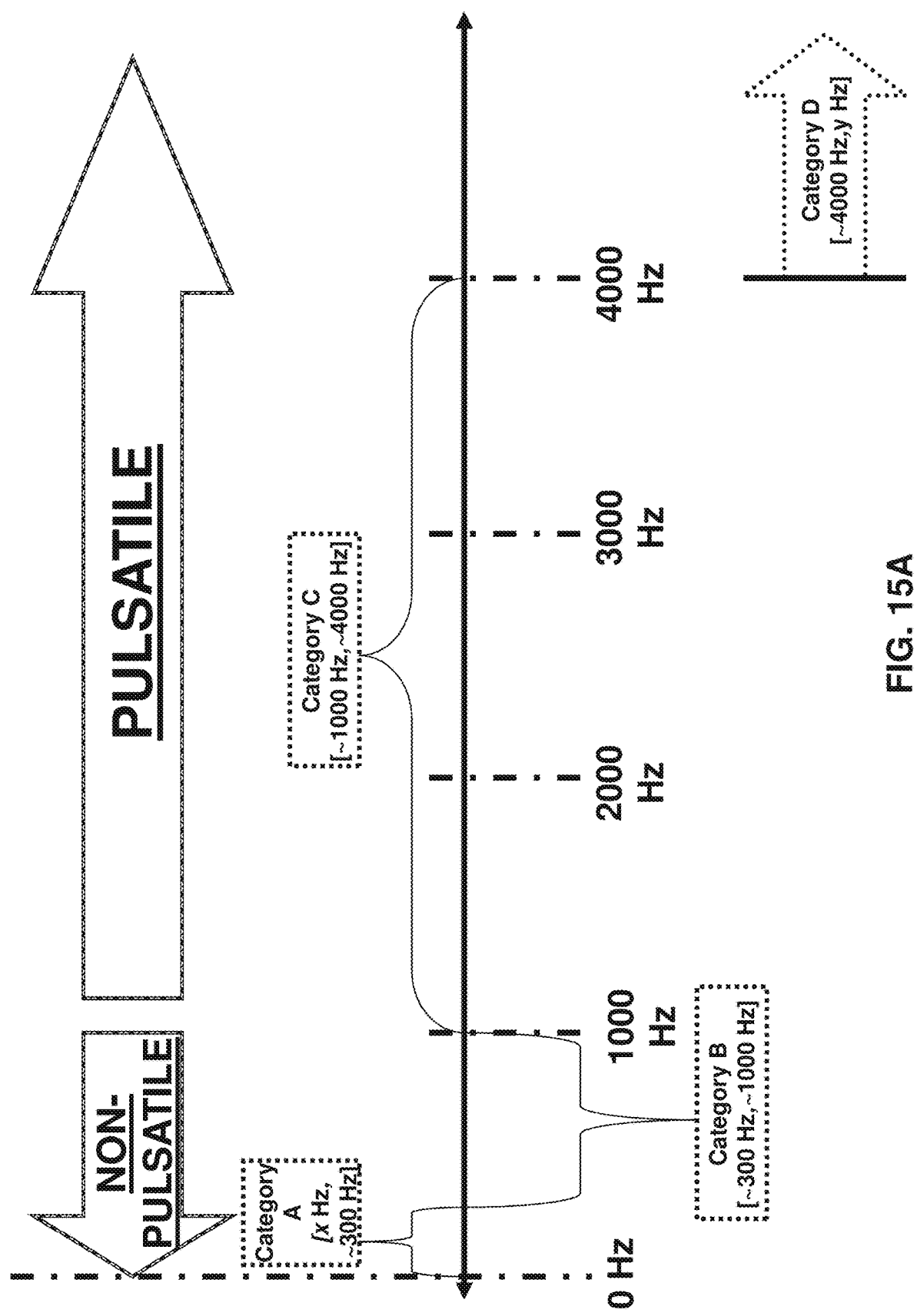
FIG. 15A illustrates four categories of BSRDs.

FIG. 15A relates to four categories of BSRDs: (i) a first category—'category A' where a value of x is at most 300 Hz or at most 275 Hz or at most 250 Hz or at most 200 Hz or at most 150 Hz or at most 100 Hz) of [x Hz, ~300 Hz] BSRDs; (ii) a second category—'category B' of [~300 Hz, ~1000 Hz] BSRDs (iii) a third category—category—'category C' of [~1000 Hz, ~4000 Hz] BSRDs; and (iv) a fourth category—category—'category D' of [~4000 Hz, z Hz] BSRDs where in different embodiments of z is at least 5000 or at least 6000 or at least 7500.

Unless the BSRDs are post-processed to filter out pulsatile components, the category D BSRDs tend to be dominated by pulsatile components. In different embodiments, category BSRDs tend to be descriptive of blood sheer in arterial blood at locations distanced from the walls, where blood tends to be pulsatile.

Figure 15B:
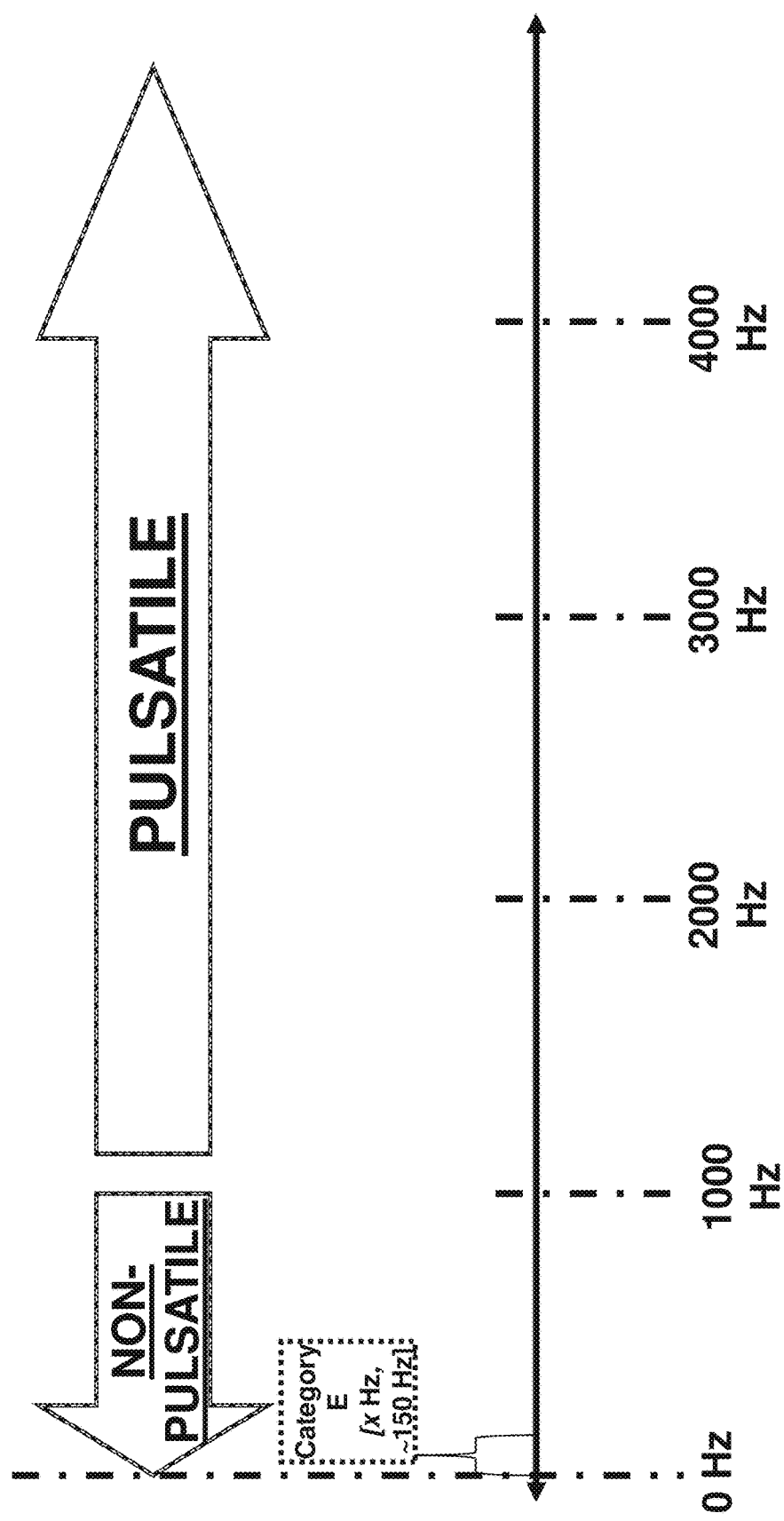
FIG. 15B illustrates a 'category E' BSRD.

FIG. 15B relates to a 'category E' [y Hz, ~150 Hz] BSRD where a value of x is at most 100 Hz or at most 75 Hz or at most 50 Hz. In some embodiments, a 'category E' BSRD is analyzed. For the present disclosure ~150 Hz is at most 250 Hz or at most 200 Hz or at most 175 Hz and at least 75 Hz or at least 100 Hz or a least 125 Hz.

In contrast, in some embodiments the low-frequency-dominated (and non-pulsatile category A BSRD tend to be derived primarily from light reflected off of slow-moving red blood-cells (RBSs) in endothelial blood flow and/or at locations close to the walls. Category B BSRDs also tend to be non-pulsatile, though to a lesser extent than Category A BSRDs. With reference to FIG. 16, consider two category B BSRDs deride from the same—a first category B BSRD having a frequency selection profile $[\alpha, \beta_1]$ at the top of FIG. 16 and a second category B BSRD having a frequency selection profile $[\alpha, \beta_2]$ at the bottom of FIG. 16 where (i) $\alpha$ is ~300 Hz; (ii) both $\beta_1$ and $\beta_2$ are ~1000 Hz, and (iii) $\beta_1 > \beta_2$, for example, $\beta_1 - \beta_2 > 50$ Hz. In this case, the energy of the 'first' category B BSRD exceeds that of the 'second' category B BSRD—however, the 'first' category B BSRD is 'more pulsatile' than the 'second' category B BSRD because at frequencies of ~1000 Hz as the frequency increases more pulsatile components are introduced into the BSRD.

Figure 17:
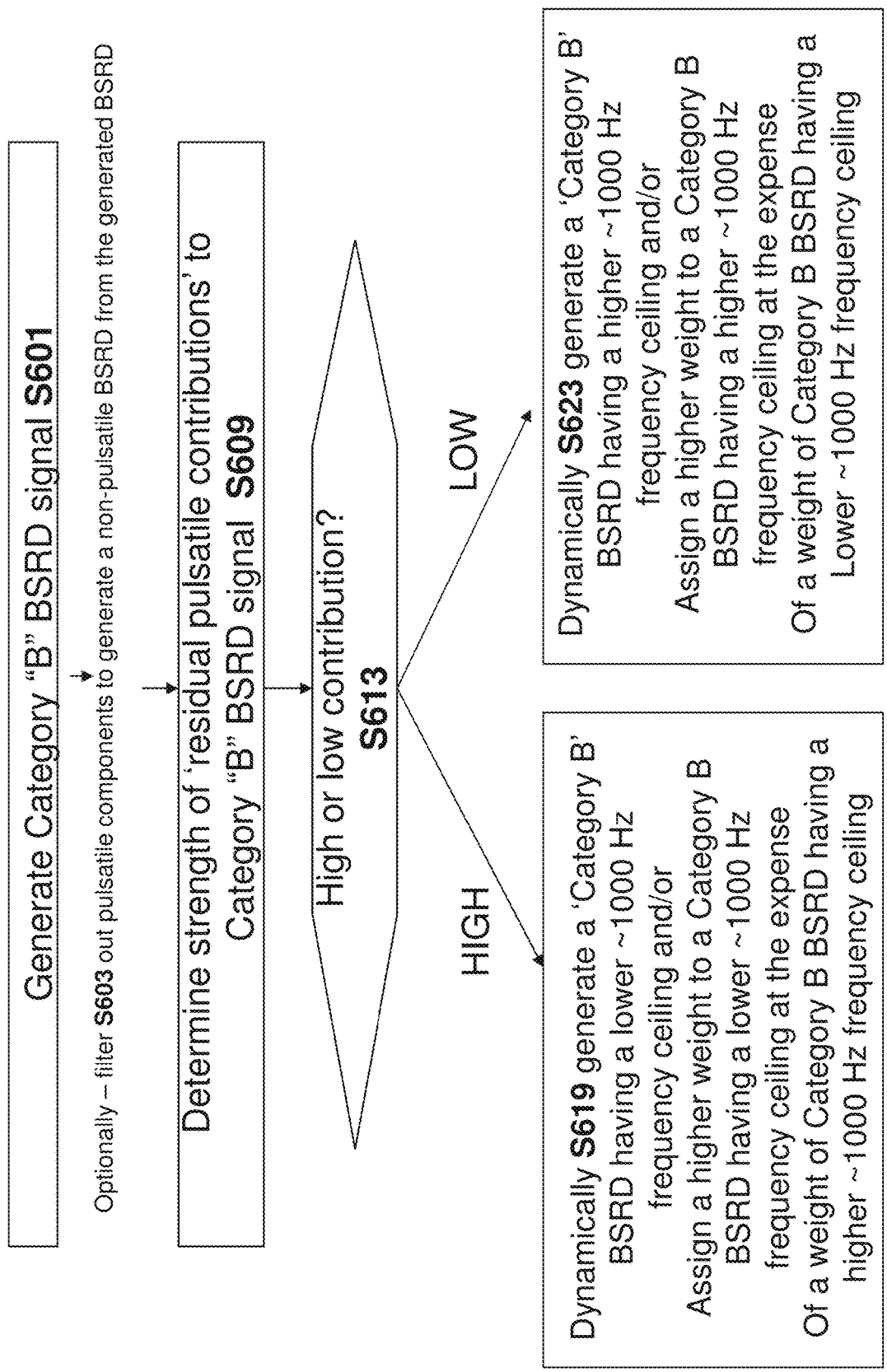

Reference is made to FIG. 17. In some embodiments, it is possible to dynamically generate (i.e. where the frequency profile is dynamically selected) a category BSRD signal B signal and to compute therefrom an emotion and/or mood and/or stress and/or cardiovascular fitness parameter. Thus, in step S601 a category B BSRD signal having a frequency selection profile $[\alpha, \gamma]$ is generated and in step S609-S613 a strength of residual pulsatile contributions to the category B BSRD signal is computed—for example, the contribution of a signal of FIG. 2B having the pulsatile wave form to the category B BSRD signal having a frequency selection profile $[\alpha, \gamma]$. If the contribution is relatively 'low' then in step S623 it is possible to generate a category B BSRD having a higher value of $\gamma$—in this case, there is less of a 'concern' about 'noisy' pulsatile components 'polluting' the category B BSRD signal and it is preferable to generate a category B BSRD signal having a greater total energy from which to derive the subject's motion and/or emotion and/or mood and/or fitness parameter. Conversely, if the contribution is relatively 'high' (indicating a 'noisy' category B signal) then in step S619 it is possible to generate a category B BSRD having a lower value of $\gamma$ to reduce the 'puslatile noise'—in this case, because there is more of a 'concern' about 'noisy' pulsatile components 'polluting' the category B BSRD signal, it is preferable to take steps to reduce the 'pulsatile noise' even if the 'price paid' is a category B BSRD signal having a lesser total energy. The subject's motion and/or emotion and/or mood and/or fitness parameter is computed from the 'lower gamma' category B signal.

Figure 16:
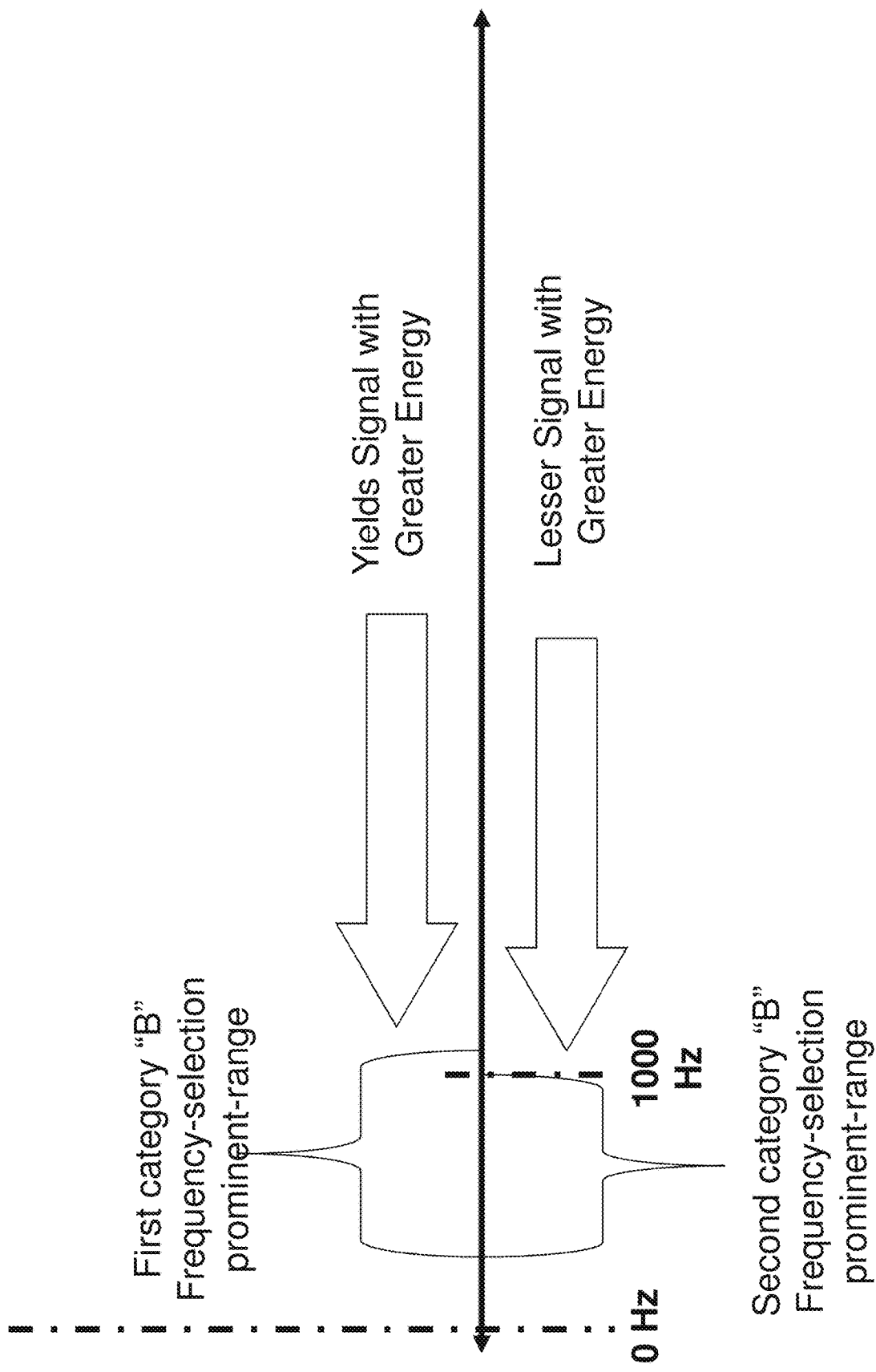

Similar to the method of FIG. 12, the method of FIG. 16 relates to the dynamic generation of a BSRD in accordance with analysis of BSRD feature(s). Thus, the discussion above with reference to FIGS. 14A-14B may apply with respect to the method of FIG. 16 mutatis mutandis.

Figure 18A:
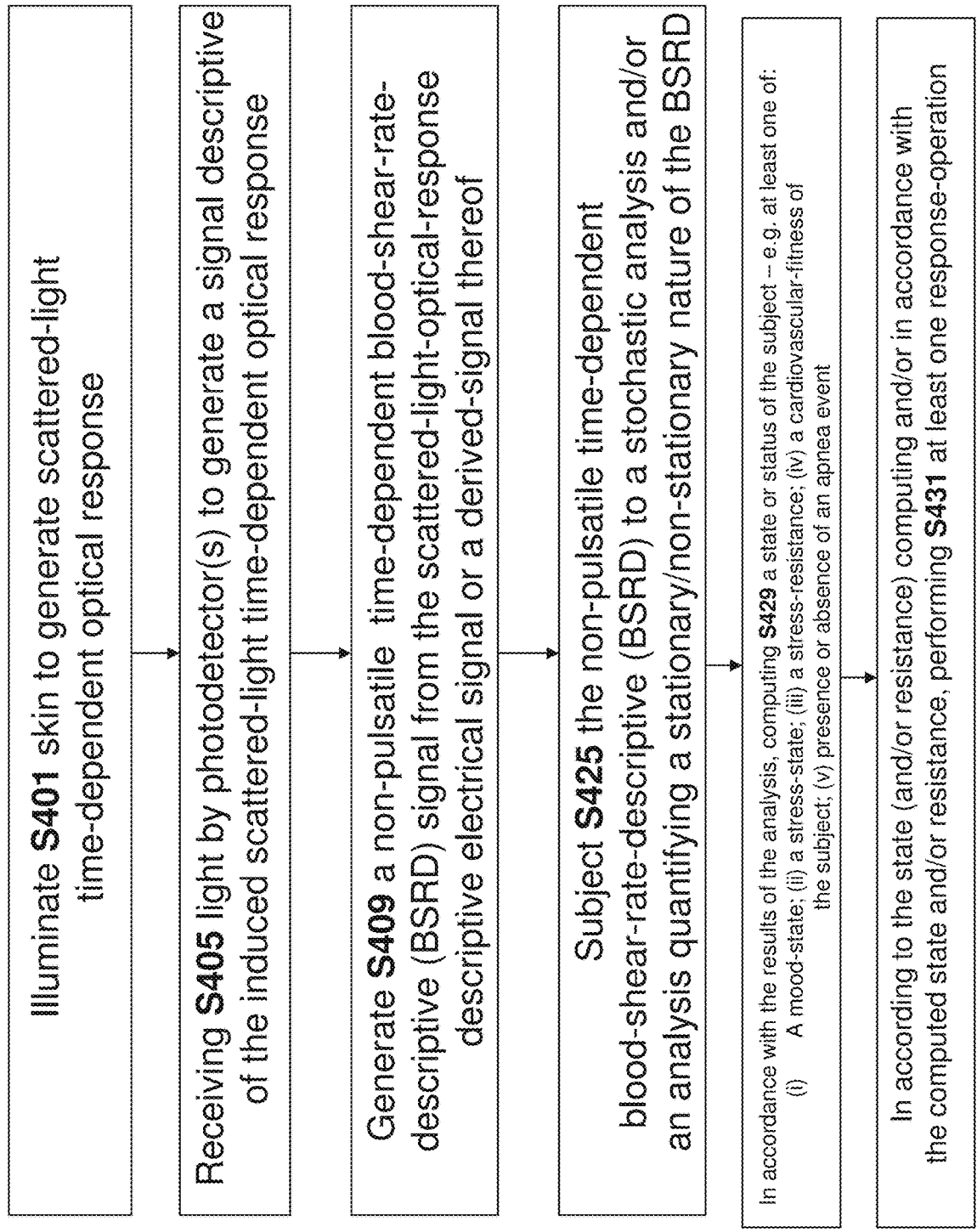
Figure 18B:
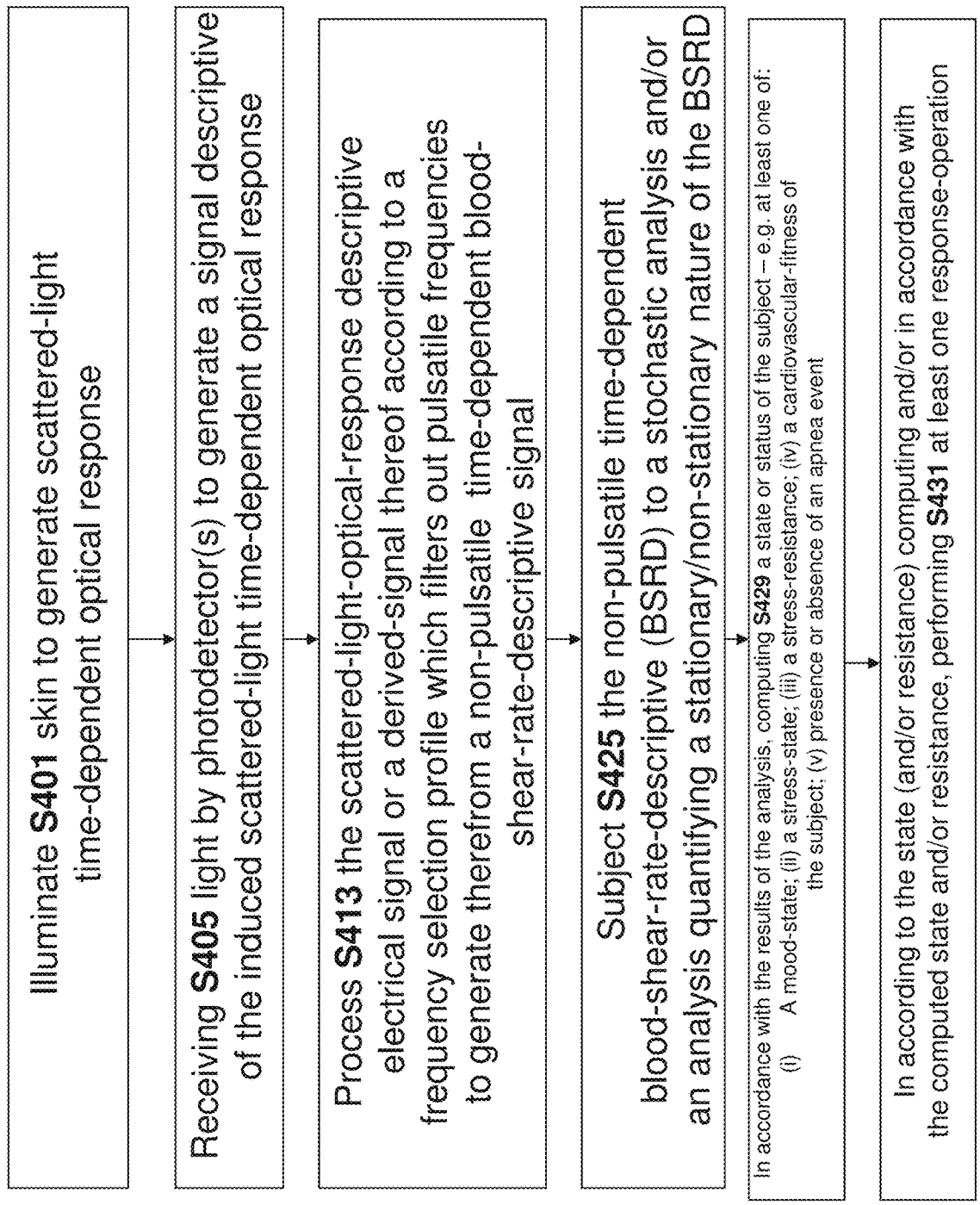
Figure 18C:
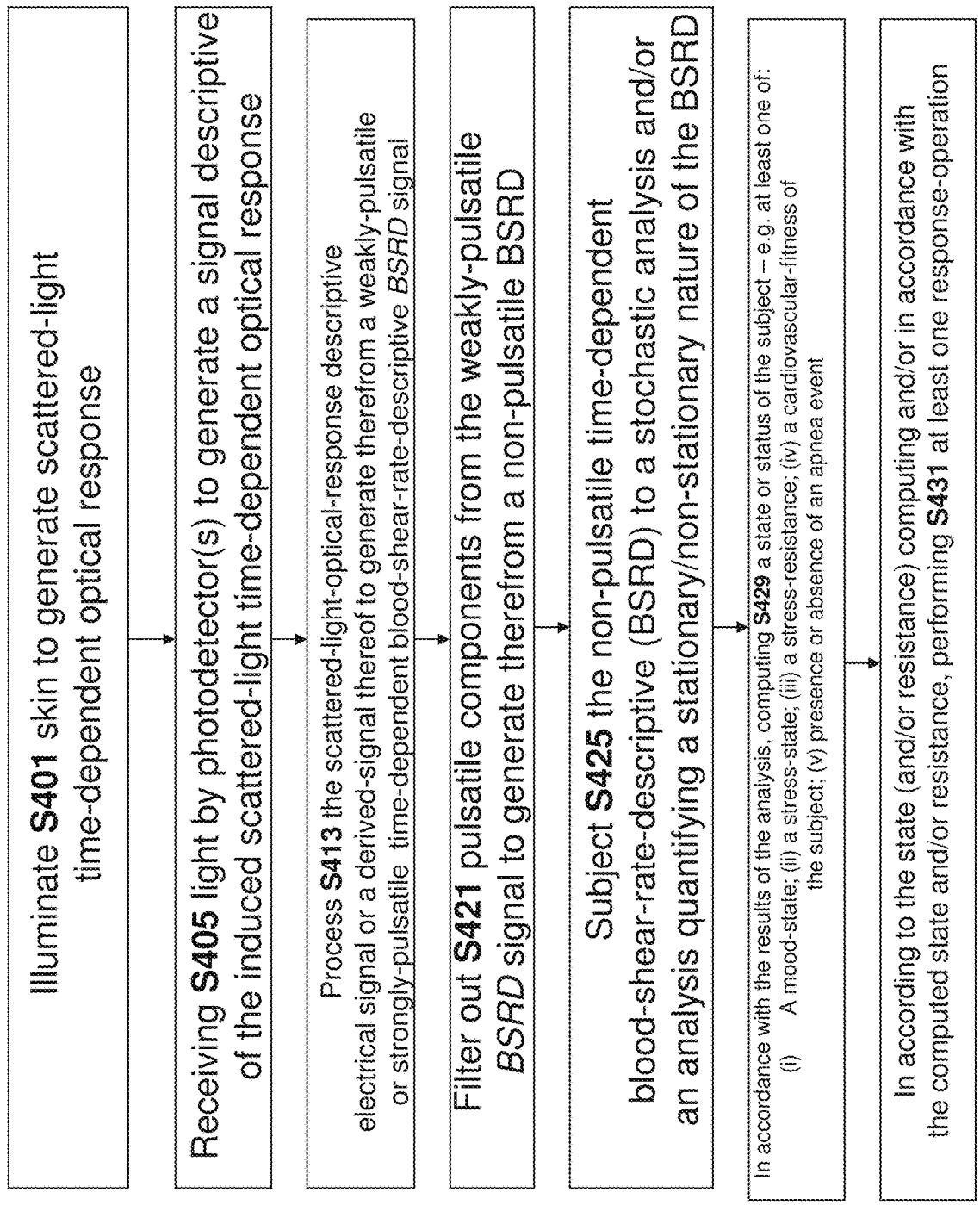

A Discussion of FIGS. 18A-18C

FIGS. 18A-18C relates to method whereby (i) a non-pulsatile BSRD is subjected, in step S425, to a stochastic analysis and/or an analysis quantifying a stationary/non-stationary nature of the non-pulsatile BSRD; and (ii) according to the results of the subjecting, emotion and/or mood and/or stress and/or cardiovascular fitness parameters (or a classification) of a type of stress is computed in step S429.

For example, when the subject's stress-level changes this may modify the balance between competing vasoconstrictors and vasodilators, yielding stochastic behavior.

One example of such stochastic analysis is computing a fractal dimension of the non-pulsatile BSRD signal. Another example is computing a Hurst exponent. In another example, an entropy of the non-pulsatile BSRD signal is quantified.

In steps S401-S409 of FIG. 18A, this non-pulsatile BSRD is generated by scattering light off of red blood cells to generate a scattered-light time-dependent optical response (step S401-S405)—in step S409 the non-pulsatile BSRD is computed directly or indirectly from the scattered-light time-dependent optical response.

For example, as illustrated in step S413 of FIG. 18B, the non-pulsatile BSRD may be computed by selecting the appropriate frequency-selection profile—e.g. $[\alpha,\beta]$ where $\beta <= \sim 1000$ Hz. Alternatively, in the example of FIG. 18B, a pulsatile BSRD (e.g. a weakly pulsatile BSRD (e.g. a 'category C' BSRD) is computed or a strongly pulsatile BSRD (e.g. a 'category C' BSRD) is computed). In step S421, the pulsatile components (i.e. having a signal-form like that illustrated in FIG. 2B) are filtered out of the pulsatile BSRD yielding the non-pulsatile BSRD In some embodiments, one difference between the method of FIG. 18B and FIG. 18A are that they extract different types of non-pulsatile flow information—the method of FIG. 18B extract information from non-pulsatile blood (e.g. within capillaries or endothelial flow blood) while FIG. 18C extracts non-pulsatile information from pulsatile blood by filtering out the pulsatile signal which 'masks' this non-pulsatile information.

Figure 19:
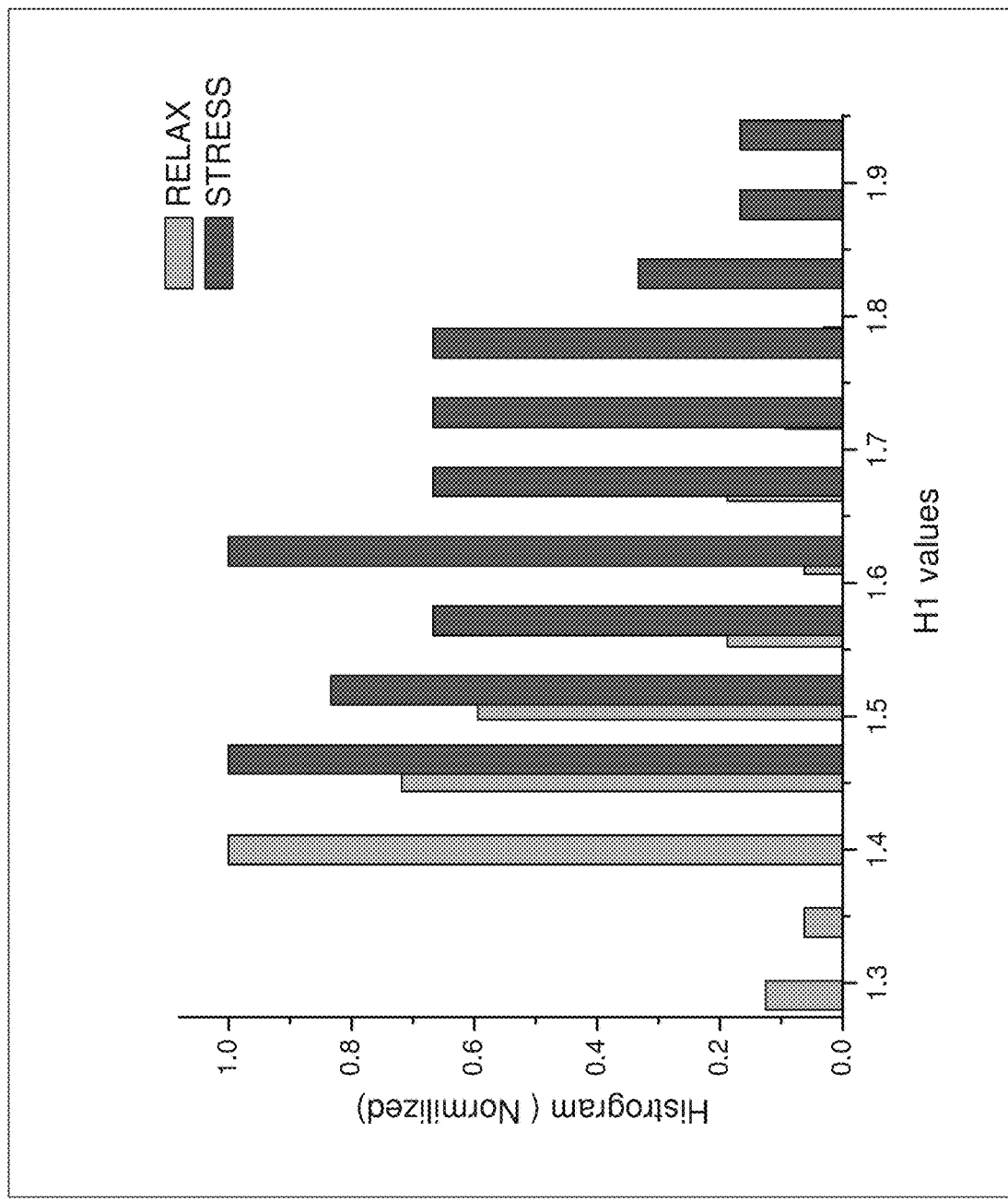

FIG. 19 illustrates one example of the results of performing the method of FIG. 18 in the context of a sound test. In this example, in step S409 a [0 Khz, 400 Khz] BSRD is generated. In step S425, the following 'target parameter P' is computed –P=Hurst exponent of the non-pulsatile BSRD signal generated in step S409. The experiment was the 'sound test'—i.e. subjecting the people of the test to an unpleasant sound and observing the physiological consequences (i.e. within blood flow) of the ensuing stress resulting from the unpleasant sound.

This computing of the 'target parameter P' was performed twice—once before the 'sound test' when the subject was in a relative 'low-stress state' and once 'during the sound test' (i.e when the subject was in a higher stress state due to)—this test was performed 135 times where the. FIG. 19 illustrates a histogram of the results where the 'lighter bars' represent 'relaxed states' and the darker bars represent the stressed state (i.e. after the subjects hear the unpleasant and stress-inducing sound). As shown in the graph, the parameter P can differentiate between the 'relaxed' and 'sound-stressed' individuals.

FIG. 20 illustrates one example of the results of performing the method of FIG. 18 in the context of a cardiovascular fitness test. In this example, in step S409 a [400 Khz, 400 Khz] BSRD is generated. In step S425, the following 'target parameter P' is computed –P=Hurst exponent (chaos indication) of the non-pulsatile BSRD signal generated in step S409 of the person in the 'stating state' minus Hurst exponent (chaos indication) of the non-pulsatile BSRD signal generated in step S409 of the person in the 'supine state'. The orthostatic test' experiment (cardiovascular fitness parameter) was-steps S409 and S425 were performed for a signal generated when the subject was supine (i.e. step S401-S405 were performed when the subject was supine) and again when the subject was standing.

Figure 20A:
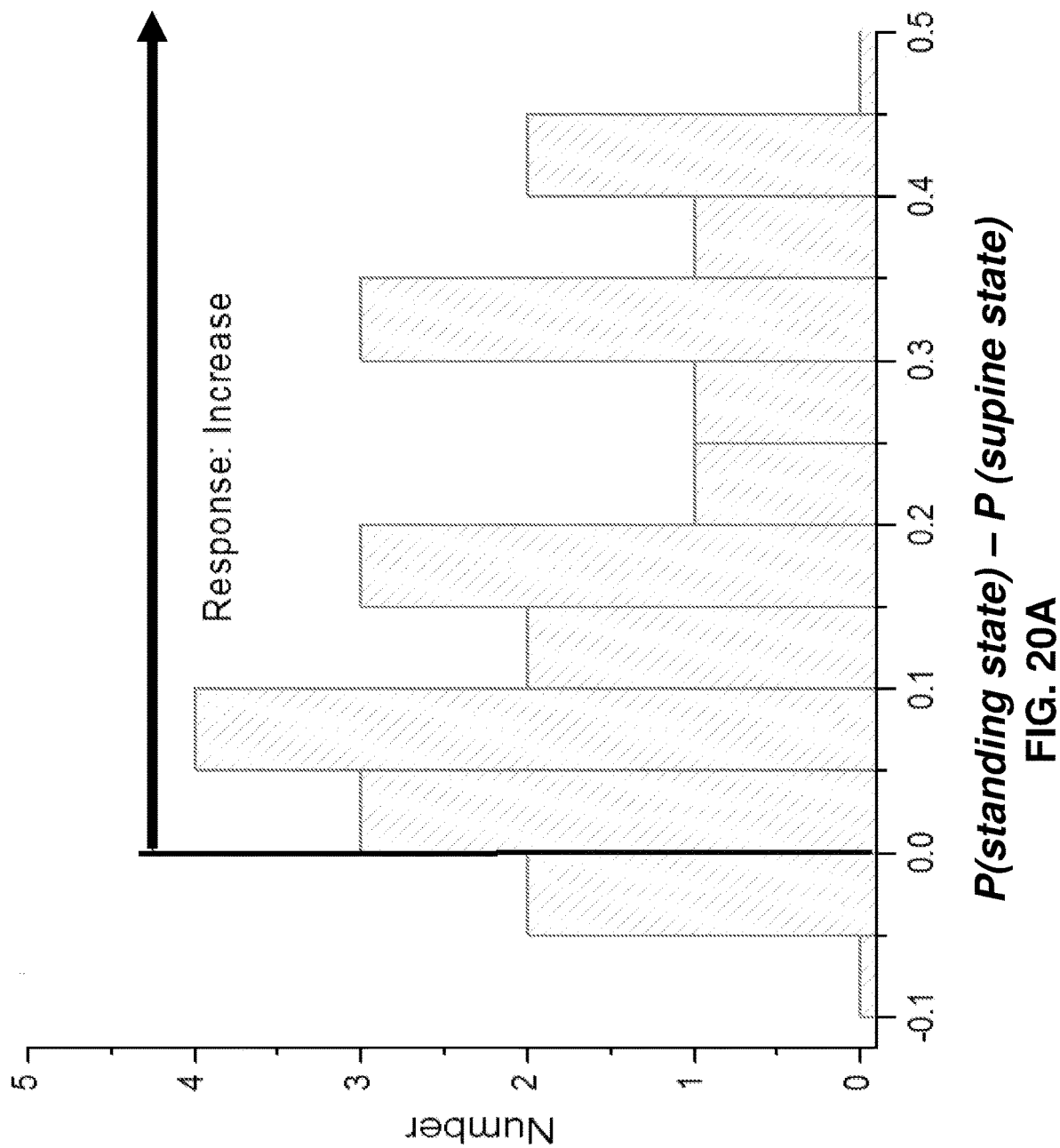
Figure 20B:
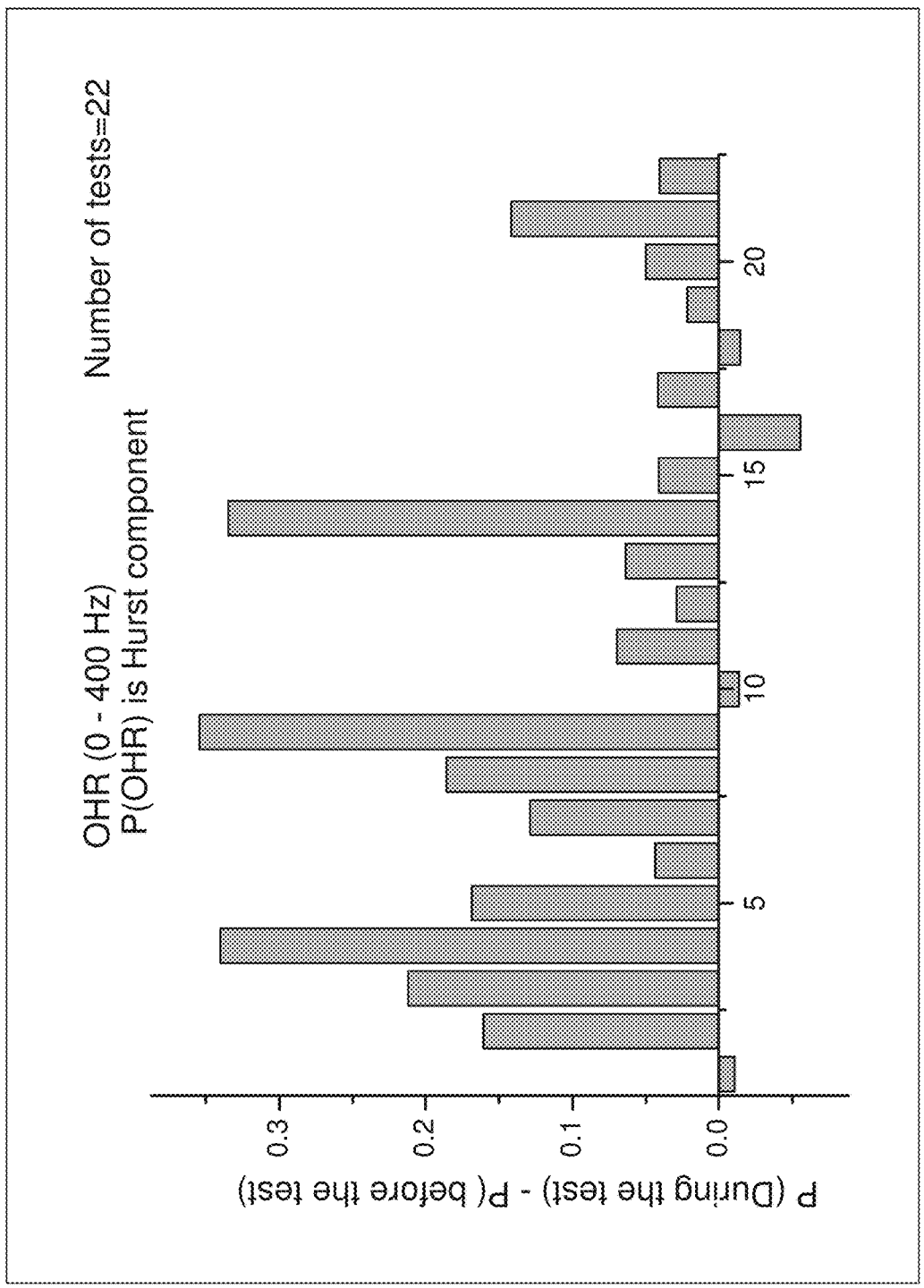

FIG. 20A is a histogram of the results (test performed 43 times one per person)—most of the time the Hurst coefficient increases. FIG. 20B is a histogram of other results (test performed 22 times one per person)—most of the time the Hurst coefficient increases. In FIG. 20B P before test is the Hurst exponent for when the subject was supine and P after the test is the Hurst exponent for when the subject was standing.

Figure 21A:
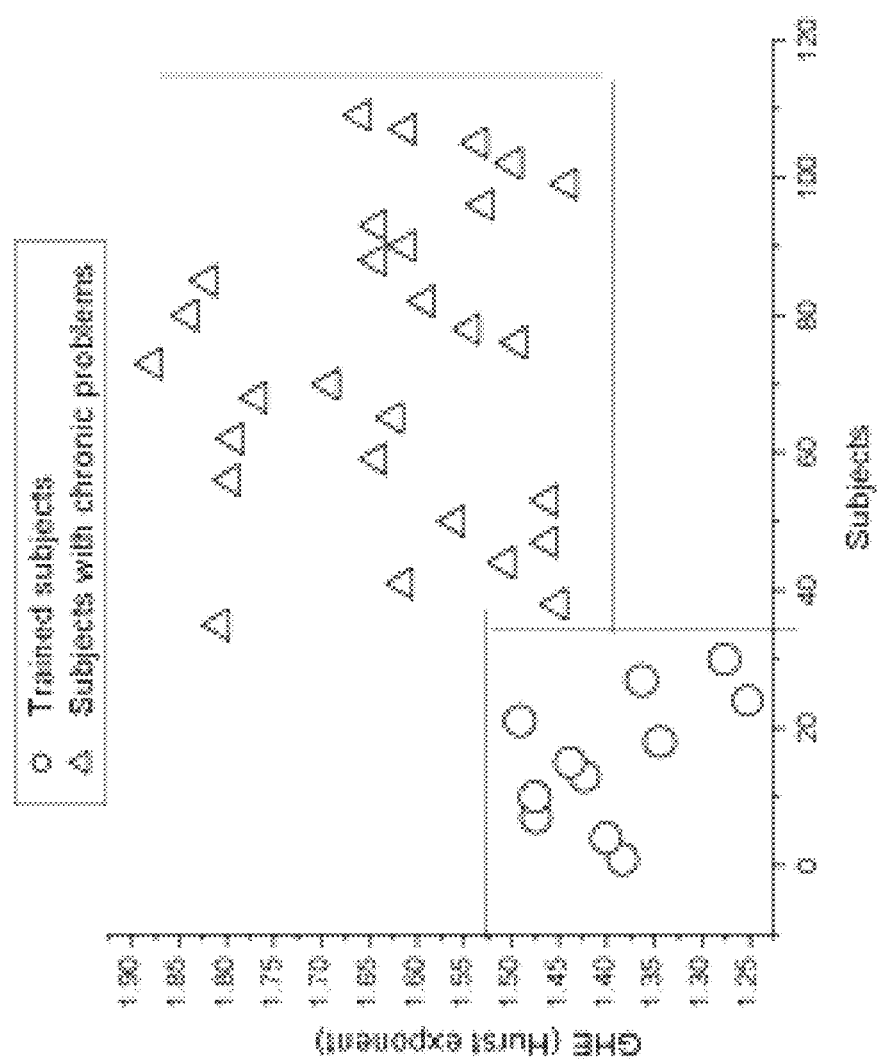
Figure 21B:
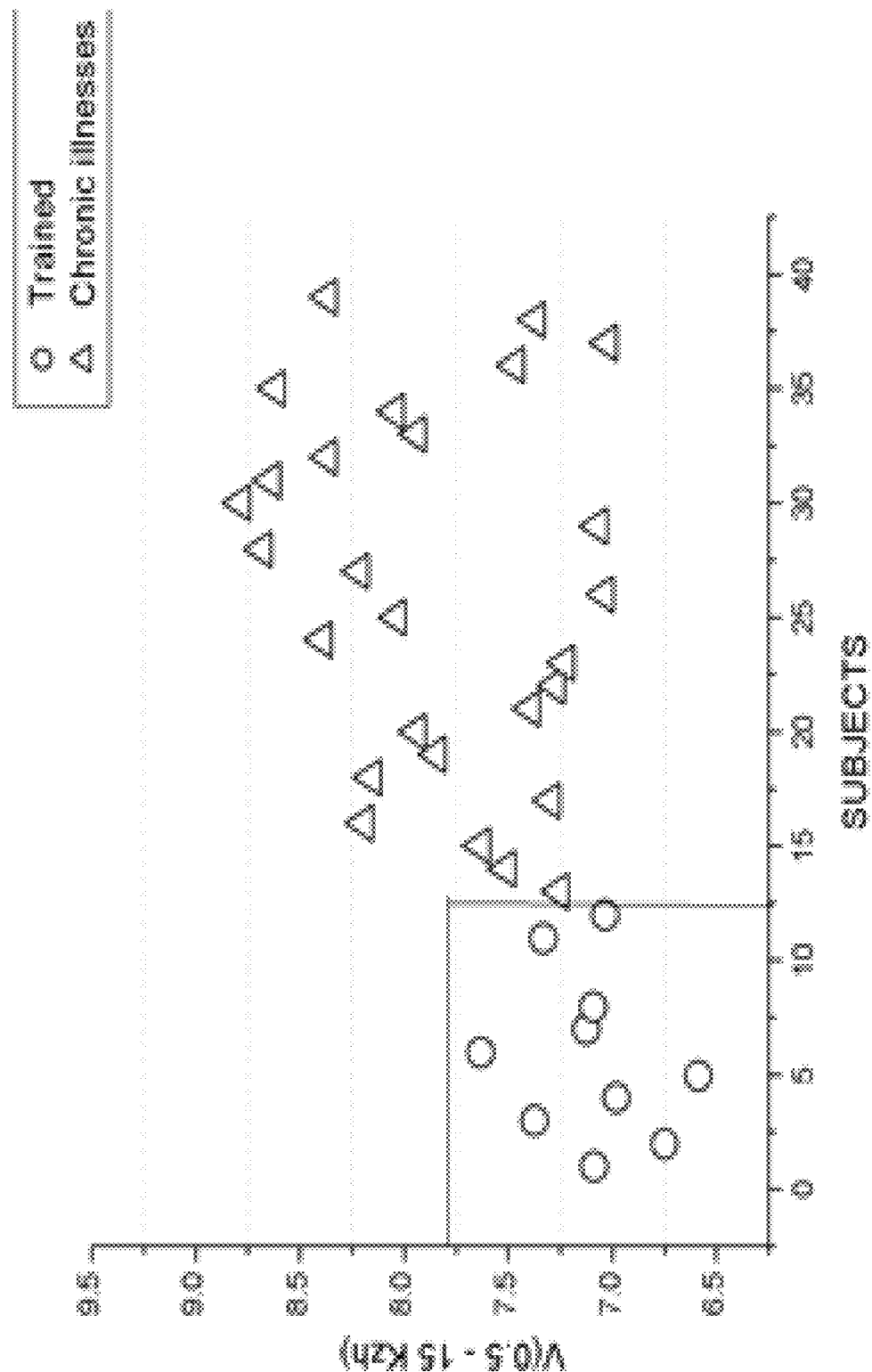

FIGS. 21A-21B illustrate another example of a parameter generated according to FIG. 18—the tests are performed for two groups of subjects—one group of 'trained' or physically fit subjects (in the circle) and another group for has a chronic problem. Each subject had a unique number (on the x axis) and a particular parameter (on the y axis) was computed in step S425. Each result is thus its own data point—the results are graphed in FIGS. 21A-21B.

Discussion of FIGS. 22-25

In the discussion above with reference to FIG. 15, four types of BSRDs were discussed: (i) extremely non-pulsatile category A BSRDs; (ii) non-pulsatile category B BSRDs which may include very weak pulsatile components; (iii) weakly pulsatile category C BSRDs and (iv) strongly pulsatile category D BSRDs.

Figure 22A:
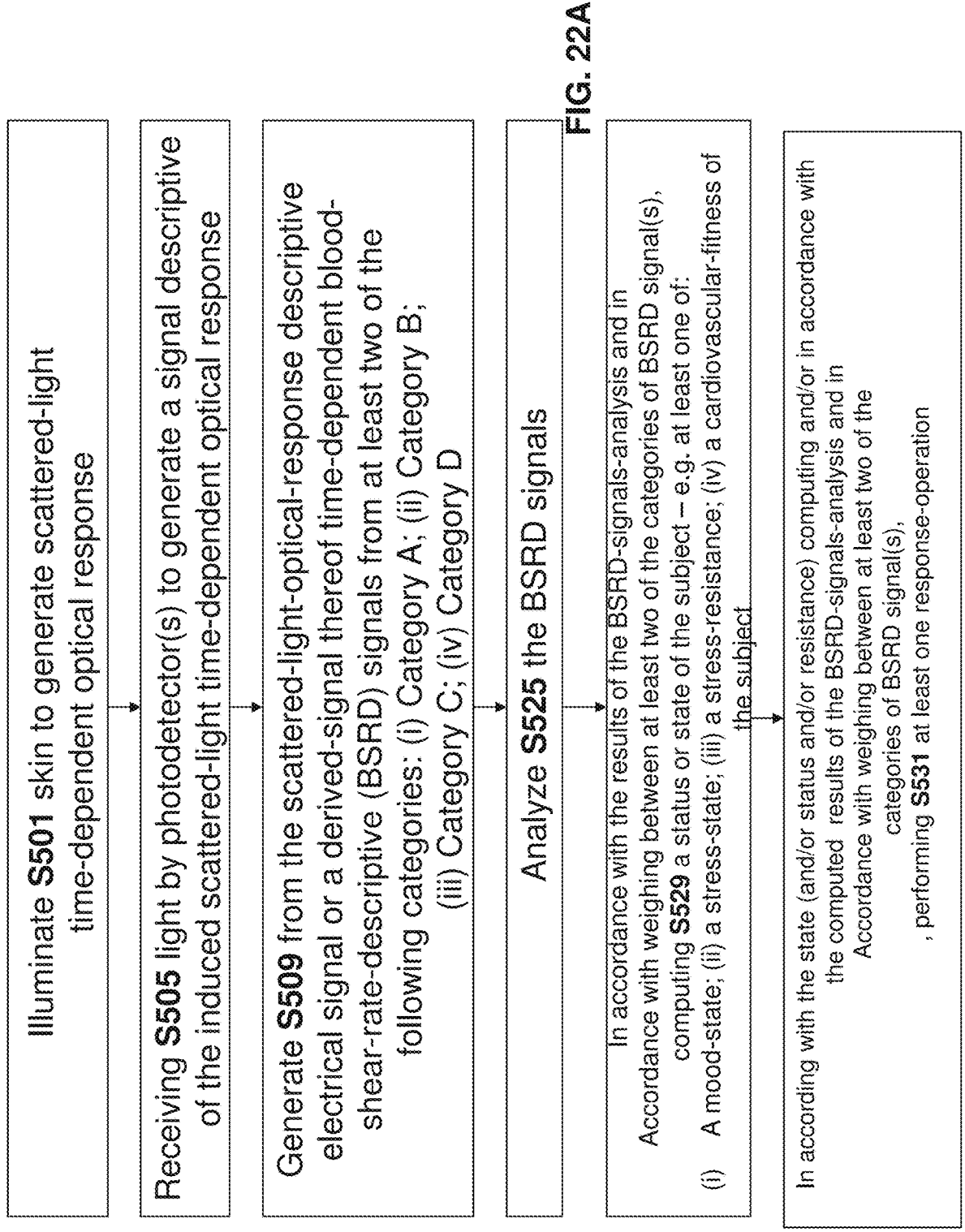

Referring to FIG. 22A, it is noted that embodiments of the present invention relate to situations where (i) BSRDs from two or three or four of these categories are generated (step S509) and each analyzed (step S525) and (ii) according to the results of this analysis (step S529) emotion and/or mood and/or stress and/or cardiovascular fitness is computed.

In some embodiments, a different respective classifier/predictor (i.e. for computing emotion and/or stress and/or cardiovascular fitness) may be introduced.

In theory, it may be possible to generate a single BSRD having a frequency profile that includes the profiles of two or more of the BSRDs. However, when this information is mixed together it may in fact be 'noise'—in contrast, it is possible to (i) 'separate' this information by generating separate BSRDs and then (ii) recombine this information. A separate predictor/classifier (i.e. for determining emotion and/or mood and/or stress and/or cardiovascular fitness and/or a 'type' of stress (e.g. mental versus emotional) may be provided for each BSRD category. Each BSRD-category-specific predictor/classifier may be employed to combine a classification/prediction of emotion and/or mood and/or stress and/or cardiovascular fitness and/or a 'type' of stress and the results may be combined to provide an accuracy-boosted combined classifier/predictor.

Any method of combining multiple predictors/classifiers may be employed including but limited to Markov models, multiple regression, bagging algorithms, and voting techniques.

Figure 22B:
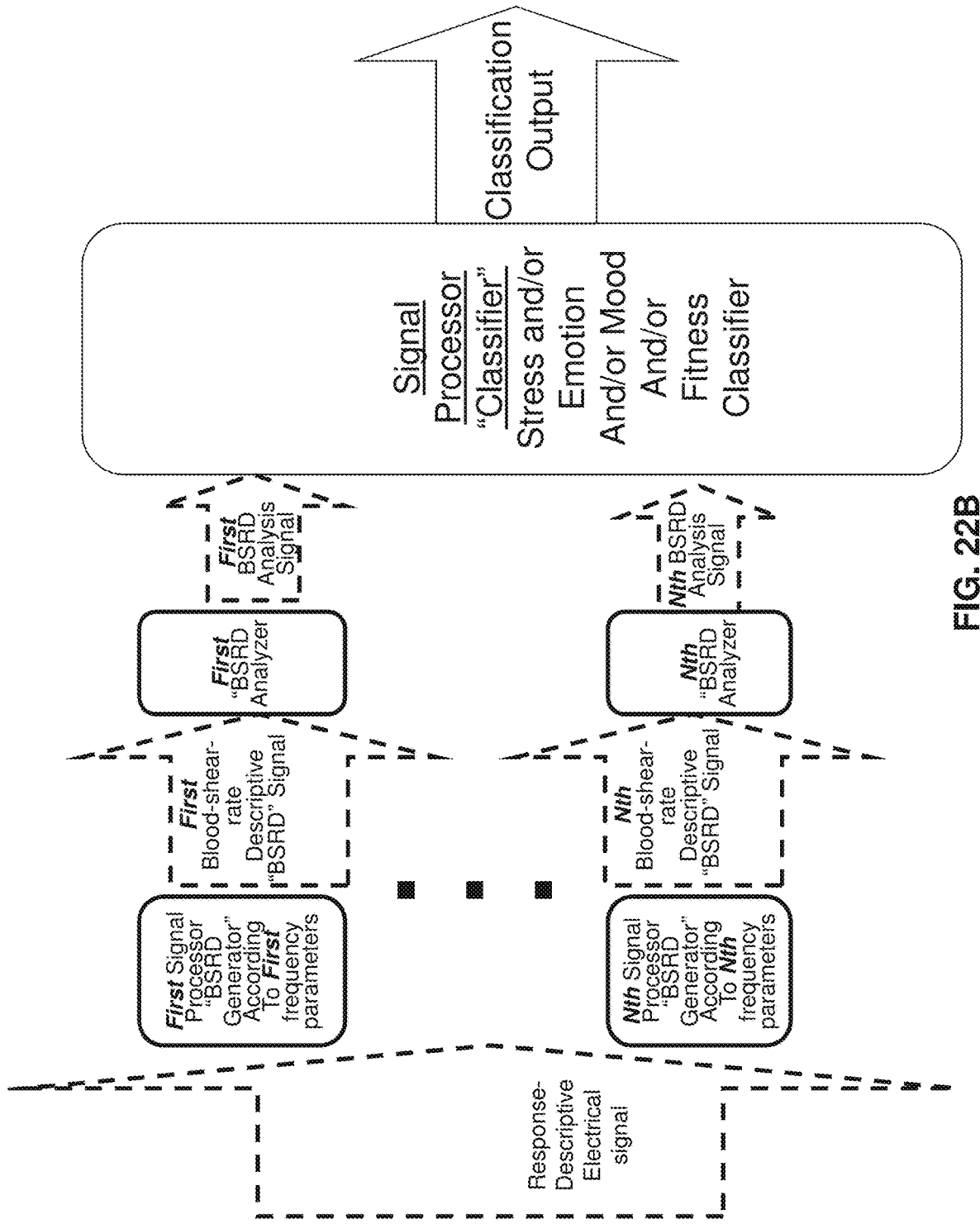

FIG. 22B shows data flow related to the method of FIG. 22A.

The weighing between the different categories of BSRD may be static or, in some embodiments, may be dynamic. In one example related to FIG. 23, a classifier may be based upon pulsatile BSRD. In this example, it may be possible to (i) generate a pulsatile BSRD in step S651 (*ii*) analyze the pulsatile BSRD (e.g. category D BSRD) in step S665-S769 to determine a prominence of pulsatile features therein—i.e. the determine if there was a 'good measurement' of pulse. For example, in the presence of motion artifacts or other physical perturbations may preclude a good measurement of pulse and reduce the pulsatile quality/prominence of pulsatile features in the pulsatile BSRD In the event that there was a 'good pulse measurement' (step S665) the weight of the pulsatile BSRD signal (e.g.

category D BSRD) may be dynamically increased at the expense of the weight of the non-pulsatile BSRD (e.g. category A or B BSRD). Conversely, in the event that there was a 'poor pulse measurement' (step S669) the weight of the pulsatile BSRD signal (e.g. category D BSRD) may be dynamically decreased, while commensurately increasing a weight of the non-pulsatile BSRD (e.g. category A or B BSRD).

Figure 23:
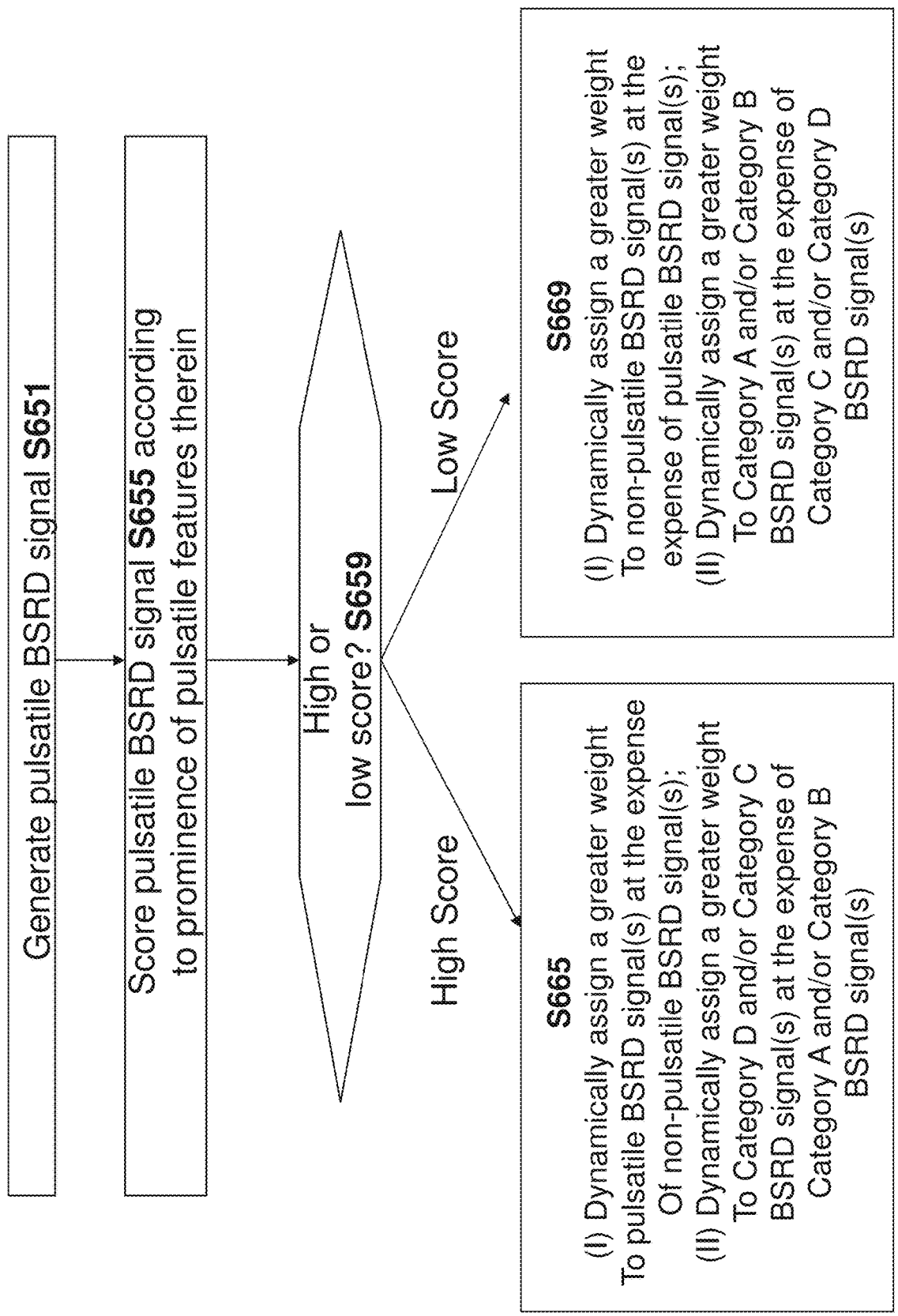
Figure 24:
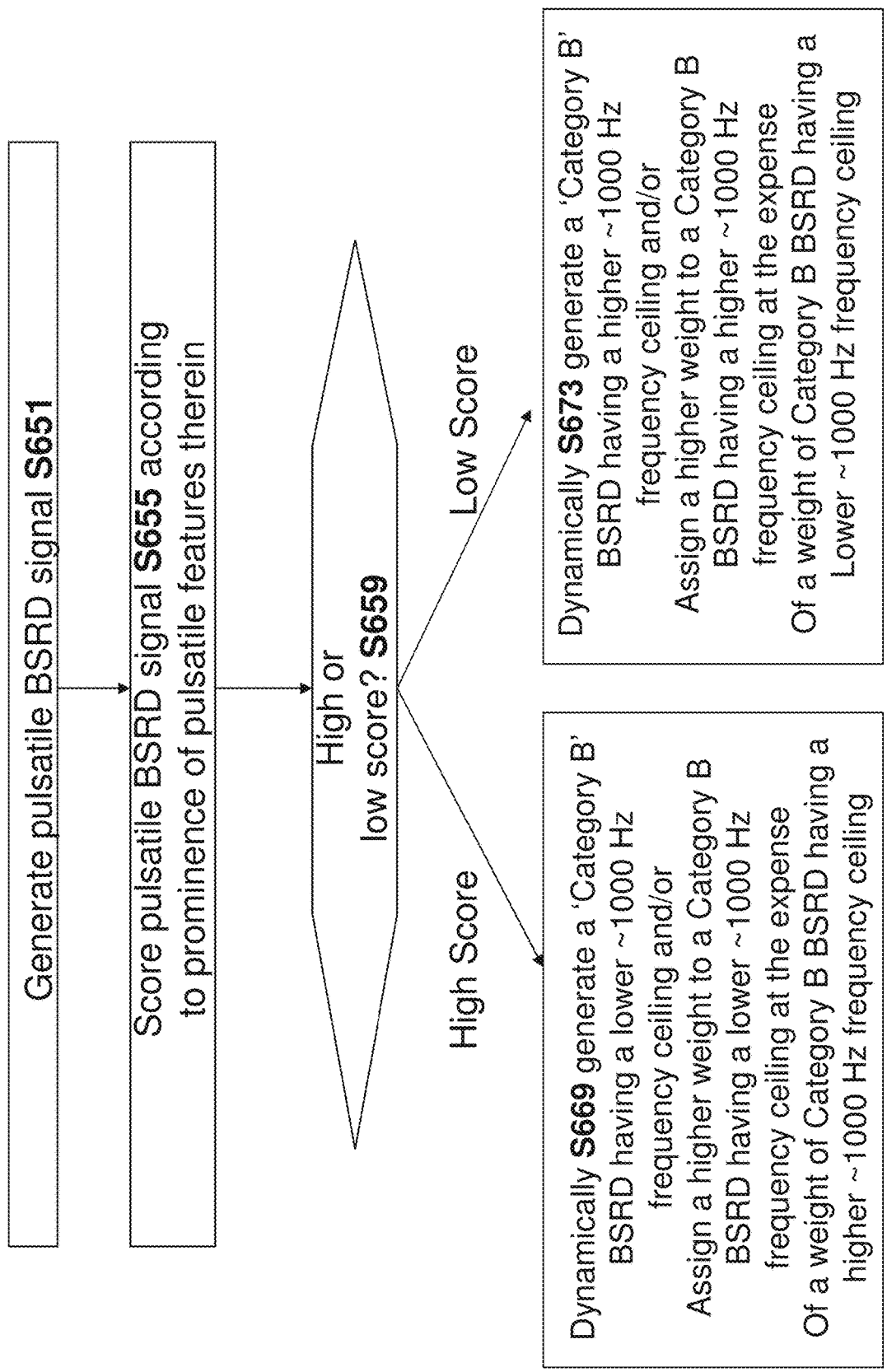

FIG. 23 relates to the example of weighing between different BSRD in order to increase an accuracy of measurement of emotion and/or stress (or type of stress) and/or cardiovascular parameter. FIG. 24 relate to dynamic generation of BSRDs for the same purpose. In particular, FIG. 24 relates to the situation wherein multiple BSRDs are generated, the 'quality' of a first BSRDs is scored (e.g. pulsatile BSRD scored in steps S655-S659) and a second BSRD is generated according to a frequency selection profile determined in response to the results of scoring of the first BSRD.

Thus, in the example of FIG. 24: a pulsatile BSRD is generated and scored (step S651-S659)—for example, a strong pulsatile BSRD and/or category D BSRD. In the event that the prominent pulsatile features are detected within the pulsatile BSRD, this may be indicative of a prominence of pulsatile information even at frequencies near the 'lower frequency range' where pulsatile information may be found. In this case, there may be a concern of 'polluting' the category B BSRD with pulsatile information. Thus, in response to detecting these 'strong' pulsatile features in a first BSRD (i.e. pulsatile), the frequency ceiling for a second BSRD (i.e. category B BSRD) may be reduced in step S669, even if the 'price paid' for this is a lower energy category B BSRD. Conversely, in situations where the pulsatile BSRD has less prominent pulsatile features, this is less of a concern. In response to detecting this situation (step S673), it may be decided to dynamically increase the ~100 Hz frequency 'ceiling' for the Category B BSRD.

Figure 25:
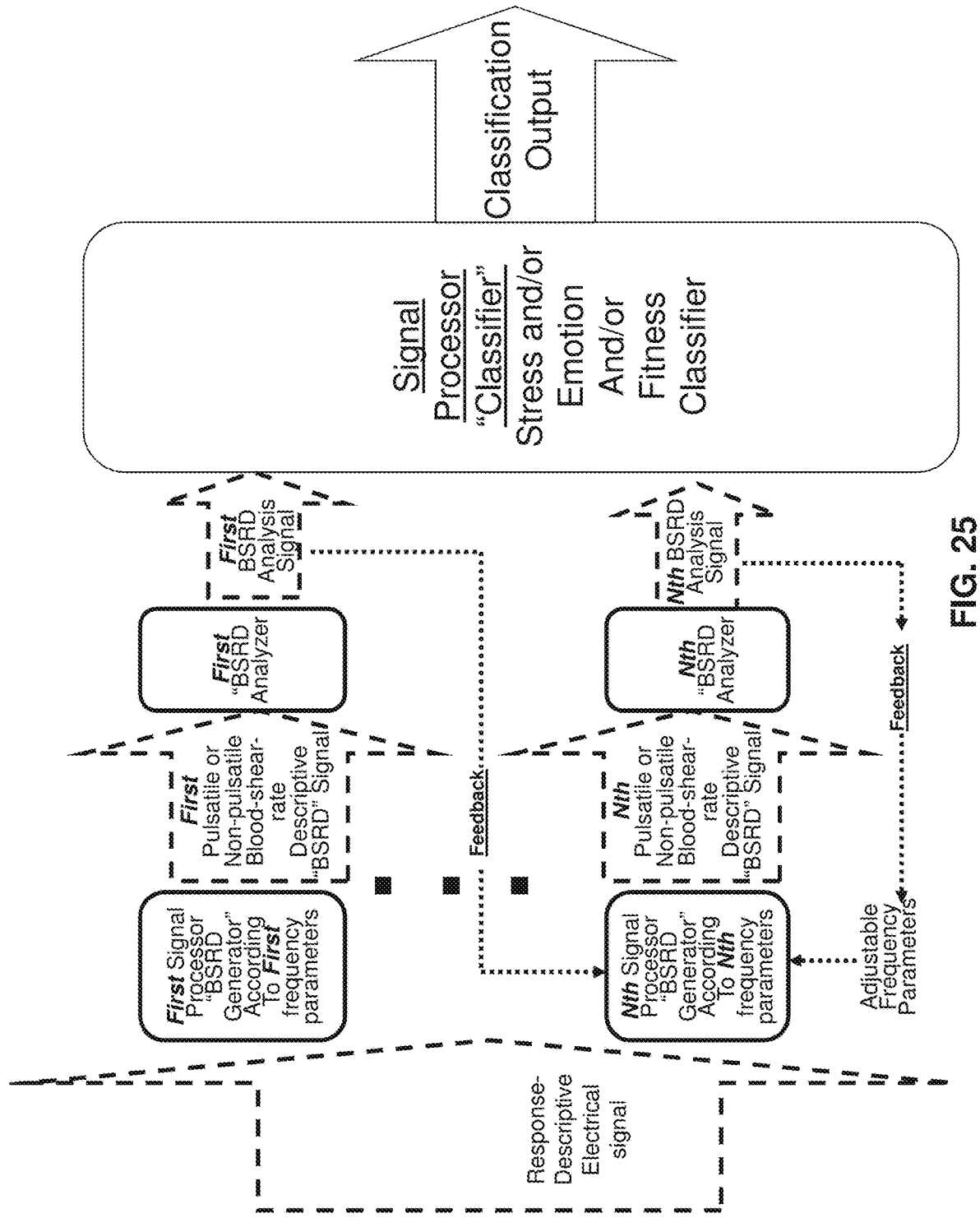

As shown in flow diagram of FIG. 25, the generation of a particular type of BSRD may be in accordance with (i) downstream feedback from generating the BSRD (see for example, FIG. 12 where the BSRD is analyzed for a prominence of non-pulsatile features) and (ii) feedback from generating even a different type of BSRD (see, for example, FIG. 24).

In addition, as shown in FIG. 23, the weighting between different categories of BSRDs may be dynamic.

A Discussion of FIG. 26A-26H—Analyzing Multiple Types of BSRDs (Fitness)

As shown in FIGS. 26A-26D, by combining data from multiple types of BSRDs, it is possible to more accurately predict/detect stress and/or emotion and/or fitness. FIGS. 26A-26D relate to fitness. For each of FIG. 26A-26D, generation and analysis of a BSRD is performed for two groups of subjects—one group of 'trained' or physically fit subjects (lighter data points) and another group of 'not fit' subjects (darker data points). Each subject had a unique number (on the x axis) and a particular parameter computed by analyzing a particular type of BSRD was computed.

Figure 26A:
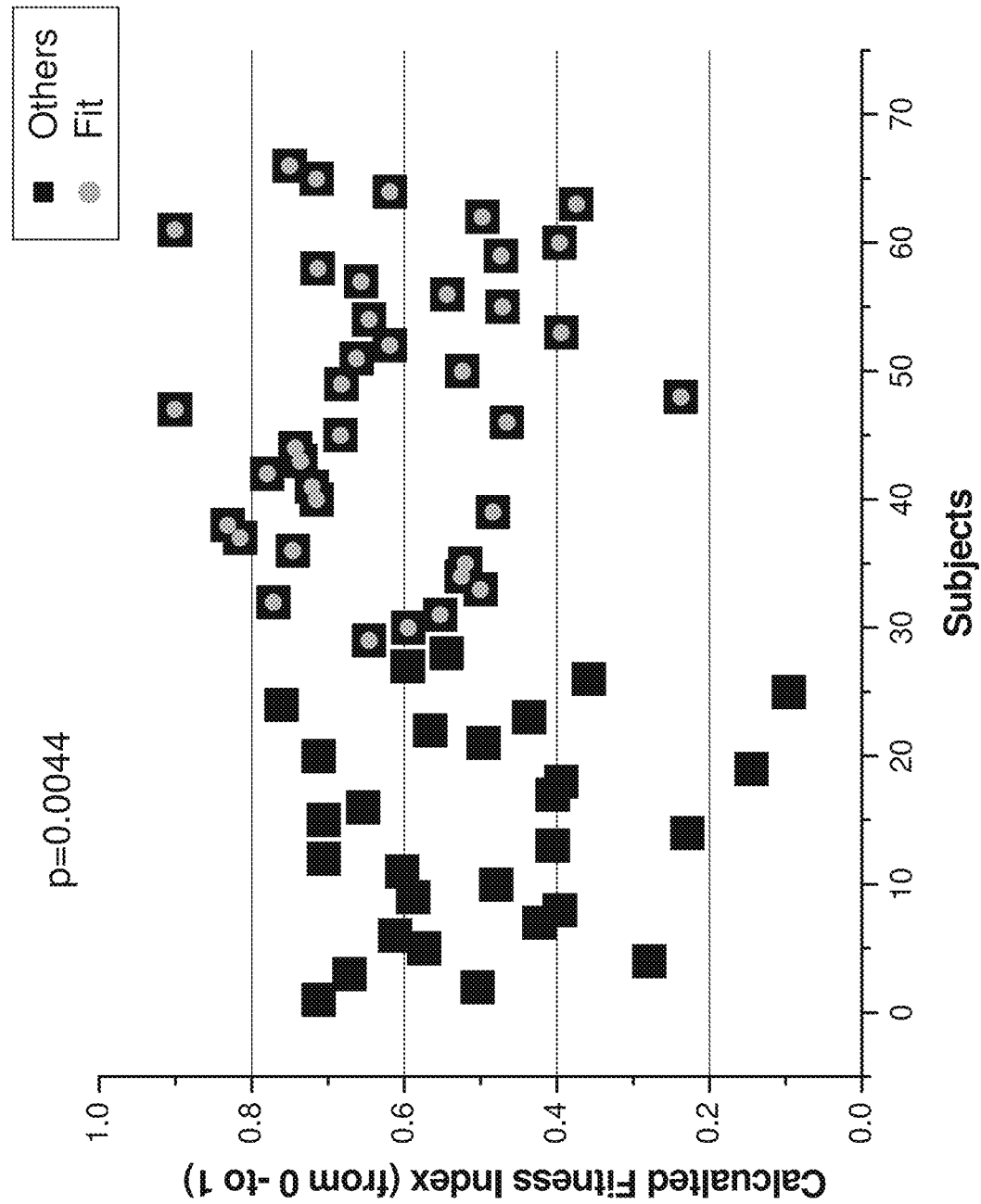

In FIG. 26A, a category A BSRFD was generated [0 Hz, 300 Hz] and this category A BSRD was subjected to an analysis such that a fraction of the energy in the band [0.15 Hz, 0.7 Hz] (respiration band) was computed (i.e. relative contribution). The 'prediction power' is $p=0.00^{44}$ where a lower number is a better predictor.

Figure 26B:
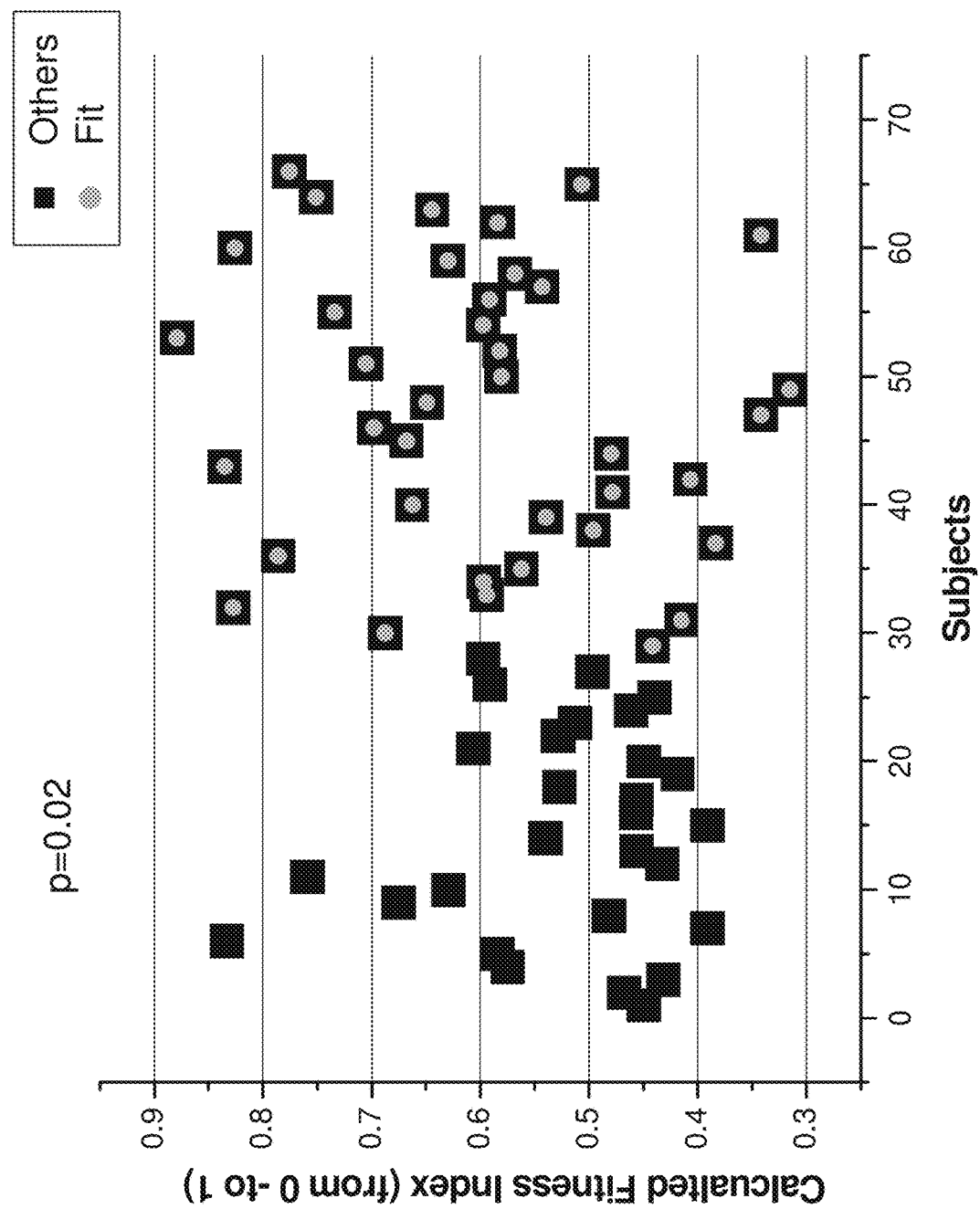

In FIG. 26B a category B BSRD was generated [300 Hz, 1 KHz] was generated and this category B BSRD was subjected to an analysis such that a fraction of the energy in the band [0.15 Hz, 0.7 Hz] (respiration band) was computed (i.e. relative contribution). The prediction power is 0.02—thus, the parameter of FIG. 26A is a better predictor.

Figure 26C:
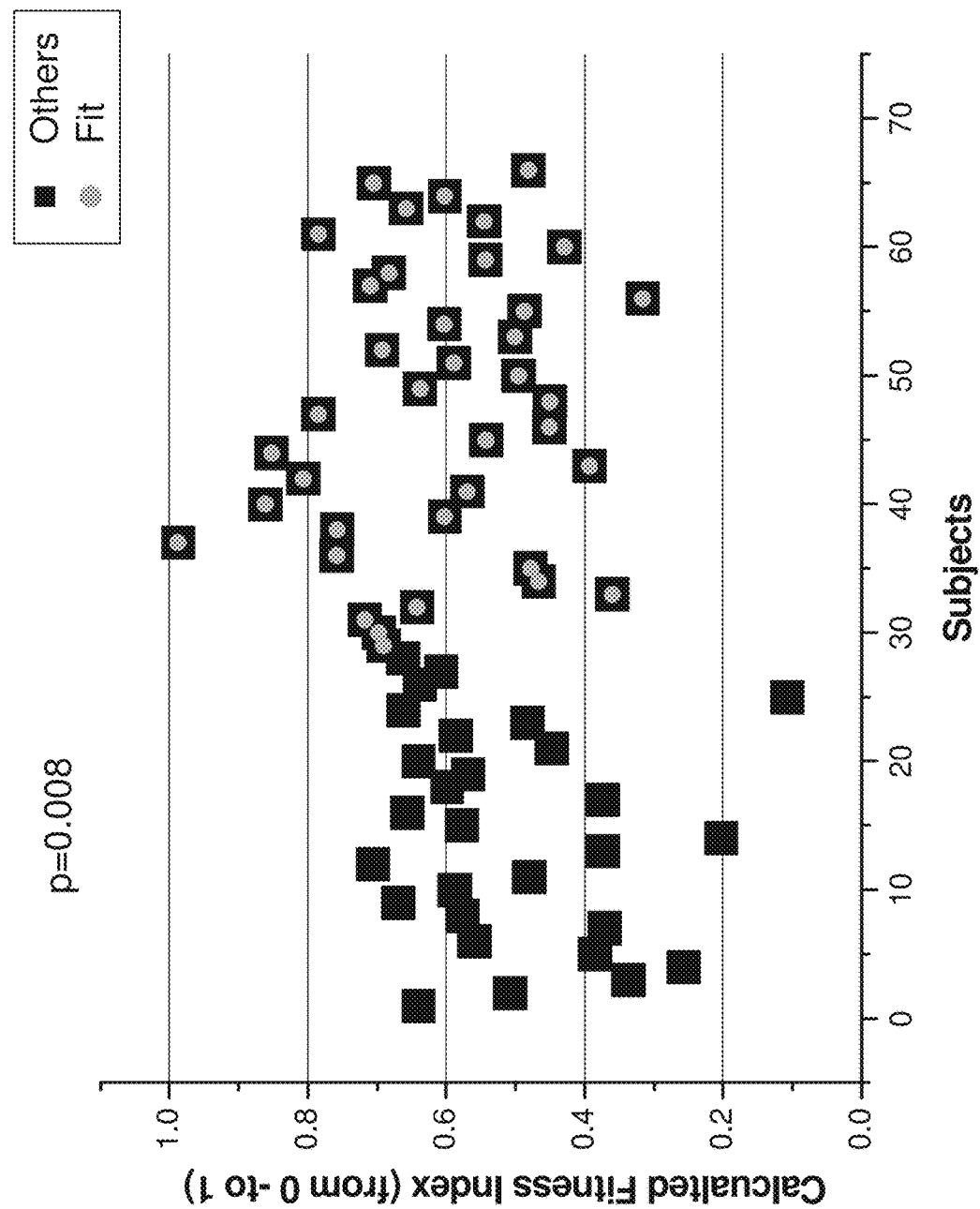

In FIG. 26C a [4 Khz, 10 Khz] pulsatile BSRD was generated, pulsatile components were removed (to obtain therefrom a non-pulsatile BSRD), and this non-puslatile BSRD was analyzed such that a fraction of the energy in the band [0.05 Hz, 0.15 Hz] was computed (i.e. relative contribution)—the prediction power is 0.008—thus, the parameter of FIG. 26A is a better predictor while the parameter of FIG. 26B is a worse predictor.

Figure 26D:
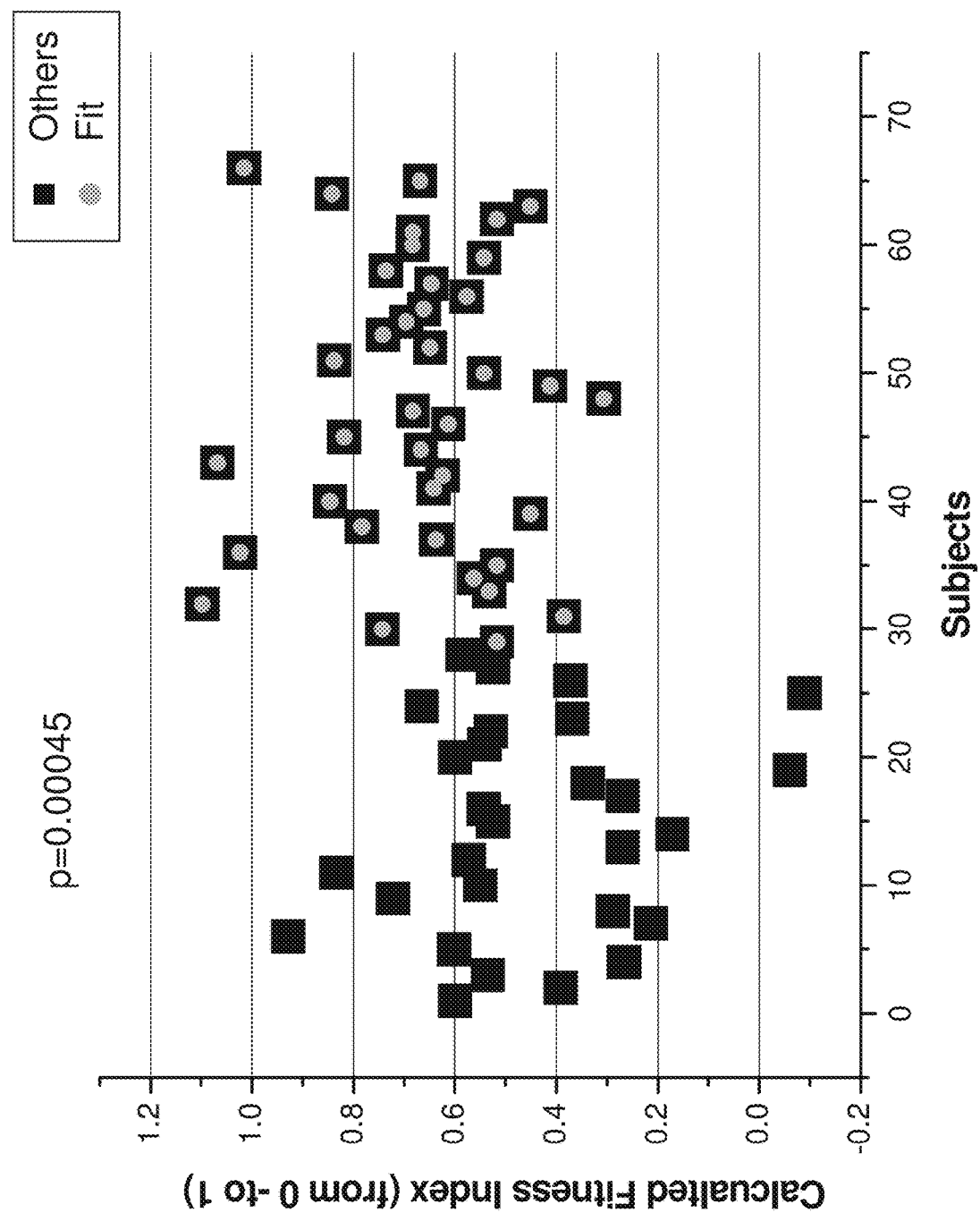

In FIG. 26D predictive/measurement power of a combined index is presented—→-0.7+1.1*(parameter of FIG. 26A)+1.15*(parameter of FIG. 26B). This combined index has a greater predictive power than the indices of any of FIGS. 26A-26C. In particular, a value of p is 0.00045.

Figure 26E:
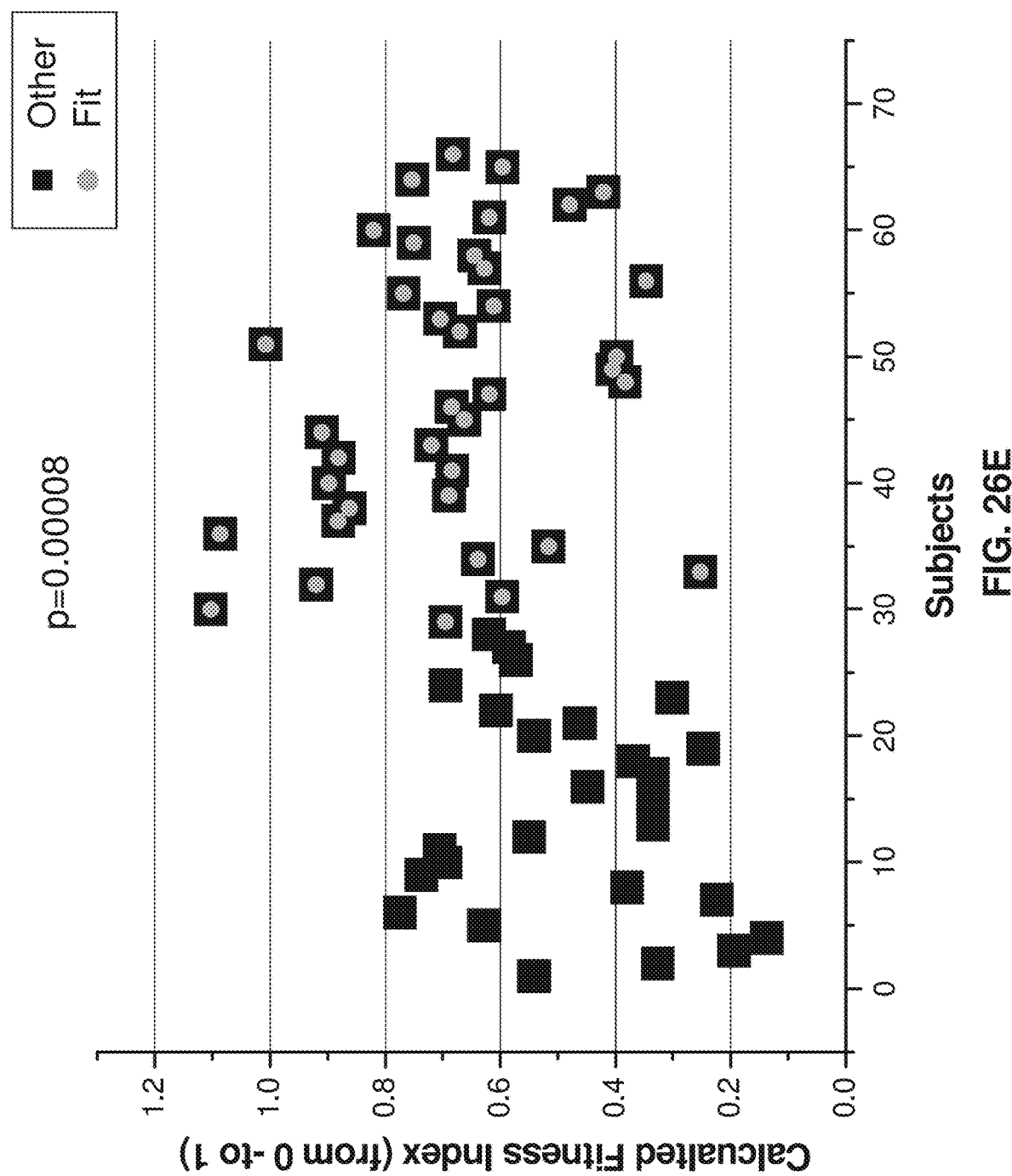

In FIG. 26E predictive/measurement power of a combined index is presented—→-0.95+1.23*(parameter of FIG. 26A)+1.45*(parameter of FIG. 26C). This combined index has a greater predictive power than the indices of any of FIGS. 26A-26D—in particular, a value of p is 0.00008.

Figure 26F:
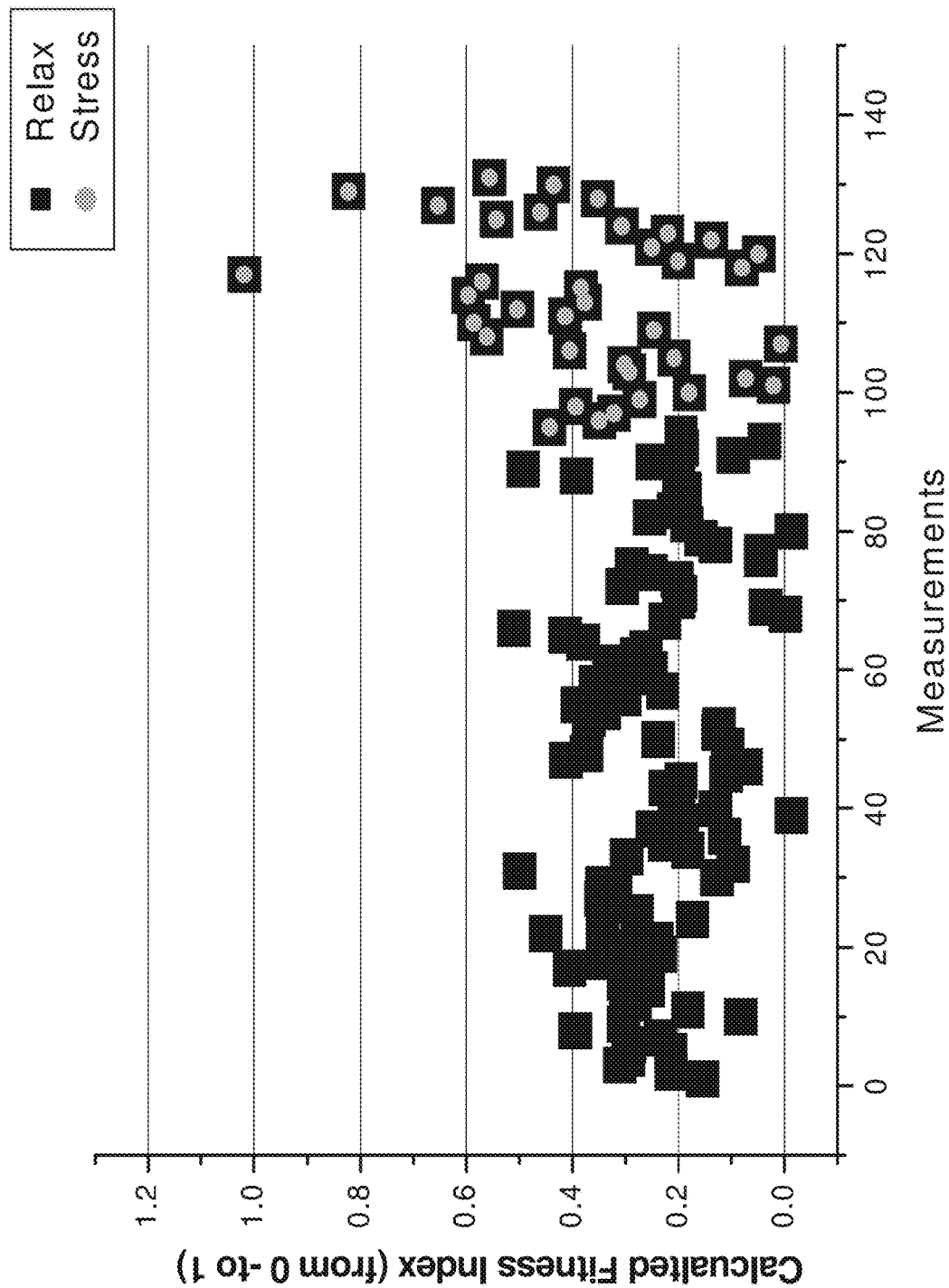
Figure 26G:
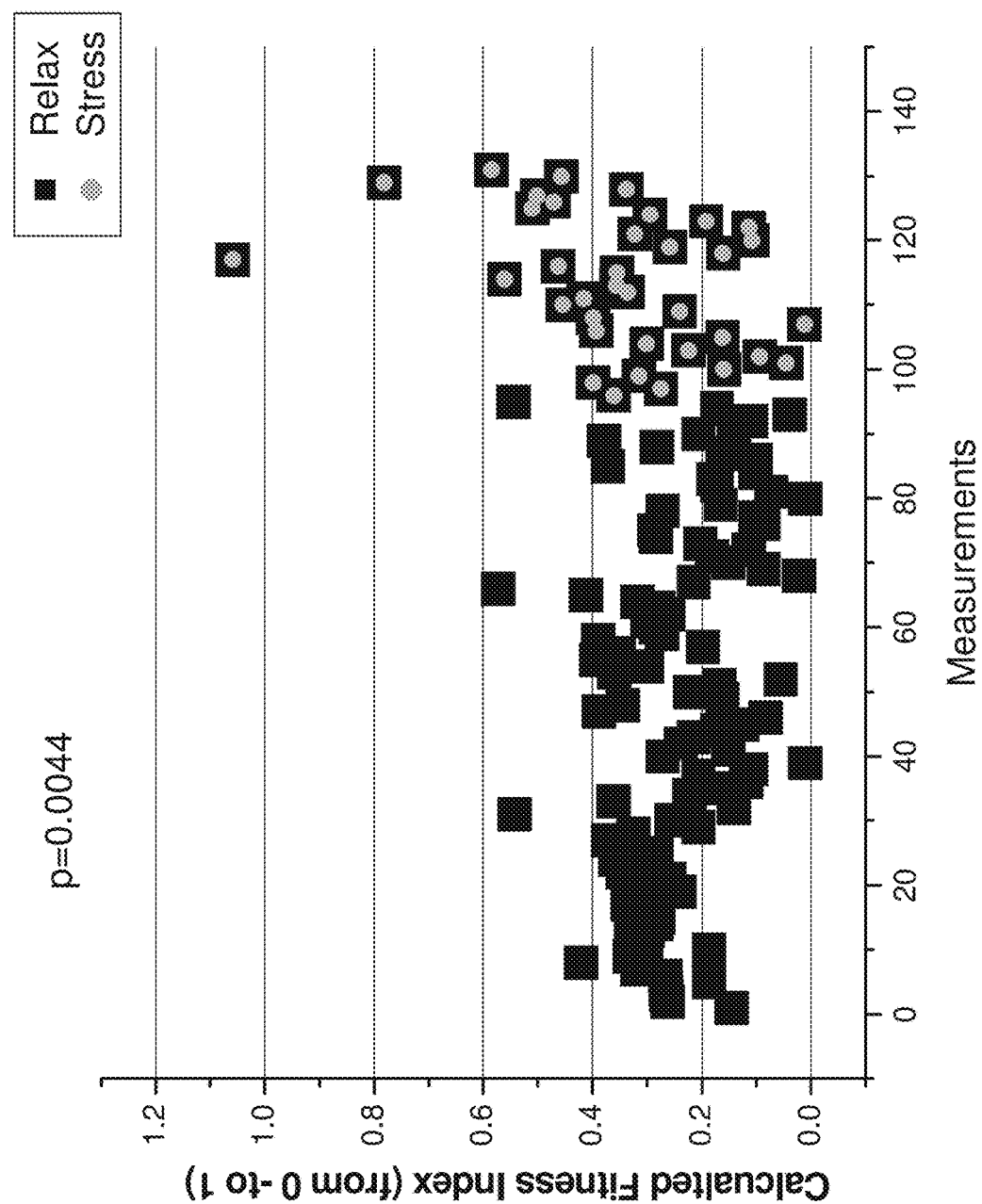

FIGS. 26A-26E related to measuring cardiovascular fitness. FIGS. 26F-26G relate to measuring stress.

In FIG. 26F, a [0 KHz, 300 KHz] BSRD was generated—this category A non-BSRD was subjected to a stochastic analysis to compute a Hurst component (see FIGS. 18A-18B).

In FIG. 26G, a [2 KHz, 8 KHz] BSRD was generated and pulsatile components were removed to generate a non-pulsatile BSRD—thi non-pulsatile BSRD s was subjected to an analysis such that a fraction of the energy in the band [0.05 Hz, 0.15 Hz] (respiration band) was computed (i.e. relative contribution).

Figure 26H:
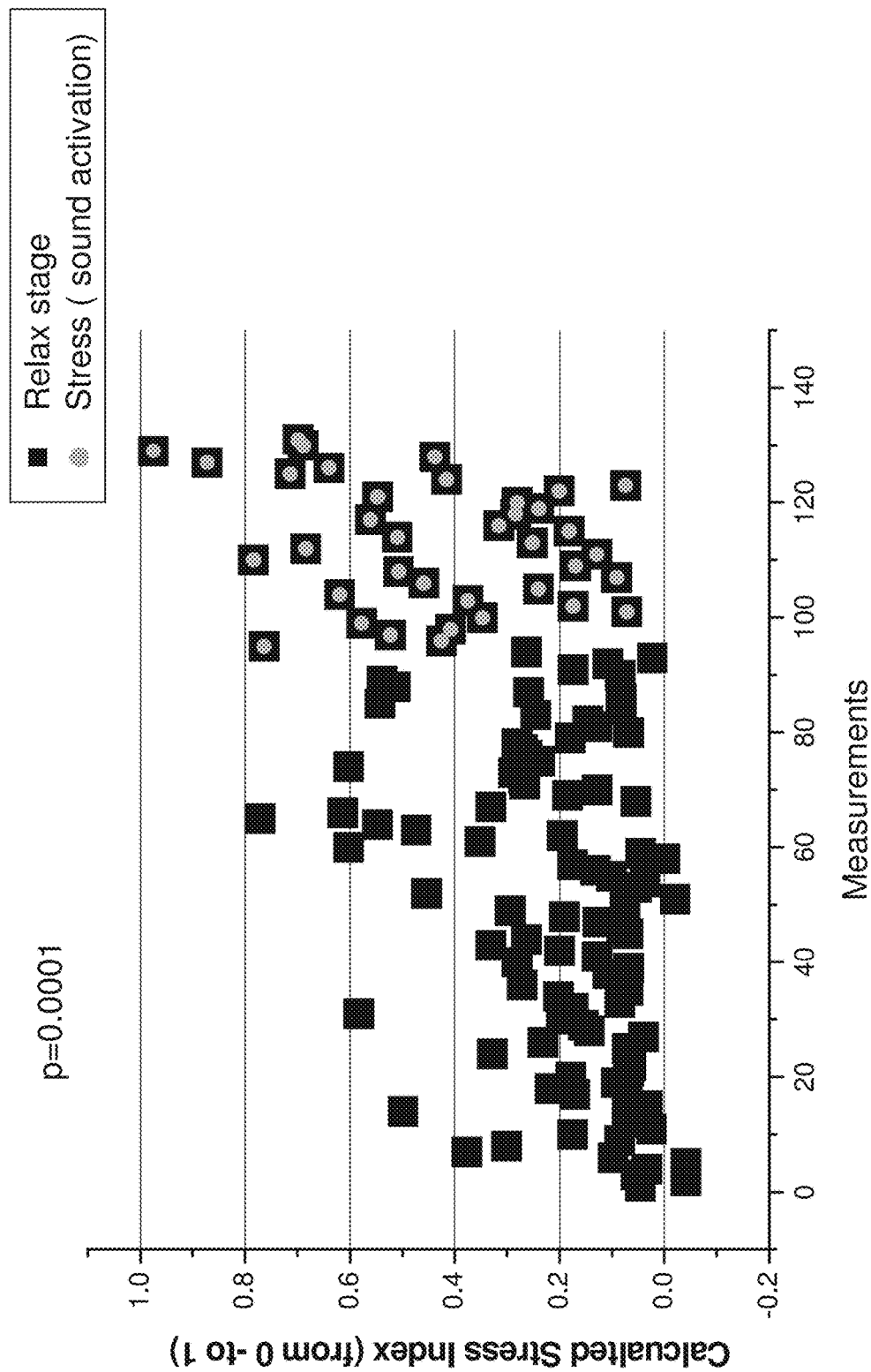

FIG. 26H relates to combining the analyses of the different BSRDs—i.e. combining FIGS. 26F-26G to increase measurement/prediction power of stress.

Thus, as discussed above (see FIG. 22A) it is possible to improve measurement accuracy by generating multiple 'types' of BSRDs, analyzing each BSRD, and combining the results—this may be performed for fitness (FIGS. 26A-26E), stress (FIGS. 26F-26H), mood, apnea or any other 'physiological measurement target' disclosed herein.

A Discussion of FIG. 26I-26L—Analyzing Multiple Types of BSRDs (Stress)

As shown in FIGS. 26A-26D, by combining data from multiple types of BSRDs, it is possible to more accurately predict/detect stress and/or emotion and/or fitness. FIGS. 26A-26D relate to stress.

Figure 26I:
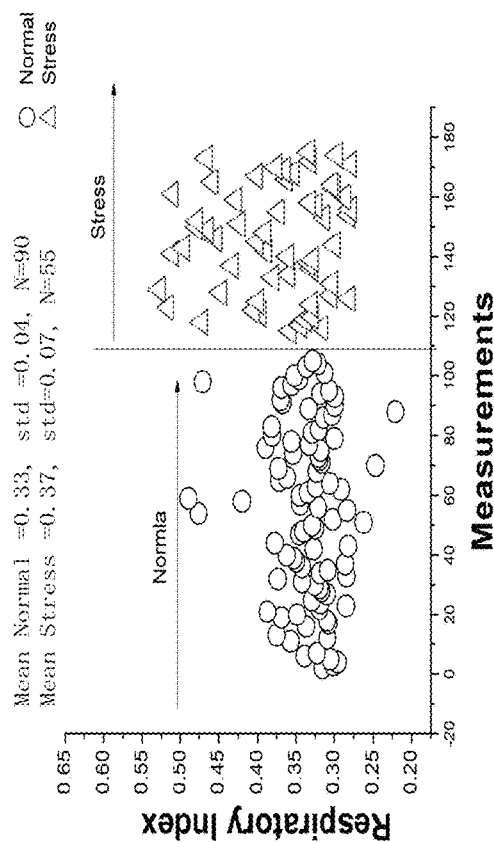
Figure 26J:
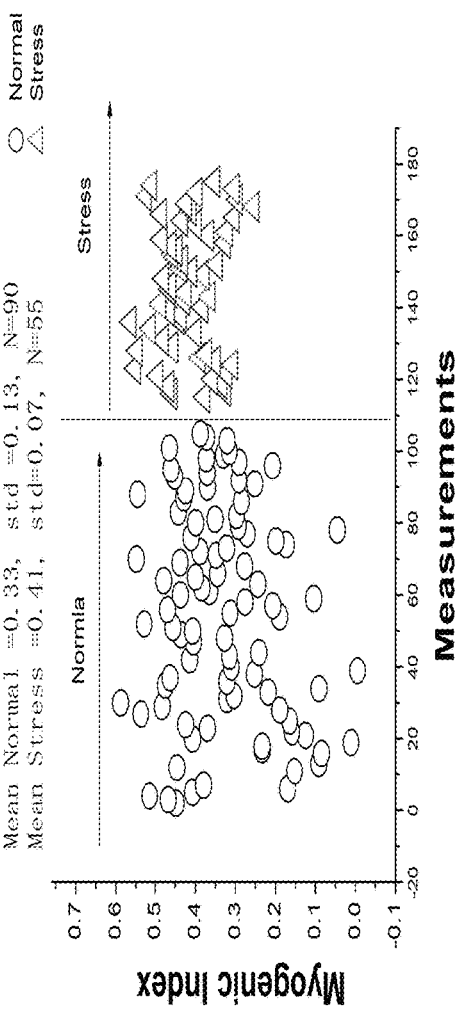
Figure 26K:
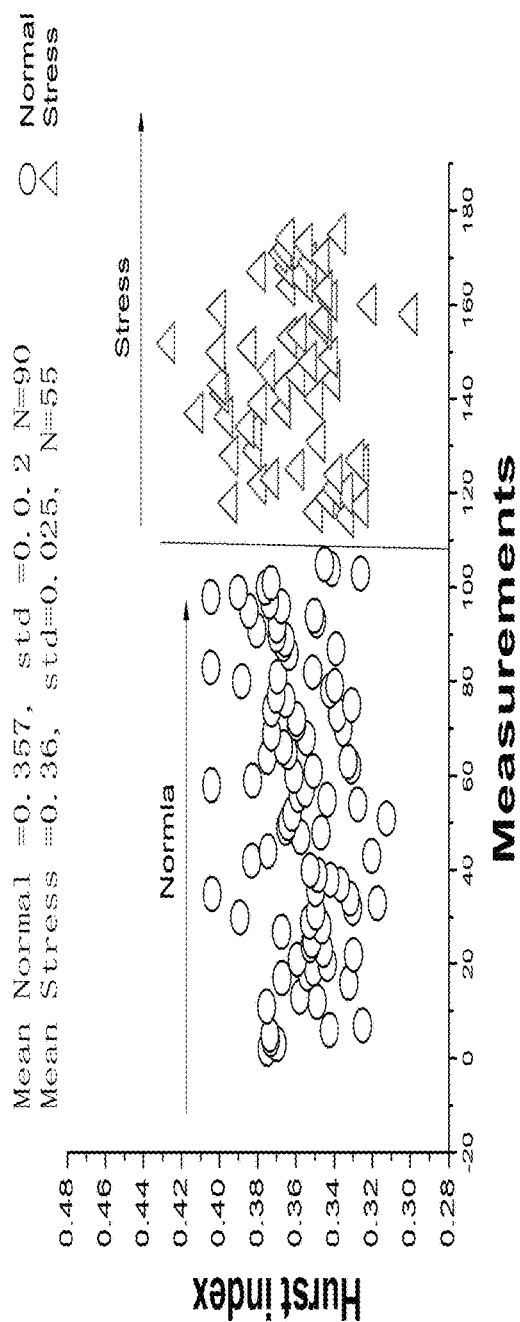

FIG. 26I relates to a respiratory index for bandpass 500 Hz-1 KHz. FIG. 26J relates to a myogenic index for a bandpass 1-3 KHz. FIG. 26K relates to a Hurst index for bandpass 0-500 Hkz.

Figure 26L:
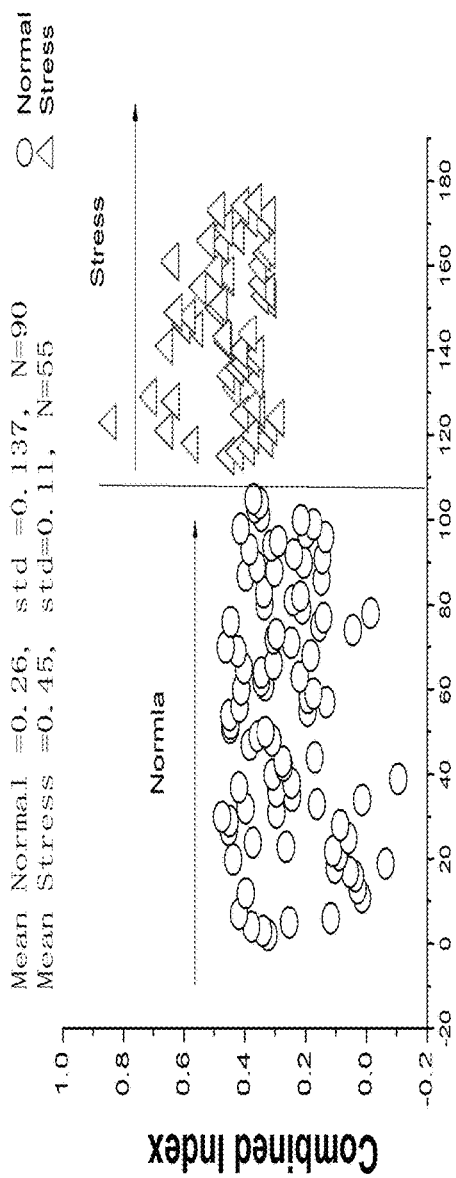

FIG. 26L relates to a combined index—Combined Weighed Index=0.44-3.44*(HURST INDEX)+1.3*(Myogenic Index)+1.87*(Respiratory Index)

The predictive power (i.e. to distinguish between a 'stressed group' and a 'normal group') of the combined index (FIG. 26L) is stronger than the other indices.

A Discussion of FIG. 27

As discussed above, a Mayer wave is only one type of physiological response signal. As discussed above (see FIGS. 10 and 12) the 'target signal' may be expressed in either the time domain or the frequency domain (i.e. as a power spectrum). Similarly, any 'scoring' of a BSRD may entail scoring a power spectrum of the BSRD with reference to a power spectrum of a target physiological response signal.

FIGS. 27A-27D relate to four 'baseline' BSRDs—all generated when a single subject is in a 'relaxed state' FIGS. 28A-28D relate to four 'baseline' BSRDs—all generated when the same single subject is 'listening to emotional music' which changes his mood-state. FIGS. 29A-29D relate to four 'baseline' BSRDs—all generated when the same single subject is performing mental exercise—i.e. a mental stress-load. FIGS. 30A-30D relate to four 'baseline' BSRDs—all generated after the single subject hears an unpleasant sound.

Figure 28B:
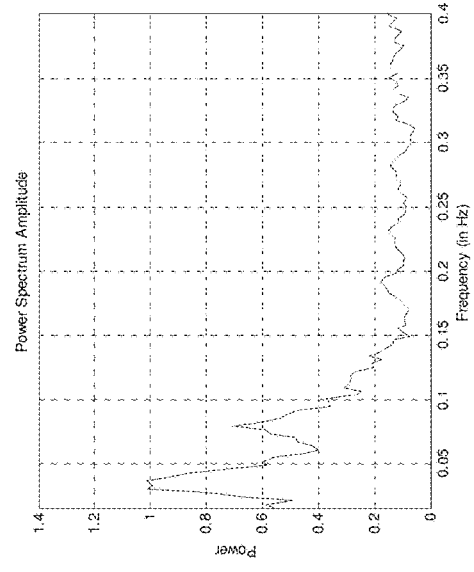
Figure 28D:
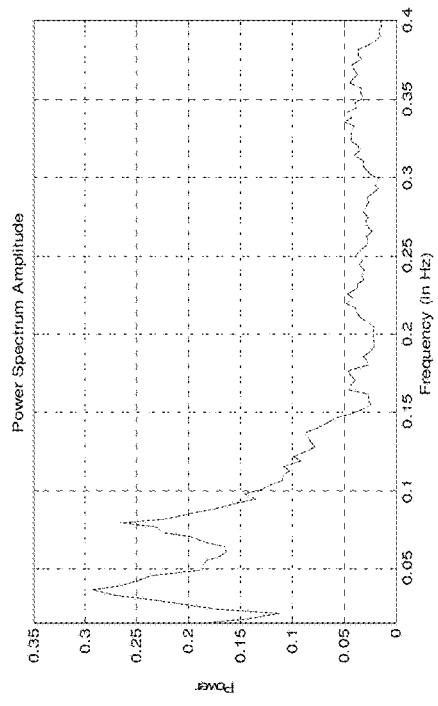
Figure 28A:
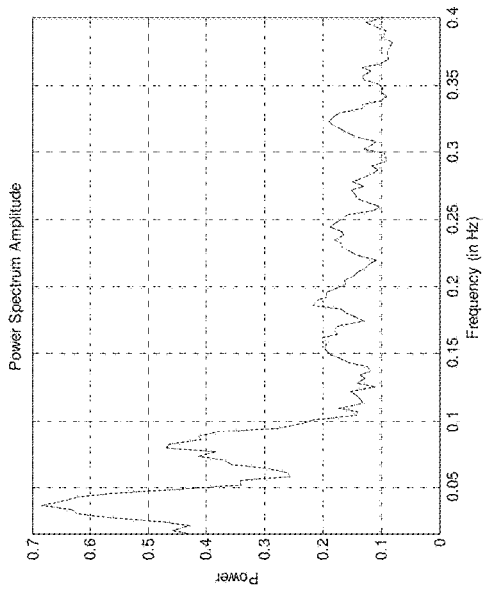

FIGS. 27A, 28A, 29A and 30A all illustrate a power spectrum of a [0 Khz, 0.4 KHz] BSRD (i.e. after filtering out pulsatile components using a bandpass filter thus for a [0 Khz, 0.4 Khz] BSRD this is not necessary) Thus, it is possible to compare the power spectrum of FIG. 28A to that of FIG. 27A to detect the influence of 'emotional music' on the [0 Khz, 0.4 KHz] BSRD. It is possible to compare the power spectrum of FIG. 29A to that of FIG. 27A to detect the influence of 'mental load/stress' on the [0 Khz, 0.4 KHz] BSRD. It is possible to compare the power spectrum of FIG. 30A to that of FIG. 27A to detect the influence of 'unpleasant sound' on the [0 Khz, 0.4 KHz] BSRD.

FIGS. 27B, 28B, 29B and 30B all illustrate a power spectrum of a [0.4 Khz, 1 KHz] BSRD (i.e. after filtering out pulsatile components using a bandpass filter thus for a [0.4 Khz, 1 KHz] BSRD this is not necessary) Thus, it is possible to compare the power spectrum of FIG. 28B to that of FIG. 27B to detect the influence of 'emotional music' on the [0.4 Khz, 1 KHz] BSRD. It is possible to compare the power spectrum of FIG. 29B to that of FIG. 27B to detect the influence of 'mental load/stress' on the [0.4 Khz, 1 KHz] BSRD. It is possible to compare the power spectrum of FIG. 30B to that of FIG. 27B to detect the influence of 'unpleasant sound' on the [0.4 Khz, 1 KHz] BSRD.

Figure 28C:
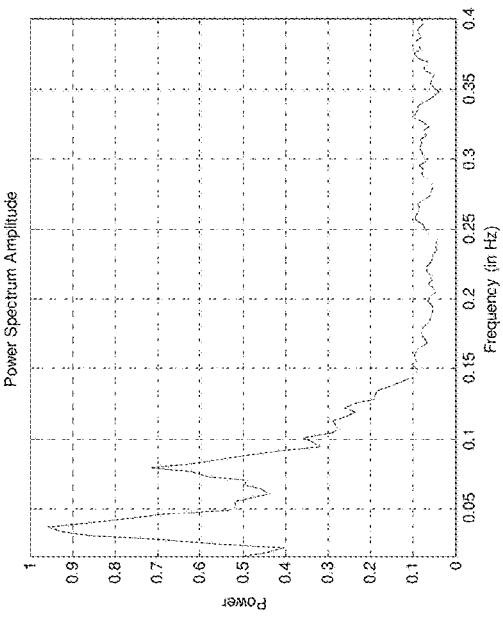
Figure 29A:
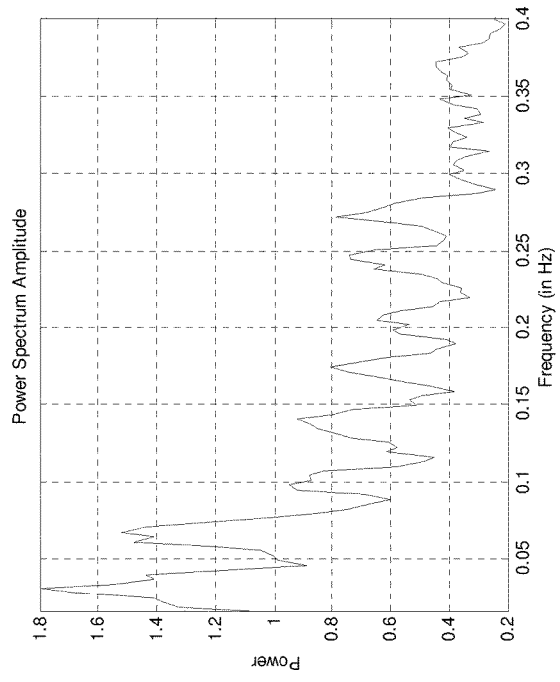
Figure 29B:
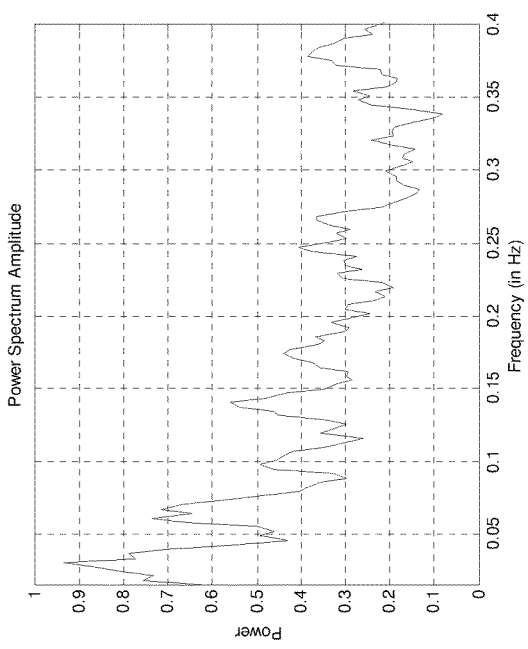
Figure 29C:
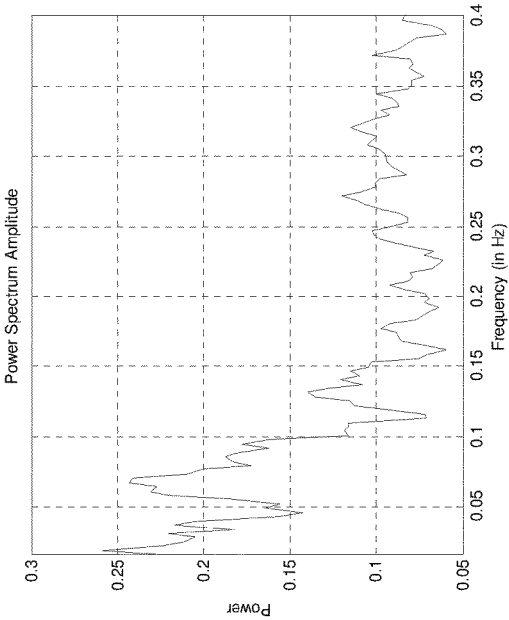
Figure 29D:
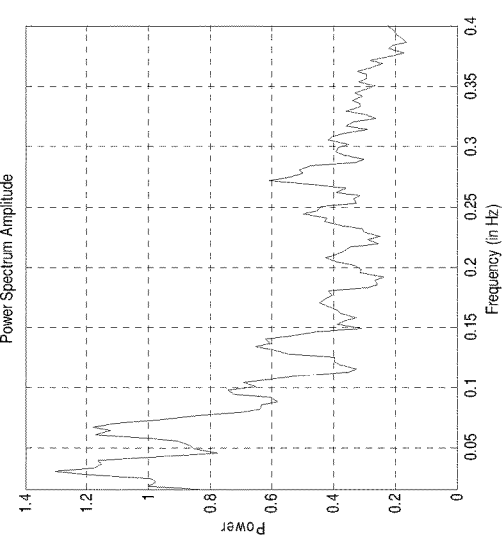
Figure 30A:
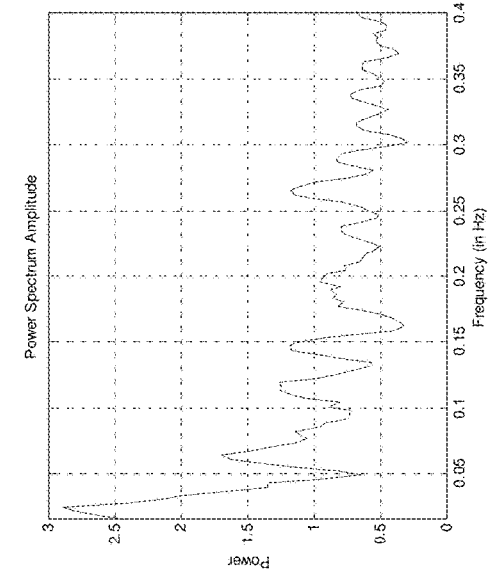
Figure 30B:
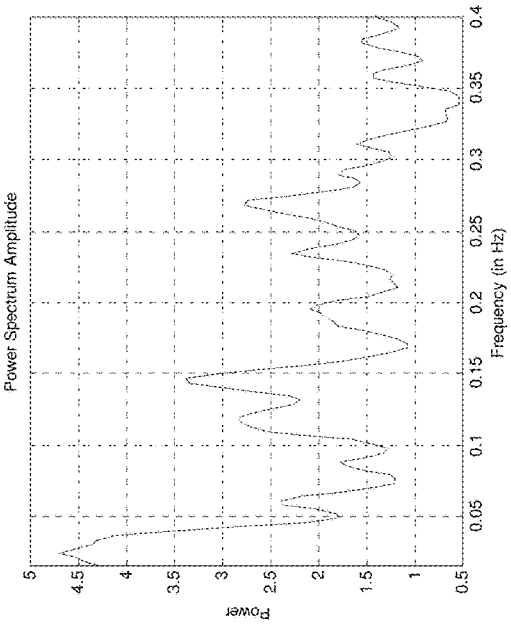
Figure 30C:
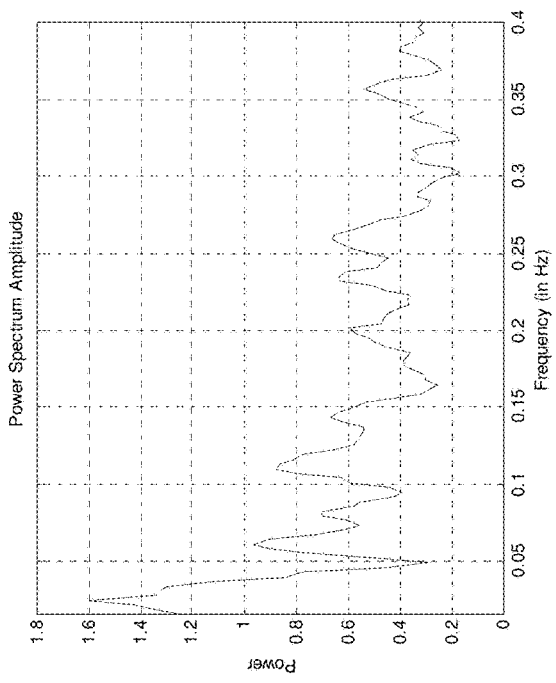
Figure 30D:
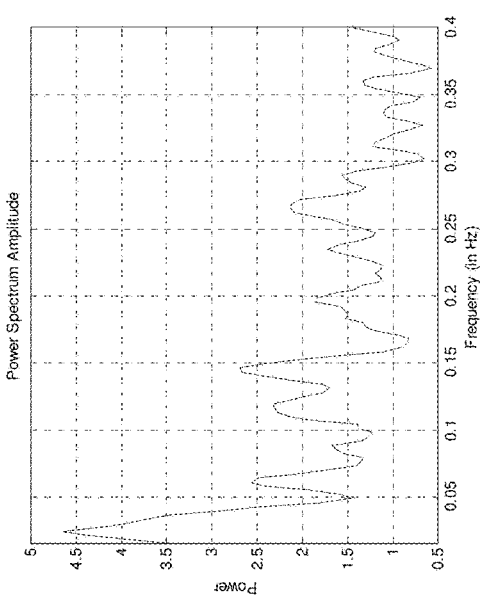

FIGS. 27C, 28C, 29C and 30C all illustrate a power spectrum of a [1 KHZ, 4 KHZ] BSRD (i.e. after filtering out pulsatile components using a bandpass filter thus for a [1 KHZ, 4 KHZ] BSRD this is not necessary) Thus, it is possible to compare the power spectrum of FIG. 28C to that of FIG. 27C to detect the influence of 'emotional music' on the [1 KHZ, 4 KHZ] BSRD. It is possible to compare the power spectrum of FIG. 29C to that of FIG. 27C to detect the influence of 'mental load/stress' on the [1 KHZ, 4 KHZ] BSRD. It is possible to compare the power spectrum of FIG. 30C to that of FIG. 27C to detect the influence of 'unpleasant sound' on the [1 KHZ, 4 KHZ] BSRD.

FIGS. 27D, 28D, 29D and 30D all illustrate a power spectrum of a [4 KHZ, 10 KHZ] BSRD (i.e. after filtering out pulsatile components using a bandpass filter thus for a [4 KHZ, 10 KHZ] BSRD this is not necessary) Thus, it is possible to compare the power spectrum of FIG. 28D to that of FIG. 27D to detect the influence of 'emotional music' on the [4 KHZ, 10 KHZ] BSRD. It is possible to compare the power spectrum of FIG. 29D to that of FIG. 27D to detect the influence of 'mental load/stress' on the [4 KHZ, 10 KHZ] BSRD. It is possible to compare the power spectrum of FIG. 30D to that of FIG. 27D to detect the influence of 'unpleasant sound' on the [4 KHZ, 10 KHZ] BSRD.

First Additional Discussion of Embodiments

A method for optically measuring, according to one or more a stress and/or mood and/or stress-resistance cardiovascular fitness parameter specific to a warm-blooded subject, the method comprising: a. illuminating a portion of the subject's skin or tissue by a VCSEL (vertical cavity surface emitting laser) or a diode laser to scatter partially or entirely coherent light off of the subject's moving red blood cells (RBCs) to induce a scattered-light time-dependent optical response; b. receiving the scattered light by a photodetector(s) to generate an electrical signal descriptive of the induced scattered-light time-dependent optical response; c. processing the scattered-light-optical-response-descriptive electrical signal or a derived-signal thereof to compute therefrom one or more blood-shear-rate-descriptive (BSRD) signal(s), each BSRD signal characterized by a respective frequency-selection profile; d. electronically analyzing features of the BSRD signal(s) of the BSRD signal group; e. in accordance with the results of the electronically analyzing of the at least two frequency-interval-specific shear-rate-descriptive signals, performing at least one of the following of subject-status-classification operation(s): (i) classifying a stress-state (e.g. type of stress or level of stress) of the subject; (ii) classifying a mood-state of the subject; (iii) classify a stress-resistance of the subject; (iv) classifying a cardiovascular fitness-status of the subject. wherein a frequency-selection profile of the BSRD(s) signal is computed dynamically so to adaptively maximize a prominence of a predetermined non-pulsatile physiological signal within the BSRD(s) and/or wherein the classification operation is performed dynamically so that a weight assigned to a BSRD signal is adaptively determined to increase a weight of BSRD signal(s) whose frequency-selection profile correspond to a greater prominence of the predetermined non-pulsatile physiological signal at the weight-expense of BSRD signal(s) whose frequency-selection profile correspond to a lesser prominence of the predetermined non-pulsatile physiological signal.

In some embodiments, the predetermined non-pulsatile physiological signal is a Mayer wave signal.

A method for optically measuring, according to one or more a stress and/or mood and/or stress-resistance cardiovascular fitness parameter specific to a warm-blooded subject, the method comprising: a. illuminating a portion of the subject's skin or tissue by a VCSEL (vertical cavity surface emitting laser) or a diode laser to scatter partially or entirely coherent light off of the subject's moving red blood cells (RBCs) to induce a scattered-light time-dependent optical response; b. receiving the scattered light by a photodetector(s) to generate an electrical signal descriptive of the induced scattered-light time-dependent optical response c. processing the scattered-light-optical-response-descriptive electrical signal or a derived-signal thereof to compute therefrom a non-pulsatile blood-shear-rate-descriptive (BSRD) signal(s), each BSRD signal characterized by a respective frequency-selection profile; d. subjecting the non-pulsatile BSRD signal(s) to a stochastic analysis or to a stationary-status analysis that quantifies a stationary/non-stationary status of the BSRD signal(s); e. in accordance with the results of the stochastic and/or stationary-status analysis, performing at least one of the following of subject-status-classification operation(s): (i) classifying a stress-state (e.g. type of stress or level of stress) of the subject; (ii) classifying a mood-state of the subject; (iii) classify a stress-resistance of the subject; (iv) classifying a cardiovascular fitness-status of the subject.

In some embodiments, non-pulsatile BSRD signal(s) are dynamically computed such that the frequency-selection profile thereof is dynamically adjusted so as to maximize a signal energy while minimizing a residual-pulse component of the BSRD signal(s).

In some embodiments, the method is performed adaptively such that: i. one or more non-pulsatile candidate BSRD signal(s) are scored so that (A) a greater signal energy and a lower pulsatile signal-contribution increase a quality-score of a rated non-pulsatile candidate BSRD signal and (B) conversely, a lower signal energy and a greater pulsatile signal-contribution decrease a quality-score of a rated non-pulsatile candidate BSRD signal; and ii. the subject-status-classification operation is performed dynamically so as to assign greater weight to candidate BSRD signal(s) having a higher score and to assign a lower weight to candidate BSRD signal(s) having a lower score.

In some embodiments, i. a pulsatile BSRD signal(s) is also generated from the scattered-light-optical-response-descriptive electrical signal or derived signal thereof; ii. subject-status-classification operation(s) is performed according to both feature(s) of the pulsatile BSRD signal(s) and the results of the stochastic and/or stationary-status analysis of the non-pulsatile BSRD signal(s); iii. the pulsatile BSRD signal(s) is rated according to a prominence of blood-pressure-waveform feature(s) therein; and iv. the non-pulsatile BSRD signal(s) is dynamically computed such that the frequency-selection profile thereof is dynamically adjusted.

A method for optically measuring, according to one or more a stress and/or mood and/or stress-resistance cardiovascular fitness parameter specific to a warm-blooded subject, the method comprising: a. illuminating a portion of the subject's skin or tissue by a VCSEL (vertical cavity surface emitting laser) or a diode laser to scatter partially or entirely coherent light off of the subject's moving red blood cells (RBCs) to induce a scattered-light time-dependent optical response; b. receiving the scattered light by a photodetector(s) to generate an electrical signal descriptive of the induced scattered-light time-dependent optical response or an AC component thereof; c. processing the scattered-light-optical-response-descriptive electrical signal or a derived-signal thereof to compute therefrom at least two blood-shear-rate-descriptive (BSRD) signal(s) selected from the BSRD signal group, each blood-rate-descriptive BSRD signal characterized by a different respective frequency-selection profile, the BSRD signal group consisting of the following signals: (i) a [sub −200 Hz, ~300 Hz] BSRD signal; (ii) a [~300 Hz, ~1000 Hz] signal; (iii) a [~1000 Hz, ~4000 Hz] signal and (iv) a [~4000 Hz, z Hz] (z>=7,000) signal; d. electronically analyzing features at least two the BSRD signals of the BSRD signal group; e. in accordance with the results of the electronically analyzing of the at least two frequency-interval-specific shear-rate-descriptive signals, performing at least one of the following of subject-status-classification operation(s): (i) classifying a stress-state (e.g. type of stress or level of stress) of the subject; (ii) classifying a mood-state of the subject; (iii) classify a stress-resistance of the subject; (iv) classifying a cardiovascular fitness-status of the subject.

A machine-learning-based method for optically measuring, according to one or more a stress and/or mood and/or stress-resistance cardiovascular fitness parameter specific to a warm-blooded subject, the method comprising: a. monitoring behavior patterns of the subject by camera and/or receiving data via a graphical-user-interface and/or monitoring interactions of the user with advertisement(s) and/or according to audio output of the user; b. illuminating a portion of the subject's skin or tissue by a VCSEL (vertical cavity surface emitting laser) or a diode laser to scatter partially or entirely coherent light off of the subject's moving red blood cells (RBCs) to induce a scattered-light time-dependent optical response; c. receiving the scattered light by a photodetector(s) to generate an electrical signal descriptive of the induced scattered-light time-dependent optical response d. processing the scattered-light-optical-response-descriptive electrical signal or a derived-signal thereof to compute therefrom one or more blood-shear-rate-descriptive (BSRD) signal(s), each BSRD signal characterized by a respective frequency-selection profile; e. in accordance with a correlation between (i) a result of the monitoring of the subject's behavior patterns of step (a) and (ii) feature(s) of the BSRD signal(s), training a subject-status-classifier capable of classifying a subject-status, in accordance with BSRD-signal-derived input, at least one a stress-state (e.g. type of stress or level of stress) a mood-state, a stress-resistance, and a cardiovascular fitness-status of the subject; f. at a later time, employing the trained classifier to perform at least one of the following of subject-status-classification operation(s) according to later BSRD signal data: (i) classifying a stress-state (e.g. type of stress or level of stress) of the subject; (ii) classifying a mood-state of the subject; (iii) classify a stress-resistance of the subject; (iv) classifying a cardiovascular fitness-status of the subject.

In some embodiments, the classifying of a stress-state comprises distinguishing between any two of mental-stress, emotional-stress and/or determining if a dominant stress mode of the subject is physical, emotional or mental.

In some embodiments, the classifying of a stress-state comprises quantifying an extent of stress and/or the classifying of the stress-resistance comprises classifying a stress-resistance-level of the subject.

In some embodiments, further comprising according to the subject-status-classification operation, (i) triggering at least one of an alert and therapy and/or (ii) serving advertisement to a user and/or (iii) updating the subject's user-profile and/or (iv) adjusting display-parameter(s) of a GUI operated by the user, wherein at least one of step(s) c-e is/are performed using a processor.

Apparatus for optically obtaining state and/or status information or changes therein about a warm-blooded subject the apparatus comprising:
 a. a diode laser or VCSEL configured to illuminate the subject's skin so as to scatter partially or entirely coherent light off of moving red blood cells (RBCs) of the subject to induce a scattered-light time-dependent optical response;
 b. photodetector(s) configured to generate an electrical signal descriptive of the induced scattered-light time-dependent optical response; and
 c. electronic circuitry configured to perform any method disclosed herein.

Second Additional Discussion

It is widely recognized that effective stress management could have a dramatic impact on health care and preventive medicine. In order to meet this need, efficient and seamless sensing and analytic tools for the non-invasive stress monitoring during daily life are required. The existing sensors still do not meet the needs in terms of specificity and robustness. We utilized a miniaturized dynamic light scattering sensor (mDLS) which is specially adjusted to measure skin blood flow fluctuations and provides multi-parametric capabilities. Based on the measured dynamic light scattering signal from the red blood cells flowing in skin, a new concept of hemodynamic indexes (HI) and oscillatory hemodynamic indexes (OHI) have been developed. This approach was utilized for stress level assessment for a few use-case scenario. The new stress index was generated through the HI and OHI parameters. In order to validate this new non-invasive stress index, a group of 19 healthy volunteers was studied by measuring the mDLS sensor located on the wrist. Mental stress was induced by using the cognitive dissonance test of Stroop. We found that OHIs indexes have high sensitivity to the mental stress response for most of the tested subjects. In addition, we examined the capability of using this new stress index for the individual monitoring of the diurnal stress level. We found that the new stress index exhibits similar trends as reported for to the well-known diurnal behavior of cortisol levels. Finally, we demonstrated that this new marker provides good sensitivity and specificity to the stress response to sound and musical emotional arousal.

Self-monitoring and ability to recognize and keep track of our own health and wellness has become possible with the growing capability of wearable sensors to generate data about our bodies. One of the most important parameters of health and wellness is the stress level. While in the short term, a certain amount of stress is essential for normal health, with chronic stress, those same responses can suppress functions that are not required for immediate survival. Numerous emotional and physical disorders have been linked to the chronic stress. One of them an increased risk of hypertension. In addition, an excessive level of mental stress in daily life, perceived stress during working hours and job stress has been considered as a risk factor for cardiovascular and anxiety disorders One of the great challenges for successful stress management is determining what causes the stress and how to quantify it. Thus, a capability to measure stress level variation continuously can be a key factor for the proper management of different stressors in our daily life.

Concerning stress monitoring, several questions should be addressed. The first one is how to express the physiological characteristics in terms of the measured data. The second question is how to convert these characteristics into specific quantitative physiological features.

A method and apparatus for quantification of stress level is disclosed. This quantification may be obtained by analyzing of the laser speckles responses to the skin blood flow dynamics. This information is used for the determination of the blood flow oscillatory characteristics. For this end, we introduced additional hemodynamic parameters that can be derived from the laser speckle signals. We called them the Hemodynamic Indexes (HI) and Oscillatory Hemodynamic Indexes (OHI). These characteristics are directly related to manifestations of the autonomic nervous system (ANS) and cardiovascular system (CVS) responses and could be used as complementary information to already existing non-invasive markers of stress.

Physiological parameters of stress—The autonomic nervous system (ANS) regulates most of the physiological activity of our body, including heart rate, blood pressure, peripheral blood flow and more. Parasympathetic (PSMP) and sympathetic (SMP) activities are part of ANS. Multiple processes regulate this system. Auto-regulatory mechanisms and hormones circulating in blood directly influence cardiovascular function by affecting the rate and stroke volume of the heart and the contraction or dilatation of blood vessels. Thus, peripheral blood hemodynamics exhibit many features underlying neural and cardio-vascular physiology. During stress events, the SMP is responsible for fast activation of the system and the PSMP is associated with relaxation. Eventually, real-life stress conditions produce changes in autonomic cardiac and vascular regulation.

It is commonly accepted fact that physiological rhythms affect nearly all body functions including PSMP and SMP. The ANS and endocrine signals are the principal mediators of this process. The level of stress, therefore, is also governed by these rhythms. This fact has been demonstrated by measuring significant daily variations including plasma concentrations of cortisol and other hormones.

Non-invasive markers of stress—Since the heart rate response to stressors is mediated by the ANS, variations of heart rate is a marker of parasympathetic or sympathetic activity. Quantitative analysis of HR activity is commonly performed by analyzing the fluctuation pattern of the heart rhymes. The duration between two consecutive R waves of the electrocardiogram (ECG) are defined as RR intervals. The variation of RR intervals or HRV (heart rate variability) is beat-to-beat alterations in heart rate. HRV is used as a function of sympatho-vagal balance of our body, which is closely related to the stress status. The most accurate HRV are measured by using ECG sensors. As an alternative methodology, PPG signal is used for the measurement of pulse-to-pulse variations. The waveform analysis of the PPG signal enables to determine peaks of the systolic wave and the pulse rate, and the HRV parameters can be approximately calculated.

However, the quantification of ANS functioning through the HRV characteristics is not always reliable. This is a result of the fact that physiological systems are comprised of multiple subsystems that exhibit a variety of regulation processes, operating over multiple time scales and conditions. Therefore, most of the measured characteristics are driven by very complex dynamics and more information is required to describe it.

Another well-known marker of stress is GSR (galvanic skin response). GSR is mediated mainly through the sympathetic nerve supply to the skin, and it is entirely attributable to changes in the sweat glands. One of technical disadvantages of GSR is that external factors such as temperature and humidity affect GSR measurements, and can lead to inconsistent results. In addition, GSR is sensitive mainly to the sympathetic responses and very important parasympathetic functioning is less reflected in the GSR signal.

Blood flow oscillations—One of the most important physiological characteristics of our body is the peripheral microcirculation of skin blood flow (SBF). The skin microcirculation is governed by arterioles, capillaries, and venules. SBF is regulated by centrally mediated neural mechanisms and by local humoral factors. Both rhythmic and stochastic changes in blood flow are governed, therefore, by CVS, neural and metabolic processes. These oscillations can be used as a source of information related to neural activity. The peripheral microcirculation or SBF is commonly studied through the laser Doppler flowmetry (LDF) technique.

Power spectrum analyses of LDF signals reveal a few distinct frequencies within the range of 0.01-2 Hz: the spectral component around 1 Hz corresponds to the cardiac activity. The other spectral components in the lowest frequency bands represent the influence of the respiration (0.3 Hz), myogenic activity or vasomotion (0.1 Hz) and neurogenic activity (0.04 Hz). The very specific oscillation appearing in the 0.05-0.15 Hz is frequently associated with so-called Mayer waves.

Several important studies addressing physiological interpretation of LDF fluctuations for stress monitoring have been published. For example, Goor et al. demonstrated that peripheral arterial vasoconstriction predicts stress-induced myocardial ischemia. They described that acute mental stress will lead to sympathetic nervous system activation and consequent peripheral vasoconstriction.

A variety of analytic tools for analysis and interpretation of blood flow fluctuations have been developed to date. These include frequency domain methods based on the Fourier transform, wavelet analysis, fractal analysis, singular spectrum analysis (SSA), multiscale entropy algorithm and more. The majority of the important results in processing and analysis of physiological signals consider the signals consisting of multi-periodic components mixed with random noise.

However, it has to be taken into consideration that the measured SBF signal is a convolution of many independent sources. Different vessels and events in different parts of the vessels including small arteries, arterioles and capillary vessels contribute independently and concurrently into the measured signal. Therefore, presenting SBF as a single variable which is a subject for oscillatory analysis is not sufficient for the comprehensive interpretation of the physiological activity.

By using a new kind of sensor (mDLS) and a new algorithmic approach, we developed a methodology for the signal decomposition into different components associated with different hemodynamic sources. This approach can be used for multi-dimensional analysis of the ANS and CVS manifestations. In this work, we demonstrated the usability of this new approach for assessment of the stress level.

Dynamic light scattering sensor for the measurement of skin blood flow: Sensor Design: The miniaturized dynamic light scattering sensor (mDLS of Elfi-Tech) enables measurement of the laser speckle signals originated by the skin blood flow. The mDLS sensor consists of the VCSEL chip which is closely located between two photodetectors (FIG. 42A), analog front end and data acquisition unit.

The very small distance between the detectors and the light source enables suppression of the multiple scattering effects of the reflected light. Only the photons that have been directly backscattered from the red blood cells are detected. The analog subtraction of two measured signals efficiently rejects the correlated components of the measured signal while uncorrelated DLS component is enhanced following the subtraction process. The number of laser speckles appearing on the photodetector determines speckle statistics. Presumably, the single backscattering events mainly are responsible for the measured signal. However, forward single scattering component might be involved in the overall signal. Indeed, thanks to the intensive scattering by the tissue (immobile "lattice" of the connective tissue) a significant number of photons are redirected to the backward hemisphere while these photons are actually scattered by the RBC's in forward direction[19]. Thus, in addition to the backscattered light, significant proportion of forward scattering light also detected. It should be noted that immobile scatterers or scatters that move with the same uniform velocity does not affect the temporal pattern of the measured signal.

Theoretical Discussion: Shear-Rate Model of the Flow

The relative movement of RBC's particles in the blood vessels is defined by a velocity profile of blood flow. In a very simplified case, for the vessel of radius R, axis symmetric velocity profiles v(r,t) can be described in cylindrical coordinates by this empirical relationship:

$$v(r, t) = v(0)\left[1 - \left(\frac{r}{R}\right)^\xi\right] f(t) - R \leq r \leq R; \tag{1}$$

Where v(0)—is maximum velocity at the center position r=0 and R is the radius of the vessel, f(t) is a periodic function of heart beat frequency, which is driven by difference between systolic and diastolic pressure wave and it is time phase-shifted with respect to the cardiac cycle, and $\xi$ represents the degree of blunting. For example, in 30 micron arterioles, there is a range of $\xi$=2.4-4 at normal flow rates.

If $\xi$=2, a parabolic velocity distribution is obtained (see FIG. 2 which shows Blood flow profile in the vessels).

One of the most important rheological parameters is velocity shear rate $\gamma$. It is given by:

$$\gamma = \frac{\partial v(r, t)}{\partial r} = \xi \cdot v(o, t) \cdot \frac{r^{\xi-1}}{R^\xi} \tag{2}$$

$$v(o, t) = \frac{\xi + 2}{\xi} <v(t) \tag{3}$$

Where ⟨v⟩—the velocity averaged over the cross-sectional area.

The rheological term "shear rate" is almost synonymous with velocity gradient. Shear rate is determined by the diameter of vessels. In blood vessels, the shear rate is not purely parabolic because of the Non-Newtonian rheological behaviors of the flowing blood. The non-Newtonian behavior of blood is due to the tendency of erythrocytes to aggregate at low shear rates. The highest shear rate is achieved when flow is fast and vessel diameter is small, and lowest shear rate is present when flow is slow and the vessel has a large diameter.

For small arterioles (from 15- to 60 microns diameter), the fluctuation of velocity from systolic to diastolic phases ranges from 1.5 mm/s to 2.5 mm/s, where mean velocity is around 10 mm/sec. The shear rate for small arterioles is between 400(1/sec) to 1400 (1/sec). For the capillaries from 5-10 microns, where an average velocity is around 0.2 mm/sec the shear rate can range from 50 to 100 (1/sec). Therefore, we are in the region where shear rate is sufficiently high to alter the particles space configuration before it can relax by the Brownian motion.

Theoretical Discussion: 1.1 Dynamic Light Scattering and Shear Rate

The measured signal can be expressed in terms of the dynamic light scattering (DLS) formalism. This formalism considers a relative movement of the scatterers as a major source of the laser speckles dynamics. When an ensemble of moving particles creates the scattering pattern on the detector, only the particles that are spatially correlated have to be taken into consideration. The particles separated by large distances give negligible contribution into the autocorrelation function or power spectrum of the signal. This relative movement of these closely spaced particles is the only characteristics that is preserved after the ensemble averaging.

It was shown that for the laminar flow the autocorrelation function g($\tau$) of measured DLS is dependent on the gradient of the velocity:

$$\nabla V(r) = V(x, r) - V(x, r + \nabla r) \tag{4}$$

Approximately, in laminar blood flow[18], the characteristic decay time of autocorrelation function can be given by:

$$g_i^f(\tau) \propto \exp(-\Gamma_i^f \tau^2) \tag{5}$$

$$\Gamma_i^B = D_i q^2 \tag{6}$$

where q=2·k·sin($\theta$/2), $\theta$—is scattering angle, k is wavelength number and ⟨d⟩ is the effective distance across the scattering volume in the direction of the velocity gradient. Superscript f signifies the relation to flow and subscript i is assigned to specific shear rate value.

It has to be pointed out, that for the shear rate model, the autocorrelation function of the signal decays with a time squire dependence rather than the simple exponential time dependence, which is the typical description for the Brownian motion.

$$g_i^f(\tau) \propto \exp(-\Gamma_i^f \tau^2) \quad (7)$$

$$\Gamma_i^B = D_f q^2 \quad (8)$$

$D_f$—diffusion coefficient for red blood cells. Subscript B relates to the Brownian motion. It has to be taken into consideration that the speckle signals are contributed by a variety of shear rates. The shear rates distribution can be associated with different types of the blood vessels or different regions inside the vessels. The lowest shear rate values correspond to the RBCs located mostly near the walls or flowing through the narrow capillary blood vessels and their decay function is dominated by the Brownian movement statistics. The very short decay time is associated with the large capillary vessels or arterioles.

We approximate the autocorrelation function G of the amplitude fluctuation as the weighed sum (Wi) of all speckle components with different time constants:

$$G(\tau) = \sum_i w_i^B \cdot g_i^B + \sum_i w_i^f \cdot g_i^f \quad (9)$$

According to Wiener-Khintchine theorem we can express the result in terms of the power spectrum:

$$P(\omega) = FT(G(\tau)) \quad (10)$$

Where FT—is Fourier transform. After substituting $G(\tau)$ from (7) and (8) we have:

$$P(\omega) = FT\left(\sum_i w_i^f \cdot g_i^f\right) + FT\left(\sum_i w_i^B \cdot g_i^B\right) = \sum_i w_i^f \cdot P_i^G(\omega) + \sum_i w_i^B \cdot P_i^L(\omega) \quad (11)$$

Where:

$$P(\omega) = \sum_i w_i^f \frac{\exp(\omega^2/4\Gamma_i^f)}{2 \cdot \sqrt{\Gamma_i^f}} + \sum_i w_i^B \frac{2 \cdot \Gamma_i^B}{(\Gamma_i^B)^2 + \omega^2} \quad (12)$$

Thus, the resulting spectrum is approximated by a superposition of two components: the Gaussian $P_\Gamma(\omega)$ and the Lorentzian $P_L(\omega)$.

As we have shown, the temporal statistics of the DLS signal may reflect the complex behavior reflecting neural functioning that are expressed through the peripheral skin blood circulation.

Hemodynamic Indexes Söderström et al showed that for an ensemble of particles moving with different velocities, the Doppler spectrum can be decomposed by different velocities. Liebert et al[4] showed that by decomposing the SBF signal measured from the skin, different oscillatory patterns are revealed.

In order to facilitate the interpretation of an oscillatory analysis, we introduced a so-called hemodynamic index HI. When the measured signal is expressed in terms of power spectrum P, we define hemodynamic index HI by:

$$HI([f_1, f_2], t) = \int_{f_1}^{f_2} P(\omega, t) d\omega \quad (13)$$

where $[f_1, f_2] = 2Pi*[w1, w2]$ defines the bandpass.

HI is defined by a specific bandpass and corresponds to a certain range of shear rates. Physiologically, each HI signifies different sorts of blood vessels or different regions in the vessels. For example, HI(t) that exhibits a pulsatile pattern resembling the blood pressure wave is associated with the arterioles. HI values which is associated with the capillary blood exhibits oscillatory behavior that differs from arteriole component of HI(t).

Based on (13) by using (11) and (12) we can easily get for $HI(\omega_1, \omega_2)$ the following:

$$HI \propto Erf\left(\frac{\omega_2}{2\sqrt{\langle\Gamma^f\rangle}}\right) - Erf\left(\frac{\omega_1}{2\sqrt{\langle\Gamma^f\rangle}}\right) + \frac{2\langle\Gamma^B\rangle + \text{Arctan}\left(\frac{\omega_2}{\langle\Gamma^B\rangle}\right) - \text{Arctan}\left(\frac{\omega_1}{\langle\Gamma^B\rangle}\right)}{\langle\Gamma^B\rangle} \quad (14)$$

Where $\langle\Gamma^B\rangle$ and $\langle\Gamma^f\rangle$ are representing an average shear rate and Brownian related constants in autocorrelation functions for each shear rate component.

In order to estimate $\Gamma_i^f = (\gamma_i \cdot (d)_i \cdot q)^2$ for capillary blood, for example, we can take $\gamma_i \approx 20$ sec$^{-1}$, $q_i = 2 \cdot \pi \cdot n/\lambda$ (backscattering: 180°), $\lambda = 0.8\mu$. where $(d)_i$ is defined as the distance across the scattering volume in the direction of the velocity gradient.

Figure 3A:
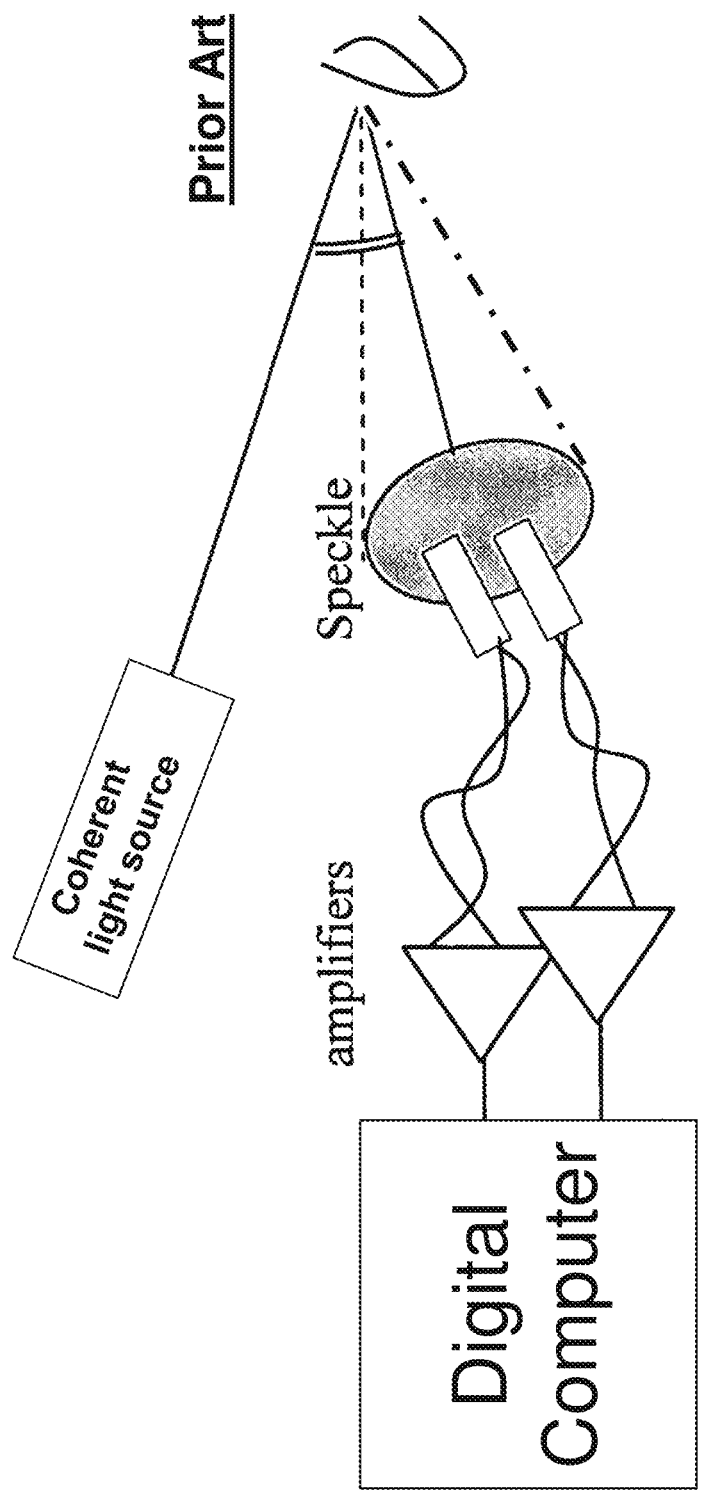
FIGS. 3A-3B and 7A-7B shows a prior art system (or portions thereof) and a prior art method for in-vivo dynamic light scattering.
Figure 3B:
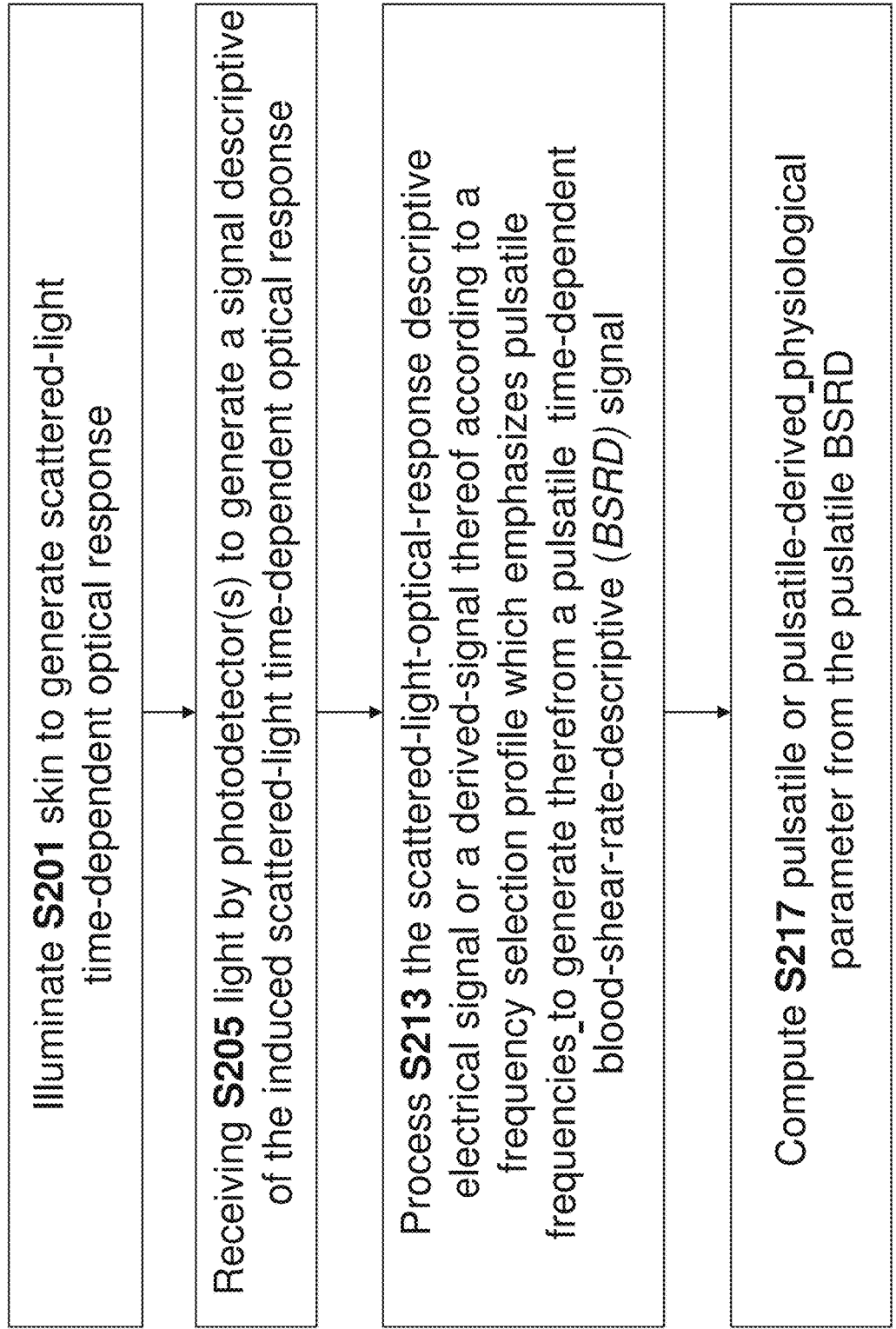
Figure 4:
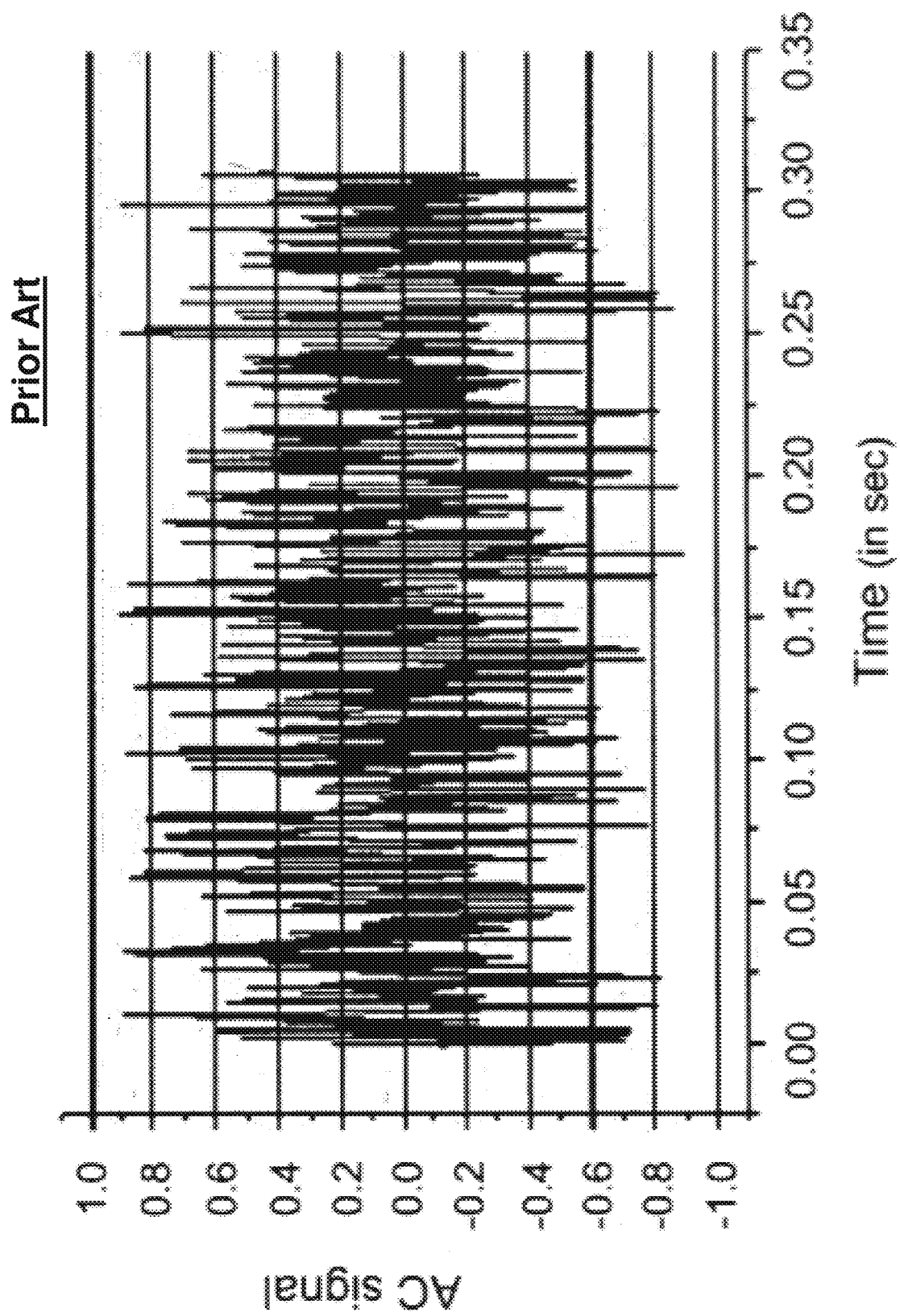
FIG. 4 describes an optical response signal.
Figure 5A:
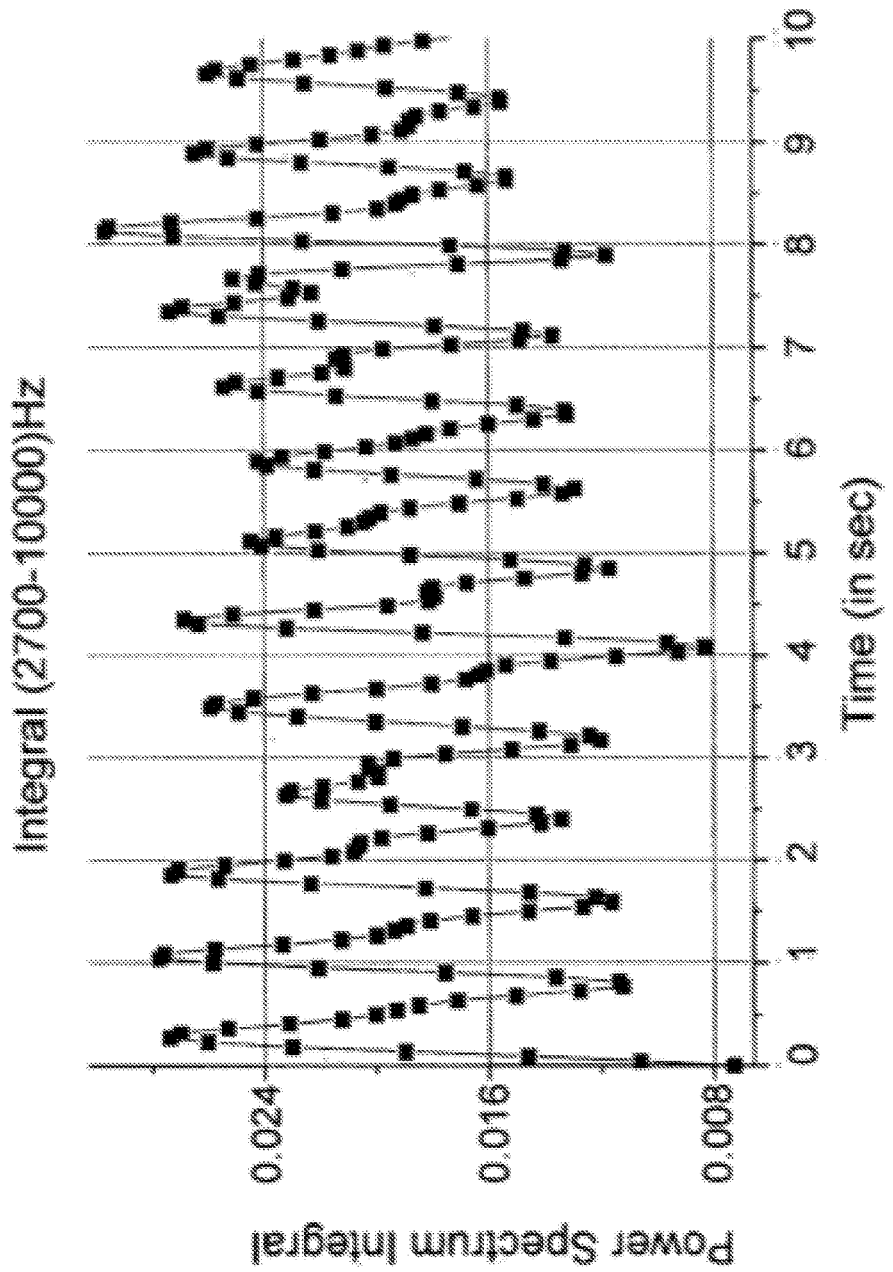
FIGS. 5A-5B describe a pulsatile and non-pulsatile BSRD.
Figure 5B:
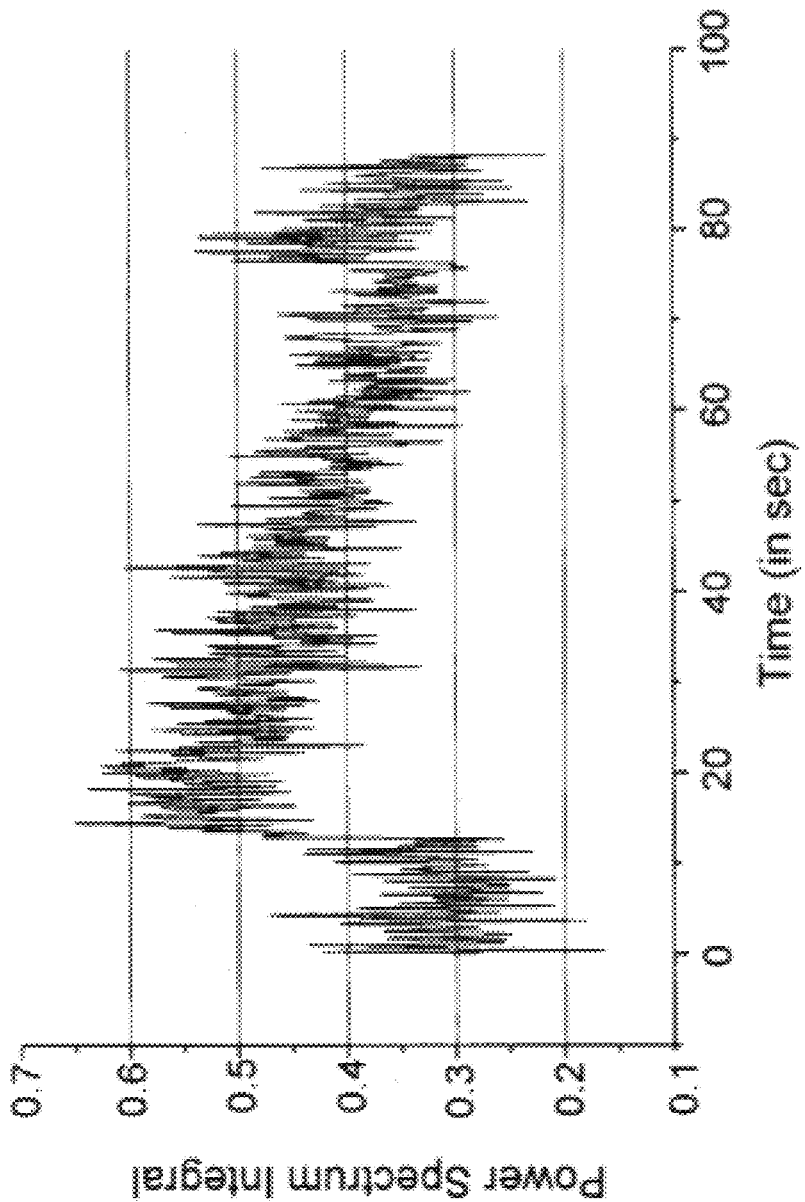

On FIG. 3 we can see an example of behavior of two different HI's. HI1 is defined by the low shear rate of 10 sec$^{-1}$ for capillary blood and HI2 is calculated for 50 sec$^{-1}$ plotted as function of mean bandpasses frequency. The f2-f1 for each bandpass was chosen 1 KHZ.

Figure 33:
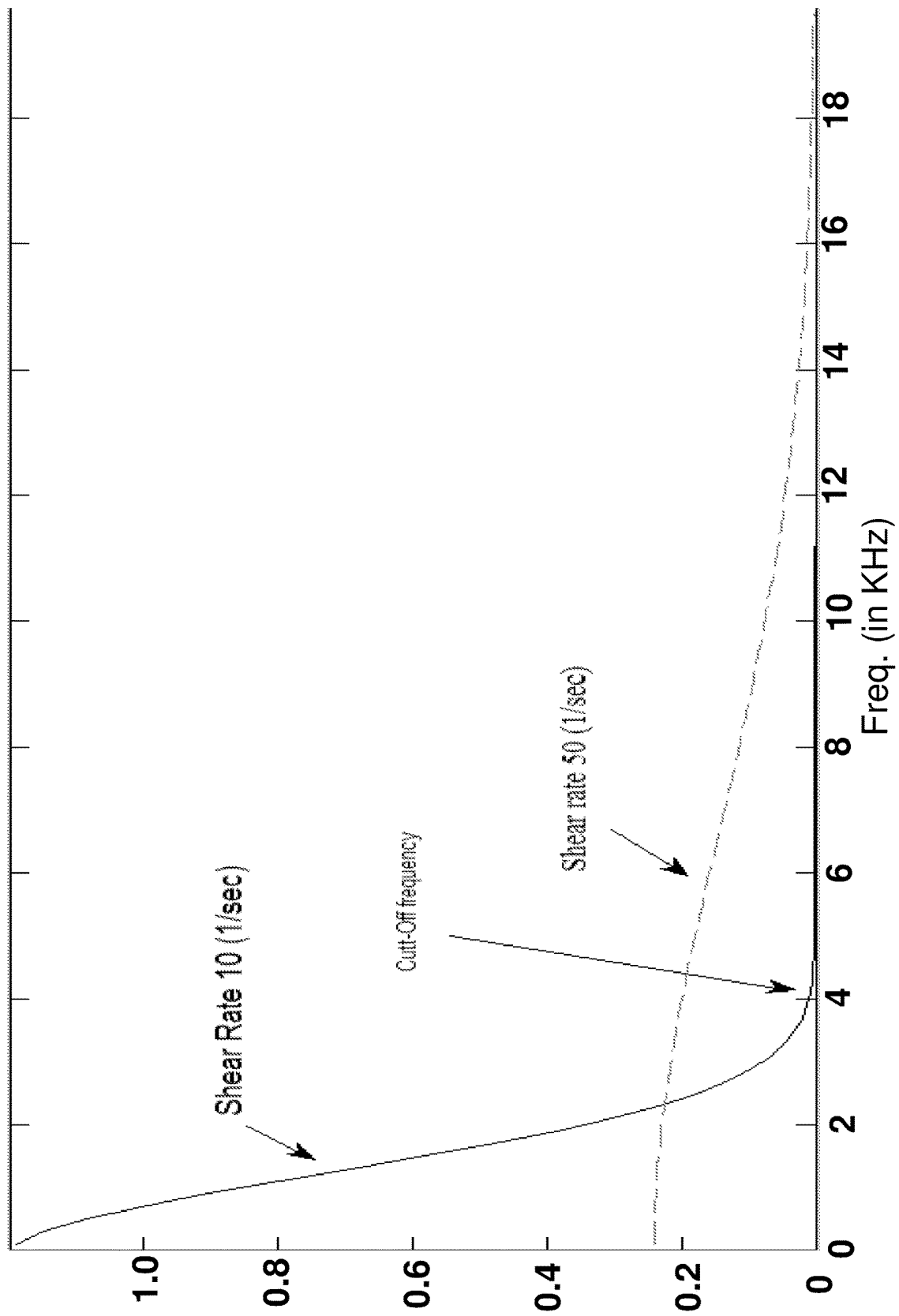

FIG. 33 shows HI for as function of the frequencies

In this example it is seen that specific HI1 is entirely defined under a cur-off frequency of 4 KHZ. Under 1 Kzh the Brownian component has to be taken into consideration. We can interpret the HI dependence on the shear rate by rendering to each bandpass a corresponding effective velocity or shear rates values. Differentiation between the shear rates is closely related to the type of the blood, like capillary, arterial, endothelial etc. The HI that is related to very low frequency range addresses the endothelial interaction with RBC's[7] where the high frequency region is characterized mostly the pulsatile blood flow. The oscillatory characteristics are served as an additional measure that has to be performed for each HI. Following the calculation of a set of HI variables we can carry out different types of oscillatory analysis for each of them. To simplify our analysis we used a discrete physiological oscillation filters bank. For example, in this study we used the following bands; [0.005, 0.05] Hz—endothelial related band, defined as (E), ([0.05, 0.15] Hz—myogenic wave region (M), [0.15, 0.6]—Respiratory (R), [0.6, 3] Hz, Pulsatile (P). The corresponding normalized power spectrum component of HI over the measurement interval T are defined as OHI (oscillatory HI components), so for each HI we can select a number of oscillatory components.

Altogether, this full physiological pattern is expressed through so-called OHI matrix, which incorporates information about the time-dependent behavior of different shear rates being represented by different HI's. If we use n frequency (f) bandpass intervals then we get $$OHI = \begin{cases} OHI([f_1,f_1+\nabla f], E), OHI([f_1,f_1+\nabla f], M), OHI([f_1,f_1+\nabla f], R), OHI([f_1,f_1+\nabla f], P) \\ \cdots \\ OHI([f_n,f_n+\nabla f], E), OHI([f_n,f_n+\nabla f], M), OHI([f_n,f_n+\nabla f], R), OHI([f_n,f_n+\nabla f], P) \end{cases} \quad (15)$$

Generally, this matrix can be expended by introducing the additional non-deterministic characteristics and variables of the fluctuations, like fractal dimensions, Hurst exponents and more.

The evolution of OHI matrix in time can be represented in multidimensional space as a trajectory of physiological status. Together with heart rate and HRV, the dynamics of OHI matrix parameters reflects variety of cardio-vascular and neurological processes.

Physiological manifestations of the hemodynamic indexes—The mDLS signals where collected while a subject was sitting comfortably in a chair. The sensor was attached to the upper side of the wrist.

Figure 34A:
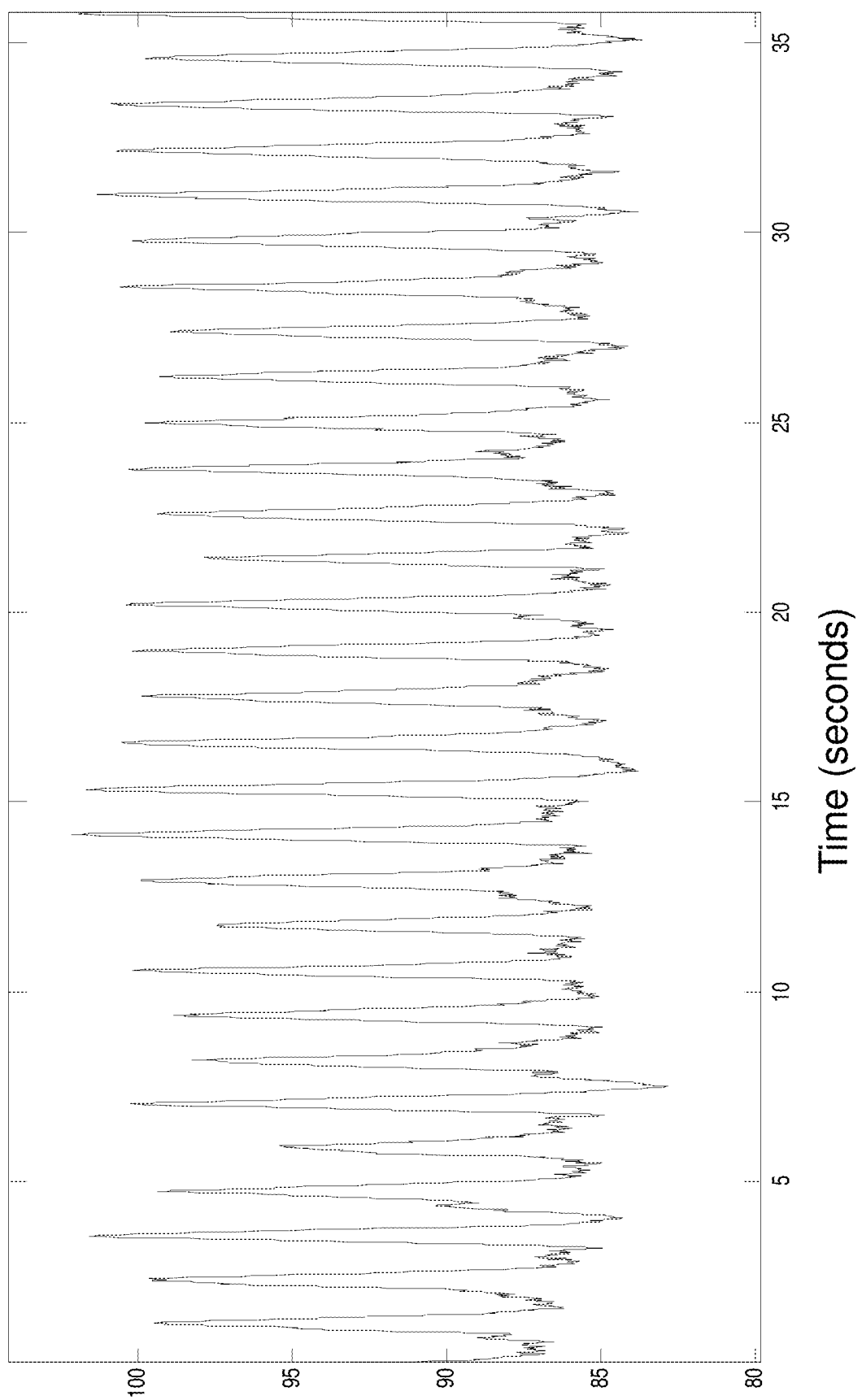
Figure 34B:
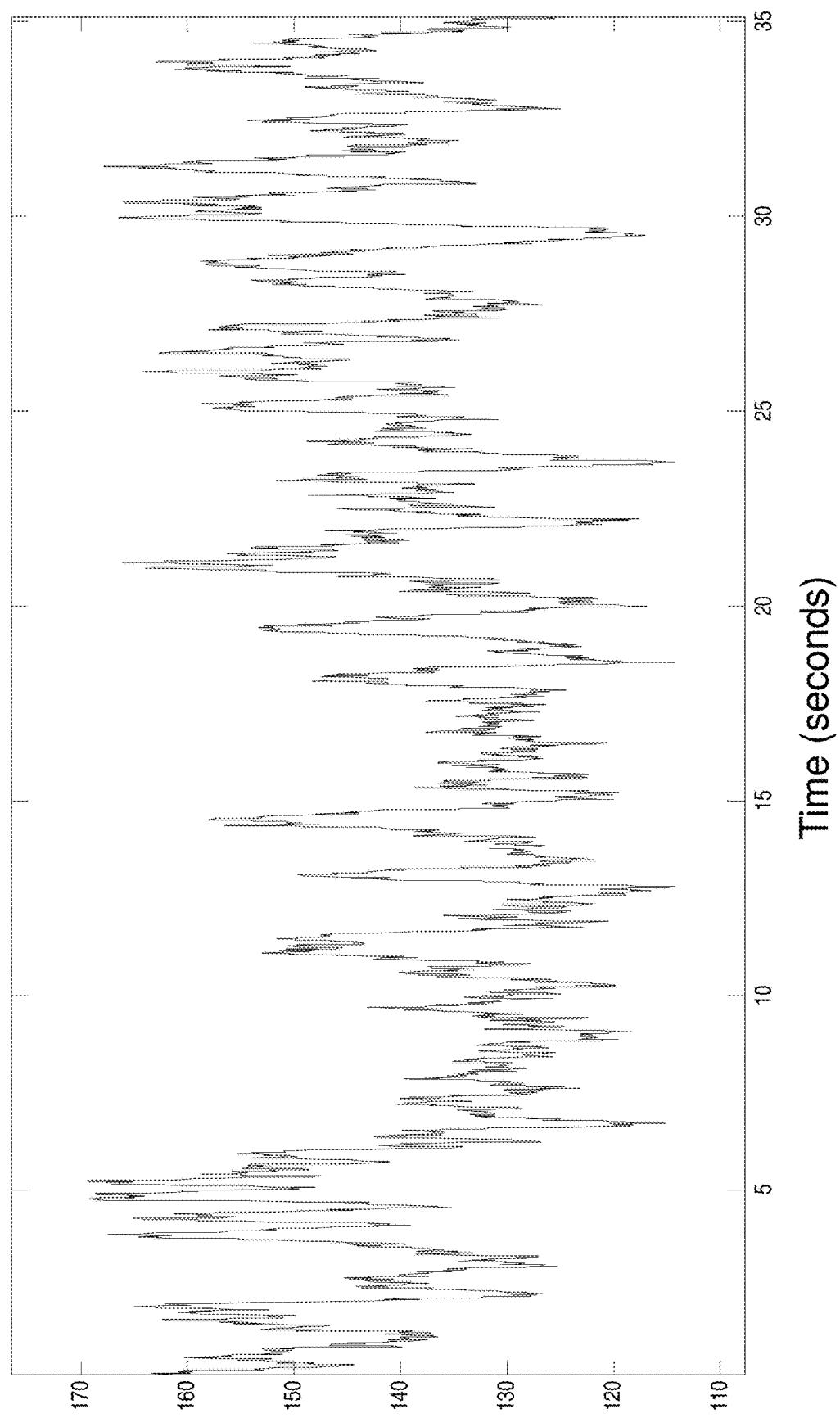

FIGS. 34*a* and 34*b* each exemplify two different OHI components extracted from the mDLS signal. On FIG. 34A we show HI ([7.5 KHZ, 30 KHZ], clearly corresponding to the pulsatile blood pressure waveform. On FIG. 34B the time dependency pattern for HI ([0, 1 KHZ) for the same measurement interval is presented. The fluctuations of this HI variable are related mainly to the capillary blood.

Figure 35A:
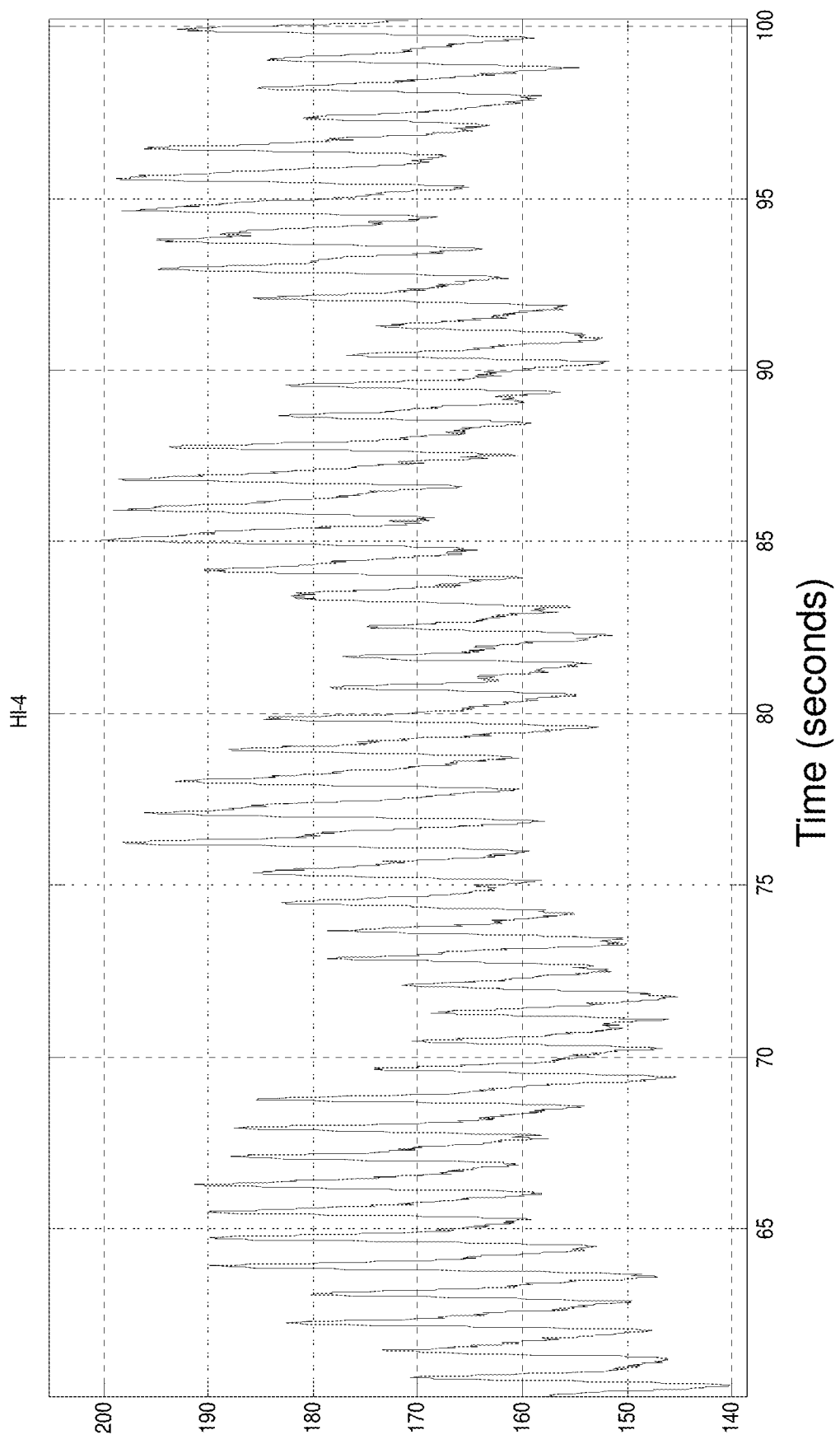
Figure 35B:
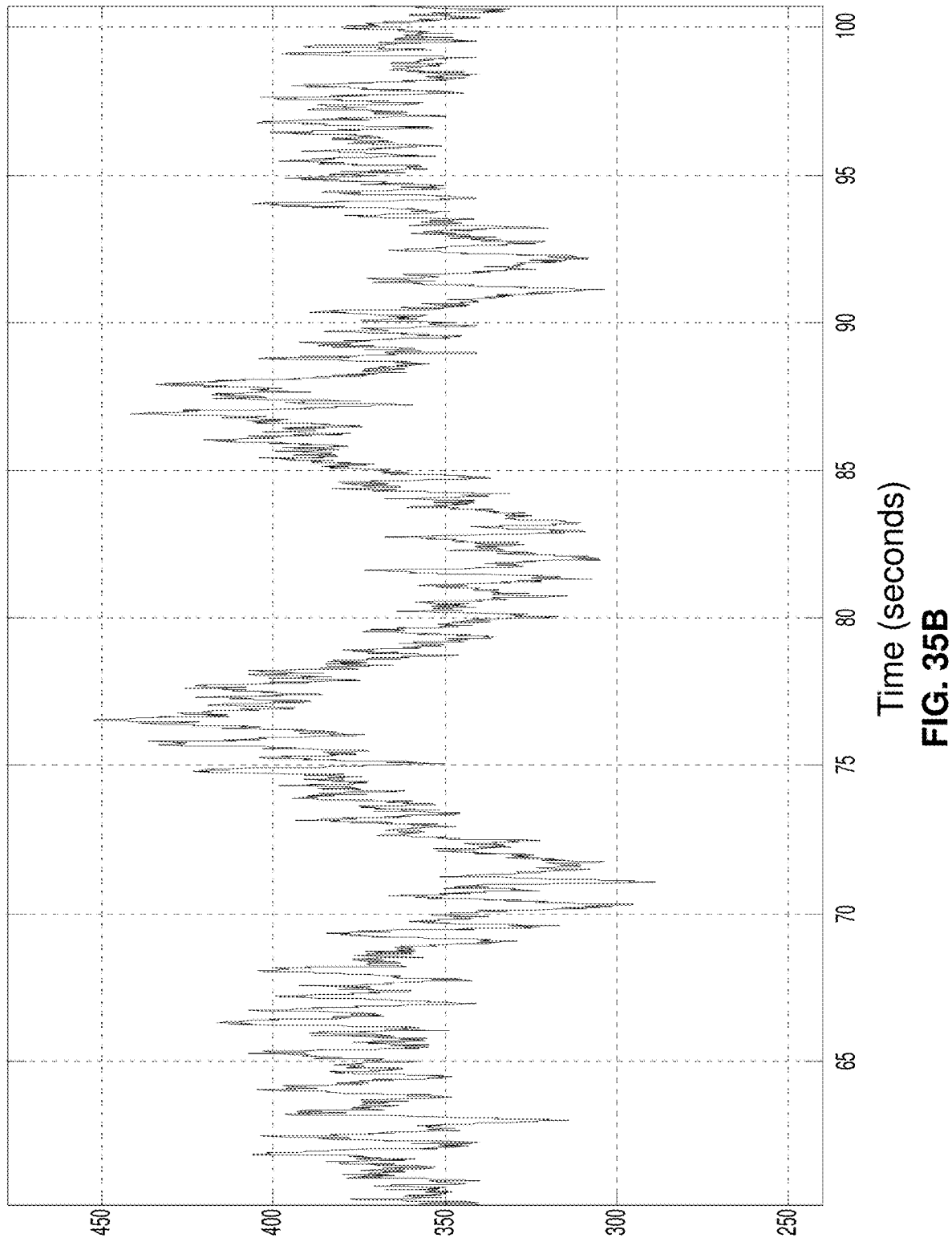
Figure 36A:
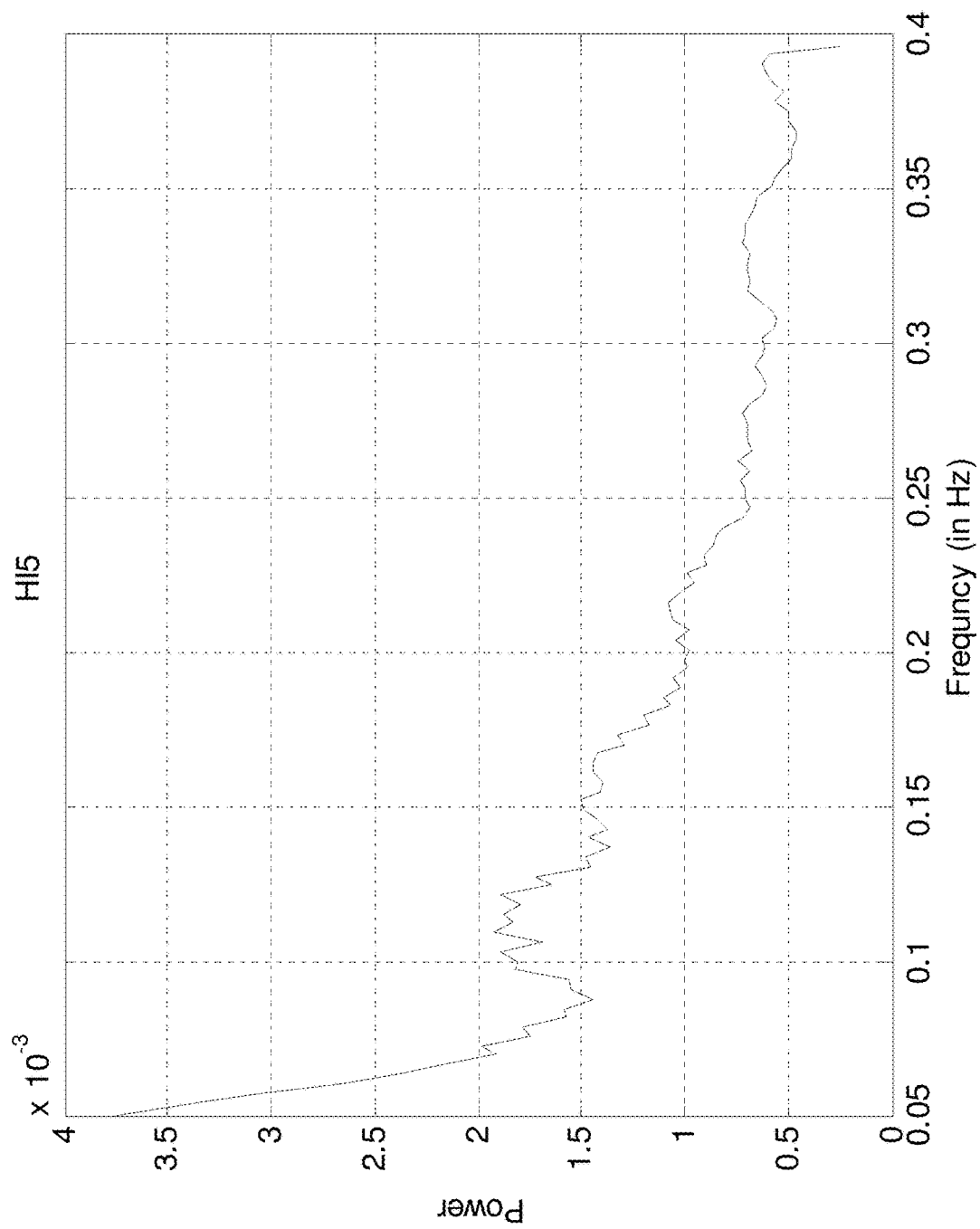
Figure 36B:
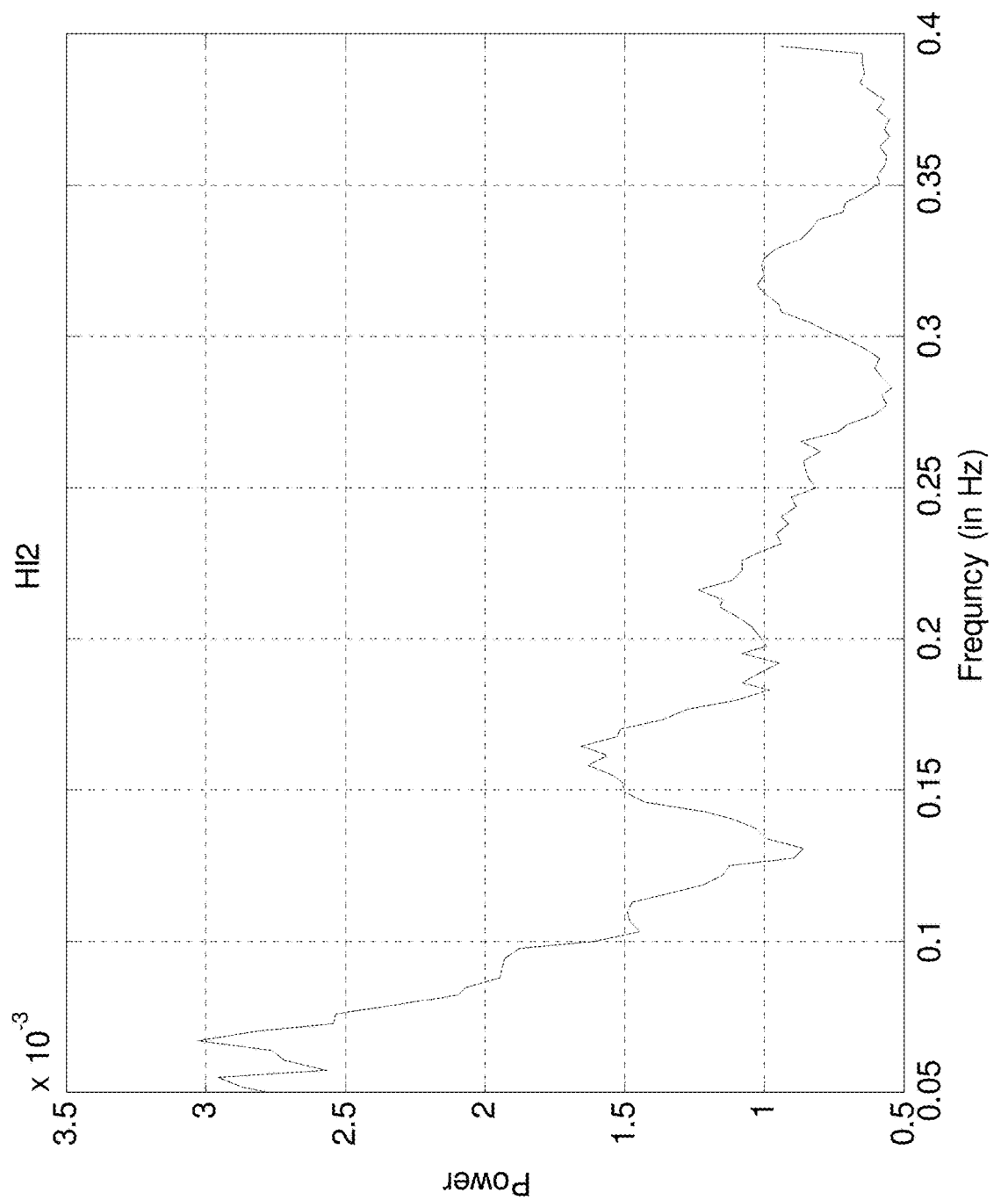

FIG. 34A shows HI for the pulsatile component; FIG. 34B shows HI for the non-pulsatile component;

In other examples (FIG. 35A and FIG. 35B) the so-call Mayer oscillation is seen (around 0.1 Hz). The 0.1 pulsatile component for HI(8 KHZ, 30 Hz, t) is modulated by the 0.1 Hz oscillation. FIG. 34B shows that the non-pulsatile component HI([1-3 KHZ] is modulated by 0.1 Hz as well. FIG. 35A shows a Mayer wave in pusalite HI. FIG. 35B shows Mayer wave in non-pusalite HI.

Different HI(t) reflect, therefore, different physiological patterns that can be expressed in terms of oscillation analysis. Examples of the Oscillation patterns for different HI in power spectrum graphs are shown on FIGS. 6*a* and 6*b*

Figure 6A:
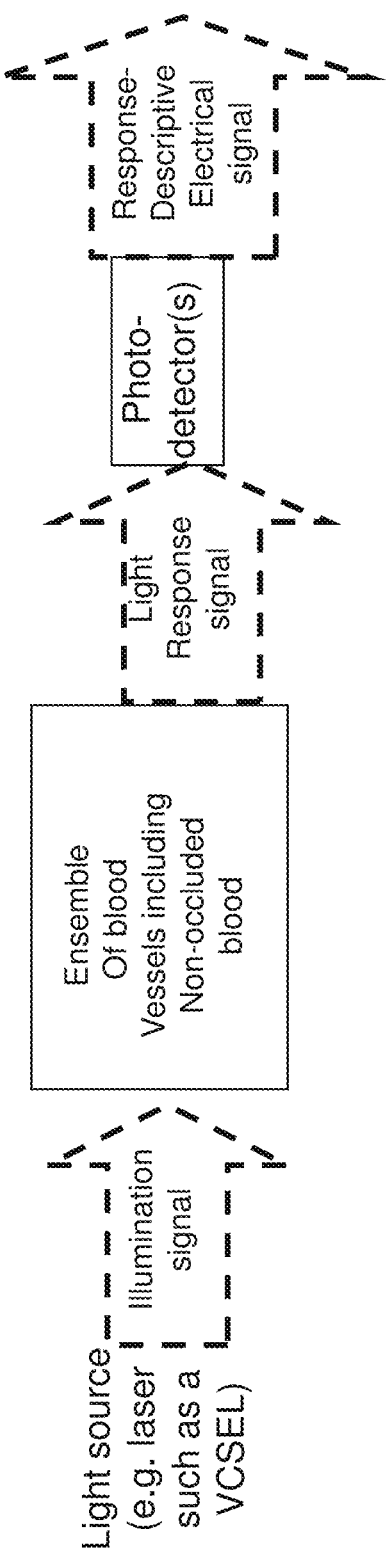
FIGS. 6A-6B describe data-flow related to DLS.

FIG. 6*a*. OHI for pusalite component

Figure 6B:
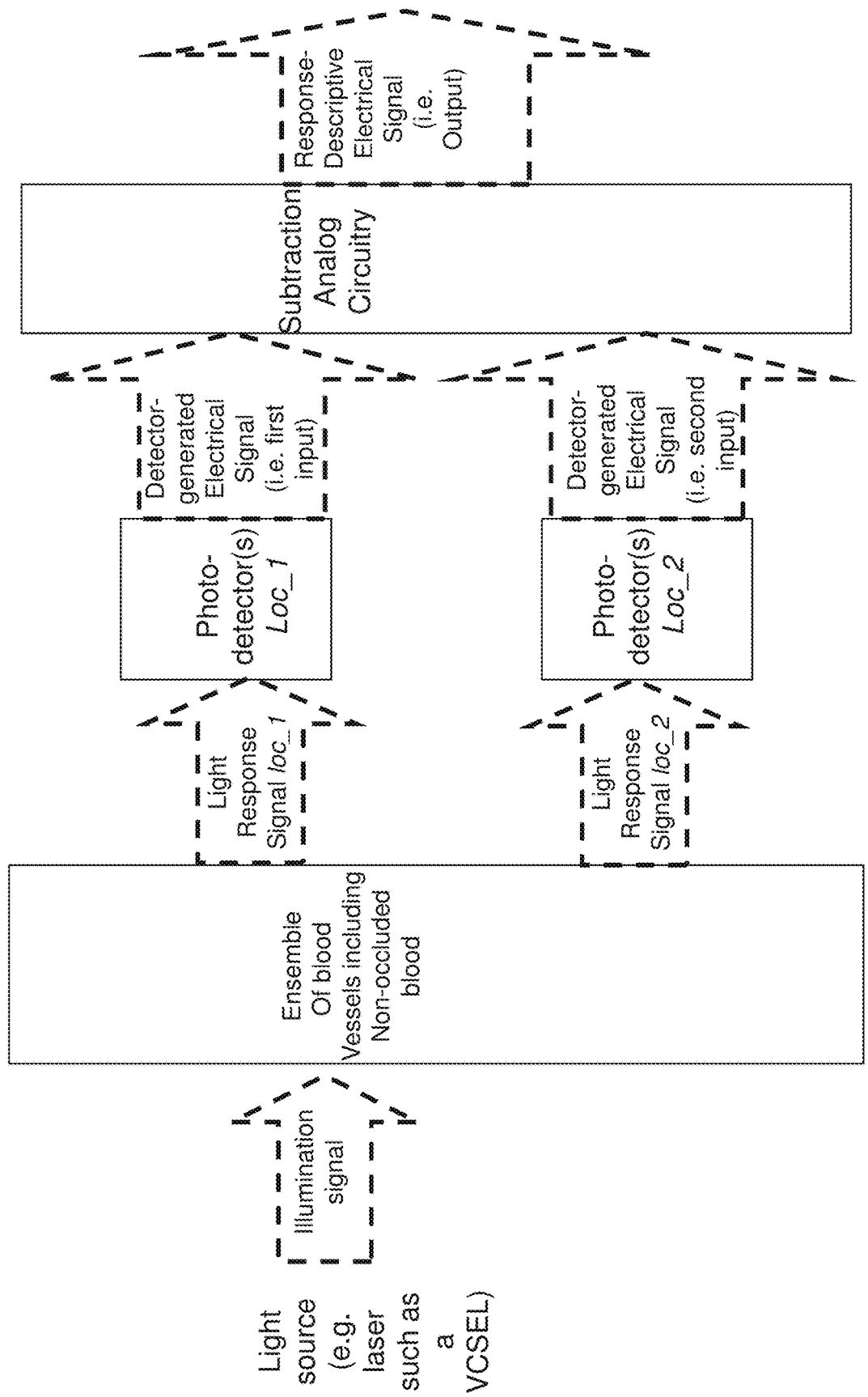

FIG. 6*b*. OHI of non-pusalite component.

Recently the usefulness of Hemodynamic Indexes was demonstrated in an animal study[13]. In this study HI's behavior tested for postoperative evaluation of anastomotic microcirculation. It was shown that only HI corresponding to the low shear rate (non-pulsatile) and can be used for the detection of anastomotic leakage in colorectal surgery. In order to study usability of OHI matrix for assessment of stress response we created an experimental set up when the examined subject is exposed to physiological stimulus.

PCT/IB2015/001157, filed on May 21, 2015, is incorporated herein by reference. Any combination of any feature described in the present document and any feature or combination of feature(s) described in PCT/IB2015/001157 is within the scope of the invention.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

What is claimed is:

1. A method for optically measuring state and/or status information or changes therein about a warm-blooded subject, the method comprising:
   a. illuminating a portion of the subject's skin or tissue by a VCSEL (vertical cavity surface emitting laser) or a diode laser to scatter partially or entirely coherent light off of the subject's moving red blood cells (RBCs) to induce a scattered-light time-dependent optical response;
   b. receiving the scattered light by a photodetector(s) to generate an electrical signal descriptive of the induced scattered-light time-dependent optical response;
   c. processing the scattered-light-optical-response-descriptive electrical signal or a derived-signal thereof to compute therefrom one or more blood-shear-rate-descriptive (BSRD) signal(s), each BSRD signal characterized by a respective frequency-selection profile;
   d. electronically analyzing features of the BSRD signal(s) of the BSRD signal group to quantify a prominence of a physiological signal within the BSRD, the BSRD being selected from the group consisting of a Mayer wave, a neurogenic signal and a myogenic; and
   e. computing, from the results of the quantifying of the prominence, the state and/or status information or changes therein.

2. The method of claim 1 wherein the measured state is a neurological state.

3. The method of claim 1 wherein the measured state is a fitness state.

4. The method of claim 1 wherein state and/or status information comprises at least one of: a stress-state, a cardiovascular-fitness, a pain-state, a fatigue-state, a stress-resistance, a diurnal fluctuation of stress or stress-resistance, and an apnea event.

5. The method of claim 1 wherein the non-pulsatile BSRD signal(s) is subjected to a stochastic analysis or to a stationary-status analysis that quantifies a stationary/non-stationary status of the BSRD signal(s) and the state and/or status information or changes therein is computed from the results of the stochastic and/or stationary-status analysis.

6. A method for optically measuring state and/or status information or changes therein about a warm-blooded subject, the method comprising:
   a. illuminating a portion of the subject's skin or tissue by a VCSEL (vertical cavity surface emitting laser) or a diode laser to scatter partially or entirely coherent light off of the subject's moving red blood cells (RBCs) to induce a scattered-light time-dependent optical response;

b. receiving the scattered light by a photodetector(s) to generate an electrical signal descriptive of the induced scattered-light time-dependent optical response or an AC component thereof;

c. processing the scattered-light-optical-response-descriptive electrical signal or a derived-signal thereof to compute therefrom at least two or at least three or at least four blood-shear-rate-descriptive (BSRD) signals selected from the BSRD signal group, each blood-rate-descriptive BSRD signal characterized by a different respective frequency-selection profile, the BSRD signal group consisting of the following signals: (i) a [sub −200 Hz, ~300 Hz] BSRD signal; (ii) a [~300 Hz, ~1000 Hz] BSRD signal; (iii) a [~1000 Hz, ~4000 Hz] BSRD signal and (iv) a [~4000 Hz, z Hz] (z>=7,000) BSRD signal;

d. electronically analyzing features of the at least two or at least 3 or at least 4 BSRD signals of the BSRD signal group;

e. in accordance with the results of the electronically analyzing of the at least two or at least 3 or at least 4 BSRD signals, computing the state and/or status information or changes therein.

7. The method of claim 6 wherein the measured state is a neurological state.

8. The method of claim 6 wherein the measured state is a fitness state.

9. The method of claim 6 wherein state and/or status information comprises at least one of: a stress-state, a cardiovascular-fitness, a pain-state, a fatigue-state, a stress-resistance, a diurnal fluctuation of stress or stress-resistance, and an apnea event.

10. The method of claim 6 wherein at least one of the non-pulsatile BSRD signal(s) is subjected to a stochastic analysis or to a stationary-status analysis that quantifies a stationary/non-stationary status of the BSRD signal(s) and the state and/or status information or changes therein is computed from the results of the stochastic and/or stationary-status analysis.

11. The method of claim 6 wherein the method is performed adaptively such that:
   i. one or more non-pulsatile candidate BSRD signal(s) are scored so that (A) a greater signal energy and a lower pulsatile signal-contribution increase a quality-score of a rated non-pulsatile candidate BSRD signal and (B) conversely, a lower signal energy and a greater pulsatile signal-contribution decrease a quality-score of a rated non-pulsatile candidate BSRD signal; and
   ii. the subject-status-classification operation is performed dynamically so as to assign greater weight to candidate BSRD signal(s) having a higher score and to assign a lower weight to candidate BSRD signal(s) having a lower score.

12. The method of claim 6 wherein:
   i. a pulsatile BSRD signal(s) is also generated from the scattered-light-optical-response-descriptive electrical signal or derived signal thereof;
   ii. subject-status-classification operation(s) is performed according to both feature(s) of the pulsatile BSRD signal(s) and the results of the stochastic and/or stationary-status analysis of the non-pulsatile BSRD signal(s);
   iii. the pulsatile BSRD signal(s) is rated according to a prominence of blood-pressure-waveform feature(s) therein; and
   iv. the non-pulsatile BSRD signal(s) is dynamically computed such that the frequency-selection profile thereof is dynamically adjusted.

13. The method of any claim 6 wherein the measuring comprises classifying a stress-state so as to distinguish between any two of mental-stress, emotional-stress and/or determining if a dominant stress mode of the subject is physical, emotional or mental.

14. Apparatus for optically measuring state and/or status information or changes therein about a warm-blooded subject the apparatus comprising:
   a. a diode laser or VCSEL configured to illuminate the subject's skin so as to scatter partially or entirely coherent light off of moving red blood cells (RBCs) of the subject to induce a scattered-light time-dependent optical response;
   b. photodetector(s) configured to generate an electrical signal descriptive of the induced scattered-light time-dependent optical response; and
   c. electronic circuitry configured to:
      i. process the scattered-light-optical-response-descriptive electrical signal or a derived-signal thereof to compute therefrom one or more blood-shear rate-descriptive (BSRD) signal(s), each BSRD signal characterized by a respective frequency-selection profile;
      ii. electronically analyze features of the BSRD signal(s) of the BSRD signal group;
      iii. in accordance with the results of the electronically analyzing of the at least two frequency-interval-specific shear-rate-descriptive signals, perform at least one of the following of subject-status-classification operation(s):
         A. classify a stress-state (e.g. type of stress or level of stress) of the subject;
         B. classify a mood-state of the subject;
         C. classify a stress-resistance of the subject;
         D. classify a cardiovascular fitness-status of the subject;
      wherein a frequency-selection profile of the BSRD(s) signal is computed dynamically so to adaptively maximize a prominence of a predetermined non-pulsatile physiological signal within the BSRD(s) and/or wherein the classification operation is performed dynamically so that a weight assigned to a BSRD signal is adaptively determined to increase a weight of BSRD signal(s) whose frequency-selection profile correspond to a greater prominence of the predetermined non-pulsatile physiological signal at the weight-expense of BSRD signal(s) whose frequency-selection profile correspond to a lesser prominence of the predetermined non pulsatile physiological signal.

* * * * *